(12) United States Patent   (10) Patent No.: US 8,357,791 B2
Nassif et al.   (45) Date of Patent: Jan. 22, 2013

(54) **DNA AND PROTEINS OR PEPTIDES SPECIFIC OF BACTERIA OF THE *NEISSERIA MENINGITIDIS* SPECIES, METHODS FOR OBTAINING THEM AND BIOLOGICAL APPLICATIONS THEREOF**

(75) Inventors: Xavier Nassif, Paris (FR); Colin Tinsley, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 13/010,139

(22) Filed: Jan. 20, 2011

(65) Prior Publication Data

US 2011/0313026 A1   Dec. 22, 2011

Related U.S. Application Data

(60) Continuation of application No. 12/389,992, filed on Feb. 20, 2009, now abandoned, which is a continuation of application No. 11/638,579, filed on Dec. 14, 2006, now abandoned, which is a division of application No. 11/045,208, filed on Jan. 31, (Continued)

(30) Foreign Application Priority Data

Jul. 12, 1996   (FR) ...................................... 96 08768

(51) Int. Cl.
*A61K 31/7088* (2006.01)
(52) U.S. Cl. ..................... 536/23.7; 435/6.15; 435/6.11; 436/94
(58) Field of Classification Search ........................ None
See application file for complete search history.

(56) References Cited

U.S. PATENT DOCUMENTS

| 5,436,142 A | * | 7/1995 | Wigler et al. ................ 435/91.2 |
| 5,445,933 A |   | 8/1995 | Eadie et al. |
| 5,523,217 A |   | 6/1996 | Lupski et al. |
| 5,698,438 A |   | 12/1997 | Stojiljkovic et al. |
| 5,747,252 A |   | 5/1998 | Yang et al. |
| 5,837,468 A | * | 11/1998 | Wang et al. ................... 435/6.12 |
| 6,086,896 A | * | 7/2000 | Sparling et al. ............ 424/250.1 |

(Continued)

FOREIGN PATENT DOCUMENTS

| EP | 0 301 992 | 2/1989 |
| EP | 0 337 896 | 10/1989 |

(Continued)

OTHER PUBLICATIONS

Dempsey, J et al, Journal of Bacteriology, vol. 177(22), Nov. 1995, pp. 6390-6400.*

(Continued)

*Primary Examiner* — Albert Navarro
*Assistant Examiner* — Ginny Portner
(74) *Attorney, Agent, or Firm* — Nixon & Vanderhye P.C.

(57) ABSTRACT

The DNA of the invention are characterized in that they concern the whole or part of genes, with their reading frame, to be found in *Neisseria meningitidis*, but not in *Neisseria gonorrhoeae*, or in *Neisseria lactamica* except the genes involved in the biosynthesis of the polysaccharide capsule, frp A, frp C, opc, por A, rotamase the sequence IC1106, IgA protease, pilline, pilC, transferrin binding proteins and opacity proteins. The invention also concerns the polypeptides corresponding to these DNA and the antibodies directed against these polypeptides. It is applicable in the prevention and the detection of meningococcus induced infections and meningitis.

16 Claims, 9 Drawing Sheets

Related U.S. Application Data 2005, now abandoned, which is a division of application No. 09/928,457, filed on Aug. 14, 2001, now Pat. No. 7,029,845, which is a continuation of application No. 09/214,759, filed as application No. PCT/FR97/01295 on Jul. 11, 1997, now abandoned.

(56) References Cited

U.S. PATENT DOCUMENTS

| | | | |
|---|---|---|---|
| 6,121,037 A | 9/2000 | Stojiljkovic et al. | |
| 6,123,942 A | 9/2000 | Stojiljkovic et al. | |
| 6,277,382 B1 | 8/2001 | Stojiljkovic et al. | |
| 6,709,660 B1 * | 3/2004 | Scarlato et al. | 424/250.1 |
| 6,835,384 B1 | 12/2004 | Aujame et al. | |
| 7,026,157 B1 | 4/2006 | Stojiljkovic et al. | |
| 7,029,845 B2 | 4/2006 | Nassif et al. | |
| 7,070,927 B2 | 7/2006 | Drmanac | |
| 7,368,556 B2 | 5/2008 | Nassif et al. | |
| 7,384,768 B2 | 6/2008 | Aujame et al. | |
| 7,714,121 B2 * | 5/2010 | Scarlato et al. | 536/23.7 |
| 2006/0063167 A1 | 3/2006 | Nassif et al. | |
| 2007/0082361 A1 | 4/2007 | Nassif et al. | |
| 2009/0305275 A1 | 12/2009 | Nassif et al. | |

FOREIGN PATENT DOCUMENTS

| | | |
|---|---|---|
| EP | 0 452 596 | 10/1991 |
| EP | 548012 A | 6/1993 |
| WO | WO 88/03957 | 6/1988 |
| WO | WO 90/15621 | 12/1990 |
| WO | WO 94/05703 | 3/1994 |
| WO | 9407356 A | 4/1994 |

OTHER PUBLICATIONS

Tinsley, et al, PNAS, vol. 93, Oct. 1, 1996, pp. 11109-11114.*
Omer, H et al, PLOS One, Feb. 2011, vol. 6(2), e17145, pp. 1-15, Genotypic and Phenotypic Modifications of *Neisseria meningitidis* after an accidental human passage.*
Palmer, HM et al, FEMS Microbiology Letters, vol. 110, pp. 139-146, 1993.*
U.S. Appl. No. 09/214,759, filed Apr. 1999, Nassif et al.
Zhou et al, "Sequence diversity within the argF, fbp and recA genes of natural isolates of *Neisseria meningitidis*: interspecies recombination within the argF gene", Mol Microbiol. Aug. 1992, 6 (15), pp. 2135-2146, England.
Devi et al, "Antibodies to poly[(2-8)-alpha-N-acetylneuraminic acid] and poly[(2-9)-alpha-N-acetylneuraminic acid] are elicited by immunization of mice with *Escherichia coli* K92 conjugates: potential vaccines for groups B and C meningococci and *E. coli* K1.", Proc Natl Acad Sci USA, Aug. 15, 1991, 88 (16, pp. 1715-1719.
Wolff et al, "Identification and characterization of specific sequences encoding pathogenicity associated proteins in the genome of commensal *Neisseria* species", FEMS Microbiol Lett, Jan. 15, 1995, 125 (2-3), pp. 255-263, Netherlands.
Petering et al, "Genes associated with meningococcal capsule complex are also found in *Neisseria gonorrhoeae*", J Bacteriol, Jun. 1996, 178 (11) pp. 3342-3345, United States.
Frosch et al, "Evidence for a common molecular origin of the capsule gene loci in gram-negative bacteria expressing group II capsular polysaccharides", Mol Microbiol, May 1991, 5 (5), pp. 1251-1263, England.
Frosch et al, "Phospholipid substitution of capsular polysaccharides and mechanisms of capsule formation in *Neisseria meningitidis*", Mol Microbiol, May 1993, 8 (3), pp. 483-493, England.
Frosch et al, "Conserved outer-membrane protein of *Neisseria-meningitides* involved in capsule expression" Infection and Immunity, 1992, 60, pp. 798-803.

Strathdee et al, "Identification of Epidemiologic markers for *Neisseria-meningitidis* using difference analysis", Gene, 1995, 166, pp. 105-110.
Lauerman et al, "Avian mycoplasma identification using polymerase chain reaction amplicon and restriction fragment length polymorphism analysis", Avian Dis, Oct.-Dec. 1995, 39, (4) pp. 804-811. United States.
Zhang, Q et al, Antimicrobiol Agents Chemother., vol. 34(8), pp. 1523-1528, Aug. 1990.
Knight et al., "Identification and Characterization of a Novel Insertion Sequence, IS 1106, Downstream of the porA Gene in B15 *Neisseria meningitidis*", Molecular Microbiology (1992) 6(11), pp. 1565-1573.
Dempsey, J. et al, Journal of Bacteriology, vol. 177, No. 22, Nov. 1995, pp. 6390-6400 (Nov. 1995).
Virji, M. et al, Molecular Microbiology, vol. 6(19), Oct. 1992, pp. 2785-2795 (abstract).
Virji, M. et al, Molecular Microbiology, Vo. 10(3), apges 499-510, Nov. 1993 (abstract).
Frosch et al., "Phospholipid Substitution of Capsular Polysaccharides and Mechanisms of Capsule Formation in *Neisseria meningitidis*", Molecular Microbiology (1993)8(3), pp. 483-493.
Schutte et al., "Isolation of YAC Insert Sequences by Representational Difference Analysis", Nucleic Acids Research, 1995, vol. 23, No. 20, pp. 4127-4133.
Lisitsyn et al., "Cloning the Differences Between Two Complex Genomes", Science, vol. 259, Feb. 12, 1993, pp. 946-951.
Tinsley et al., "Analysis of the Genetic Difference between *Neisseria meningitidis* and *Neisseria gonorrhoeae*: Two closely related Bacteria Expressing two Different Pathogenicities", Proc. Natl. Acad, Sci., USA, vol. 93, pp. 11109-11114, Oct. 1996 Microbiology.
Weiss, E et al, The immune system and infectious diseases, 1975, vol. 4, pp. 423-440 (abstract).
Moore, TD et al, Infection Immunity, vol. 63(4), pp. 1603-1607 Apr. 1995 (abstract).
Bautsch, W, FEMS Microbiology Lett., Mar. 1, 1993, vol. 107 (2-3), pp. 191-197.
Versalovic, J et al, Methods in Molecular and Cellular Biology, vol. 5(2), pp. 96-104, 1995.
Wolff, K. et al, FEMS microbiology leters, Jan. 15, 1995, vol. 125(2-3), pp. 255-263.
Martin, P.R. et al, accession No. M65216, created date in EMBL May 2, 1992.
Gaher, M. et al, Molecular Microbiology, Jan. 1996, vol. 19(2), pp. 249-259.
Dempsey, Jo Ann F. et al, Journal of Bacteriology, Apr. 1994, vol. 176(7).
Serizawa, H. et al, Nucleic Acids Research, vol. 15(3), pp. 1153-1163, 1987.
Welcher, Andrew A. et al, Nucleic Acids Research, vol. 14(24), pp. 10027-10044, Dec. 22, 1986.
Gaher, Martin et al, Molecular Microbiology, vol. 19(2), pp. 249-259, 1996.
Swanson, J. et al, Infection and Immunity, vol. 10(3), pp. 633-644, Sep. 1974.
deFilippis et al, Diagnostic Microbiology and Infectious Disease, vol. 51, pp. 85-90, 2005.
Tabrizi et al, Sex. Transm. Dis. 2005, vol. 32, pp. 199-202, labeled pp. 1-2.
Leters to the Editor, Antimicrobial Agenst and Chemotherapy, Apr. 2000, p. 116, vol. 44(4).
>*N. gonorrhoeae* MS11 supercont 1.5 of *Neisseria gonorrhoeae* (MS11) [DNA] >1-1582521 +, retrived from the BROAD Institute online on Apr. 24, 2012.

* cited by examiner

Fig. 9
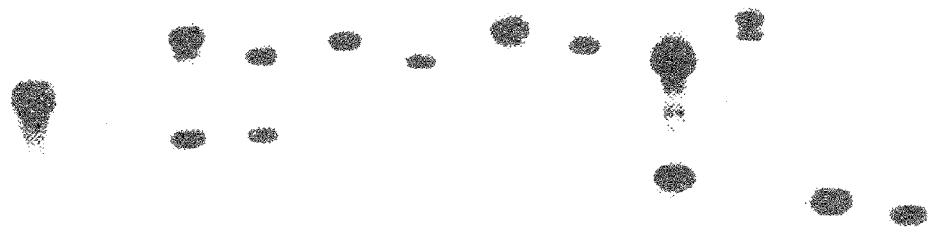
Fig. 10
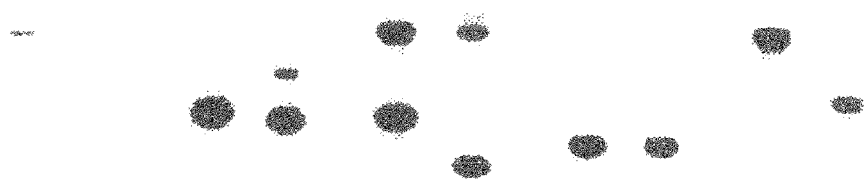
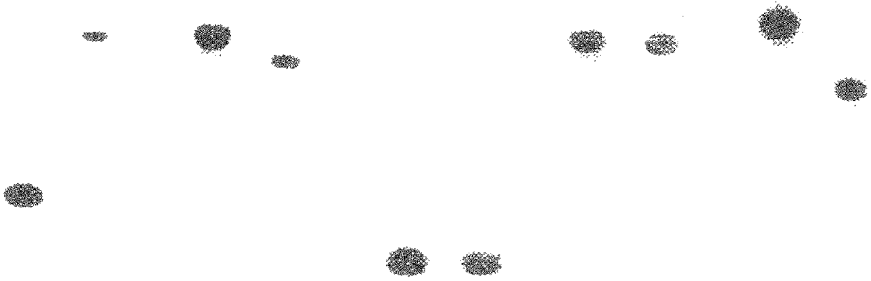

SEQUENCE LISTING

```
<160> NUMBER OF SEQ ID NOS: 99

<210> SEQ ID NO 1
<211> LENGTH: 257
<212> TYPE: DNA
<213> ORGANISM: Neisseria meningitides
<220> FEATURE:
<223> OTHER INFORMATION: Strain Z2491

<400> SEQUENCE: 1
gatccgctgc cggcagacga atatcaagac atcttcgatt ttatgaaaca gtatgacttg      60
tcttacccgt atgaatatct gcaggattgg atagattact atacgttcaa aaccgataag     120
ctggtatttg gtaacgcgaa gcgagagtga gccgtaaaac tctgagctcc tgttttatag     180
attacaactt taggccgtct taaagctgaa agattttcga aagctataaa ttgaagccct     240
tccacagtac atagatc                                                    257

<210> SEQ ID NO 2
<211> LENGTH: 276
<212> TYPE: DNA
<213> ORGANISM: Neisseria meningitidis
<220> FEATURE:
<223> OTHER INFORMATION: Strain Z2491

<400> SEQUENCE: 2
gatcatgttc aaatagatag gcatgggaag ctgcagctct aacgtccatg aaaatatgtt      60
gcatagctgc aagcggaacg cctttctttt catctacata atctatagag tcaaggcaac     120
cgctattgaa attagcagta ttgcctatga ttacattagt aatatgctca taccattttt     180
gggtggtcat catattgtgc cccattgtta tctccttata ttggttttag aaggaacttt     240
gacaggaaga ataacggcct tacctgtttg acgatc                               276

<210> SEQ ID NO 3
<211> LENGTH: 428
<212> TYPE: DNA
<213> ORGANISM: Neisseria meningitidis
<220> FEATURE:
<223> OTHER INFORMATION: Strain Z2491

<400> SEQUENCE: 3
```

```
gatctggtgg tgtttgcaca ggtaggcgca tacttgttcg ggactgagtt tgcggcggat      60
aagggtgtcg atgtgctgaa tcagctgcga atcgagctta tagggttgtc gcttacgctg     120
tttgatagtc cggctttgcc gctgggcttt tcggcgctg tattgctgcc cttgggtgcg     180
gtgccgtctg atttcgcggc tgatggtgct tttgtggcgg ttaagctgtt tggcgatttc     240
ggtgacggtg cagtggcggg acaggtattg gatgtggtat cgttcgcctt gggtcagttg     300
cgtgtagctc atggcaatct ttcttgcagg aaaggccgta tgctaccgca tactggcctt     360
tttctgttag ggaaagttgc acttcaaatg cgaatccgcc gacctctttc agttacagca     420
gcttgatc                                                              428

<210> SEQ ID NO 4
<211> LENGTH: 390
<212> TYPE: DNA
<213> ORGANISM: Neisseria meningitidis
<220> FEATURE:
<223> OTHER INFORMATION: Strain Z2491

<400> SEQUENCE: 4
gatcctgcat tgacatcggc cttggctgtc agggtattgt gaccggtaaa gtcggcatta      60
ccgttggcca ataaggatac atgaccgtct gcagaaacag catgaaggcc gtctgaaacg     120
atattgccct gcaatgcggt ggtttcgaga gccttggctg cgttcagctt ggtattgcga     180
agctgaatat tgcctttggc tgcctgaatg tgcagattac ccgagttggt acgcagattg     240
gtattggtaa cattcagcaa gcctgcctcc acccatgt cttttgaggc agtgagggtt     300
ttactggtgc cggtaatatg ggcagcgtta tccgatttca aatggatgct ggccggcaga     360
caaatcttta tcaacattca aattcagatc                                      390

<210> SEQ ID NO 5
<211> LENGTH: 177
<212> TYPE: DNA
<213> ORGANISM: Neisseria meningitidis
<220> FEATURE:
<223> OTHER INFORMATION: Strain Z2491

<400> SEQUENCE: 5
gatcagattg gtgaagacgg tattaccgtc aatgttgcag gccgttcggg atatacggcg      60
aaaatcgacg tgtctccgag taccgatttg gcggtttatg gccatattga agttgtacgg     120
ggtgcaacgg ggttgaccca atccaattca gagccgggtg gaaccgtcaa tttgatc        177

<210> SEQ ID NO 6
<211> LENGTH: 341
<212> TYPE: DNA
<213> ORGANISM: Neisseria meningitidis
<220> FEATURE:
<223> OTHER INFORMATION: Strain Z2491

<400> SEQUENCE: 6
gatcaatgat gctactattc aagcgggcag ttcgtgtac agctccacca aaggcgatac      60
tgaattgggt gaaaataccc gtattattgc tgaaaacgta accgtattat ctaacggtag     120
tattggcagt gctgctgtaa ttgaggctaa agacactgca cacattgaat cgggcaaacc     180
gctttcttta gaaacctcga ccgttgcctc caacatccgt ttgaacaacg gtaacattaa     240
aggcggaaag cagcttgctt tactggcaga cgataacatt actgccaaaa ctaccaatct     300
gaatactccc ggcaatctgt atgttcatac aggtaaagat c                         341
```

```
<210> SEQ ID NO 7
<211> LENGTH: 164
<212> TYPE: DNA
<213> ORGANISM: Neisseria meningitidis
<220> FEATURE:
<223> OTHER INFORMATION: Strain Z2491

<400> SEQUENCE: 7
gatccaactg tttgatttta ctggctgctt ctccatgcgc ggtattgacc aaagccgcaa      60
ggatattcgc ttccagattg tctttcaggc tgccgccgtt gacagcggta ttaatcagtg     120
cggcactgcc cgcattggct aggttgacgg tcaggttgtt gatc                      164

<210> SEQ ID NO 8
<211> LENGTH: 219
<212> TYPE: DNA
<213> ORGANISM: Neisseria meningitidis
<220> FEATURE:
<223> OTHER INFORMATION: Strain Z2491

<400> SEQUENCE: 8
gatcaatcac acatcttgtc attttttcga ttccttcatt tcggtttcta atgtttcaat      60
tcttgcggcc atttcctgaa tggctttagt caaaacgggg atgaacgctt cgtattcgac     120
ggtgtaggta tcgtttgttt tatttaccat cggcaatcga ccatattcat cttccagcgc     180
agcaatgtcc tgggcaataa accaatgccg caaccgatc                            219

<210> SEQ ID NO 9
<211> LENGTH: 356
<212> TYPE: DNA
<213> ORGANISM: Neisseria meningitidis
<220> FEATURE:
<223> OTHER INFORMATION: Strain Z2491

<400> SEQUENCE: 9
gatcttgggt aagcccccaa cctgcataga aaggcaggcc gtagcagctg acttttttgc      60
cgcgcaacaa ggcttcaaaa ccggtcagcg aagtcatggt atgtatttcg tctgcgtatt     120
ggagacaggt caggatgtcg gcttgttcgg cggtttggtc ggcatatcgt gcagcatcat     180
caggggaaat atggccgatg cggttaccgc tgactacatc gggatgcggt ttgtagatga     240
tataggcatt ggggtttcgt tcgcgtacgg tacggagcaa atccagattg cggtagattt     300
ggggcgaacc gtagcggata aacgcatcat cttcaacctg gccgggaacg aggatc        356

<210> SEQ ID NO 10
<211> LENGTH: 210
<212> TYPE: DNA
<213> ORGANISM: Neisseria meningitidis
<220> FEATURE:
<223> OTHER INFORMATION: Strain Z2491

<400> SEQUENCE: 10
gatccgcttt cagtttccgt accggtggca tcagtcaagt ccgttttgtg caccaaaccg      60
cgtccatatg aaacataaaa caaatcgctt aagcccaaag ggttatcgaa cgataaagcg     120
acatttcctt gatatttgcc ggtcgttttg ccgcccgcat catctatacc gatactgaac     180
cgtatgggtt tattctgctg ccatttgatc                                      210

<210> SEQ ID NO 11
<211> LENGTH: 259
<212> TYPE: DNA
<213> ORGANISM: Neisseria meningitidis
<220> FEATURE:
<223> OTHER INFORMATION: Strain Z2491
```

<400> SEQUENCE: 11

| gatcccgaaa cgcaattggt cgaaagctat atgctgaacg atgtgttgcg gttttgggac | 60 |
| --- | --- |
| agcgcaggtt tgggcgatgg gaaagaagcc gaccgcgccc atcggcaaaa actgattgat | 120 |
| gtcctgtcta aaacctatac tcattcggat gggcagtggg gctggataga tttggtgttc | 180 |
| gttatccttg acggcagctc ccgcgatttg ggtacggcct atgatttgtt gagggatgtt | 240 |
| atccttaaaa tgattgatc | 259 |

<210> SEQ ID NO 12
<211> LENGTH: 436
<212> TYPE: DNA
<213> ORGANISM: Neisseria meningitidis
<220> FEATURE:
<223> OTHER INFORMATION: Strain Z2491

<400> SEQUENCE: 12

| gatcaaatgg atgatttata tagaattttc ttttacgact gcgtgccgtt tgaaaagaaa | 60 |
| --- | --- |
| atgcacaatc ccgtatctca tcgtgccata gattttcaa agactccgga agccatattt | 120 |
| cgttgcaatc tgcataccga attgaagaag aagcgtaaat tagcgttacg tttaggcaag | 180 |
| ctgtcggaca atacagcatg gatattaaaa ccccaagtca tgaaaaatct tctgaaaaac | 240 |
| ccgtcaactc aaattacgga aaacgatgtc gtgctcgatg ttaaacaaaa aggtgtagat | 300 |
| atgcgtatag gcttggatat ttcatctatt accttaaaaa aacaagccga taaaatcatc | 360 |
| ttgttttctg gtgattccga ttttgtccca gcagccaaat tagccagacg ggaaggtatc | 420 |
| gattttattc ttgatc | 436 |

<210> SEQ ID NO 13
<211> LENGTH: 363
<212> TYPE: DNA
<213> ORGANISM: Neisseria meningitidis
<220> FEATURE:
<223> OTHER INFORMATION: Strain Z2491

<400> SEQUENCE: 13

| gatcgtttta cgtcgcaatc gagctttgtg gtgcgctcgc ctaaaagcca atcttctctc | 60 |
| --- | --- |
| aatggcctgg gtgccatttt gcagggcaca ggttttgccc gtgcgcaaga cgatatttat | 120 |
| accgtgcagg aatatatgca gtcgcgttcg gctttggatg cgttgcgtaa gaaaatgccc | 180 |
| attcgcgatt tttatgaaaa agaaggcgat attttcagcc gttttaatgg ttttggcctg | 240 |
| cgtggcgagg atgaggcgtt ttatcaatac taccgtgata aggtatccat ccattttgac | 300 |
| tctgtctcag gcatttccaa tttgagcgtt acatcgttta atgccggtga atctcaaaag | 360 |
| atc | 363 |

<210> SEQ ID NO 14
<211> LENGTH: 314
<212> TYPE: DNA
<213> ORGANISM: Neisseria meningitidis
<220> FEATURE:
<223> OTHER INFORMATION: Strain Z2491

<400> SEQUENCE: 14

| gatcttgcgt catttatatc ttcaccgata ttgcaattac cgccgttcca gttgaaataa | 60 |
| --- | --- |
| caacgactaa aattgtagtt cctaaaagaa tcattcctat tcttgcgtac catttcccaa | 120 |
| taattgcgcc cgacaatttc catttaatgc tccatcagtt cttttacttc cggaaatctg | 180 |
| ctgtaatctg acataagacg cataattgaa ctatcaacgc cgtaacagcc ataggtttta | 240 |

```
ataccgtttt cggcgtgttc ccaaatgcaa ttactgtatt cgtagccttt tacaaattta    300
tcggtttcgg gatc                                                      314

<210> SEQ ID NO 15
<211> LENGTH: 256
<212> TYPE: DNA
<213> ORGANISM: Neisseria meningitidis
<220> FEATURE:
<223> OTHER INFORMATION: Strain Z2491

<400> SEQUENCE: 15
gatcatacga atctacccta aaatacccg tcgccgattt aggattggct acataaagct      60
cattataagg gtattttgat gacatgatac ggttaaattc attgccgttg tttatcctga   120
ttctataaat tggttcaaca gcaaagcctc tggattccct taattgatta taatattgcc   180
tgtatgtttg tacatcatgt cttgtccacg gctctccagg agtcctcaga atagcaatcc   240
cgttaaattt cggatc                                                   256

<210> SEQ ID NO 16
<211> LENGTH: 235
<212> TYPE: DNA
<213> ORGANISM: Neisseria meningitidis
<220> FEATURE:
<223> OTHER INFORMATION: Strain Z2491

<400> SEQUENCE: 16
gatccacgcc tgtgcctacc ttggcttttt gttcgccaaa caaggcattt aaggttgagg    60
acttgccgac acctgtcgca ccgacaagca agacatccaa atgacggaaa ccggctgctg   120
tgactttttg cccgatttca gaaatacggt aacgatgcat atgcgctcct accagccaaa   180
aaaagaagca accgtgctaa tcgcccctcc aatcgctttt gcagcaccgc cgatc        235

<210> SEQ ID NO 17
<211> LENGTH: 259
<212> TYPE: DNA
<213> ORGANISM: Neisseria meningitidis
<220> FEATURE:
<223> OTHER INFORMATION: Strain Z2491

<400> SEQUENCE: 17
gatccaacgg gcatcgctgt ccttactcgg tgtggtttga ccgctgattt gtccttcttc    60
gtcaacttct atggcctgac gctgtttgct gccggcggtc tggataatgg tggcatcaac   120
gacggcggcg gatgctttct ctattttag gccttttcg gtcagttggc agttaatcag    180
tttgagtaat tcggacaggg tgtcgtcttg cgccagccag ttgcggtagc ggcataaggt   240
actgtaatcg gggatgatc                                                259

<210> SEQ ID NO 18
<211> LENGTH: 201
<212> TYPE: DNA
<213> ORGANISM: Neisseria meningitidis
<220> FEATURE:
<223> OTHER INFORMATION: Strain Z2491

<400> SEQUENCE: 18
gatctgtgcc gttgatttta tctttcagat gcagcatcga atatcggaaa gccaaatcag    60
caattctttt tgcatcgtgt ggattttgag acgggcctaa tgaccgtacc cgcttaataa   120
aaaatgcacc gtcaatcaaa atggcggttt tcatattgct tcccctatat ttgtcaaaga   180
tataaaaaag cccttgggat c                                             201
```

<210> SEQ ID NO 19
<211> LENGTH: 334
<212> TYPE: DNA
<213> ORGANISM: Neisseria meningitidis
<220> FEATURE:
<223> OTHER INFORMATION: Strain Z2491

<400> SEQUENCE: 19

| | | | | | |
|---|---|---|---|---|---|
| aattcaaagg | aggcatttgt | tgcaagaaaa | gtacaaagtg | atttgcaaaa | agcattgaat | 60 |
| gctagcaact | ataacaagca | gcaatatgca | agacgtgcgg | caacagcgtt | agagaatgct | 120 |
| tcaaaatcaa | aagttatggc | agcgaattct | ttttgatcta | tcttgtgcga | acgggtcaaa | 180 |
| tattcttcgt | acattgagtt | aatcgtacca | atcgccctaa | ccacattttc | atcagaaaat | 240 |
| atggaaataa | tagcatccct | atacgcacct | agtgtaatat | tgtttctatt | attagttata | 300 |
| gcattattcg | aatacataat | agcacctcca | aatt | | | 334 |

<210> SEQ ID NO 20
<211> LENGTH: 238
<212> TYPE: DNA
<213> ORGANISM: Neisseria meningitidis
<220> FEATURE:
<223> OTHER INFORMATION: Strain Z2491

<400> SEQUENCE: 20

| | | | | | |
|---|---|---|---|---|---|
| aattcctgcg | cacctttgcc | gatggggaga | taatcgcctt | tttgcagcat | tctgccctga | 60 |
| tggccgccga | aaccggcttt | caggtcggta | cttctcgaac | ccatcacttc | cggcacatca | 120 |
| aatccgcccg | ccacgcacac | atagccgtac | atgccctgca | cggcacgcac | cagtttcaag | 180 |
| gtctgccctt | tgcgggcggt | ataacgccaa | tacgaataga | ccggttcgcc | gtccaatt | 238 |

<210> SEQ ID NO 21
<211> LENGTH: 249
<212> TYPE: DNA
<213> ORGANISM: Neisseria meningitidis
<220> FEATURE:
<223> OTHER INFORMATION: Strain Z2491

<400> SEQUENCE: 21

| | | | | | |
|---|---|---|---|---|---|
| aattgggcga | gatgctgccg | gaaacggatt | taaaacagat | tgcggcggca | gtgttgaaga | 60 |
| cgaacgatga | ggcggcattg | cagaaggtgg | tgaaaacggc | caaaggcaat | gcgcggaaac | 120 |
| tgtcgaagct | gctgctgatt | gtggactatt | tgttgcaggt | taaccctgat | gttgatttgg | 180 |
| atgatgatgt | aatcgaacac | gcggaaacct | atttaatcca | ctaaacccttt | gacagataag | 240 |
| gcaataatt | | | | | | 249 |

<210> SEQ ID NO 22
<211> LENGTH: 212
<212> TYPE: DNA
<213> ORGANISM: Neisseria meningitidis
<220> FEATURE:
<223> OTHER INFORMATION: Strain Z2491

<400> SEQUENCE: 22

| | | | | | |
|---|---|---|---|---|---|
| aatttatgta | cggttttgcc | gtttgcagtc | agccagtcgg | caaggcgcag | aaaaaaatcg | 60 |
| ccgacagggc | cttgaagcag | caggatattt | tctgcgcttt | caagcaggtt | ttgcaggtta | 120 |
| tttttgagga | cggtctgttt | catgttgcaa | tgtggttttg | ttttttatgt | aatagtttta | 180 |
| ggttgaactt | tcaagcatac | gccaagagaa | tt | | | 212 |

<210> SEQ ID NO 23
<211> LENGTH: 227
<212> TYPE: DNA
<213> ORGANISM: Neisseria meningitidis
<220> FEATURE:
<223> OTHER INFORMATION: Strain Z2491

<400> SEQUENCE: 23

```
aattcagtgc ctgcgtcata tcacggctac cttgtggttc agggttactg tatcgcccgc     60
ggcatcgacg gcttcaatat gcagcttcag ccagccgtgc tgcggggcgg atgcggttac    120
ttggatggat tgggcgcgtt tggactgaat cacgggctgc aaggcttgct cggcgtactg    180
tttggccagt acttcgatgc gctttaaatg cttttggcgg cgcaatt                  227
```

<210> SEQ ID NO 24
<211> LENGTH: 167
<212> TYPE: DNA
<213> ORGANISM: Neisseria meningitidis
<220> FEATURE:
<223> OTHER INFORMATION: Strain Z2491

<400> SEQUENCE: 24

```
gatccaggac tcaaaaaccg atttcctaat agagtgtcta atatcccaat ctttttacc      60
ccctctgctg tagaattgat agagaaagtt tgtctatctt tttcatatac ccatgccttc    120
tttttatcat tgtagctaac ataaccgcca acaatgctt ctagatc                   167
```

<210> SEQ ID NO 25
<211> LENGTH: 251
<212> TYPE: DNA
<213> ORGANISM: Neisseria meningitidis
<220> FEATURE:
<223> OTHER INFORMATION: Strain Z2491

<400> SEQUENCE: 25

```
aattcttgcg gccatttcct gaatggcttt agtcaaaacg gggatgaacg tttcgtattc     60
gacggtgtag gtatcgtttg ttttatttac catcggcaat cgaccatatt catcttccag    120
cgcagcaatg tcctgggcaa taaaccaatg ccgcaaccga tcttctttat gactgccgtc    180
cttgattgga ttcgcccacc attcgcggac tttgtccgct cgttcatctg ccggcaagtc    240
tttgaataat t                                                         251
```

<210> SEQ ID NO 26
<211> LENGTH: 207
<212> TYPE: DNA
<213> ORGANISM: Neisseria meningitidis
<220> FEATURE:
<223> OTHER INFORMATION: Strain Z2491

<400> SEQUENCE: 26

```
aattcccgac tatcgcggat gcgtagtttt tgccggtggg caagagcagg tgtgggataa     60
gttaggtgat ttgcccgatg gcgtcagcct gaccccgcct gaatcggtaa atattgacgg    120
cttaaaatcc gtaaaactcg tcgcattaaa tgctgccgct caggcttta ttaacaagca    180
cgccggtatc gacagcgtac ctgaatt                                        207
```

<210> SEQ ID NO 27
<211> LENGTH: 379
<212> TYPE: DNA
<213> ORGANISM: Neisseria meningitidis
<220> FEATURE:
<223> OTHER INFORMATION: Strain Z2491

<400> SEQUENCE: 27

```
aattgtttgg gaataatcca aacaaacagc atcaggatag cggcggcggt caggctgcct      60
gaaaggattt tgccggggtt ttttgtaggc aaagcggacg agaaaccaaa gcaacagcag     120
catggtgtcc caatagccga ttgagaatag gatggccaaa ccttctagga aatggcgtaa     180
atcgtttgtg gtaaccatgg gtagttcctg tggttaaatg tgcaggctgc ttttgccga     240 accttgccgc atctcaaaag cagcctgcgc ttcagcgttg cgttacgcag taaaataatg     300
aatatttgta acggcttggg tatttttgt caatattccc gcccttccct taacagctgc     360
cgcgctttcc gttaaaatt                                                  379
```

<210> SEQ ID NO 28
<211> LENGTH: 274
<212> TYPE: DNA
<213> ORGANISM: Neisseria meningitidis
<220> FEATURE:
<223> OTHER INFORMATION: Strain Z2491

<400> SEQUENCE: 28

```
aattcgccga aatcaggctg ctgctcgata atcggcgcgg ccgattggcg ttgtgcctcg      60
attaaatcca tcttgtcttg cagacgtttg gcctggcctt tgcggcggcg ttcggccagt     120
tgttccatcc gcgttccgc aaatgccgcc cgtttgttgc cgttgaatac cgctttgcaa     180
atcaccttgc cctgcatatc cttcacaatc acatggtcgg catcgtggat gtcgtaagcc     240
acccgtacct tctgaccgct gtaatccagc aatt                                 274
```

<210> SEQ ID NO 29
<211> LENGTH: 263
<212> TYPE: DNA
<213> ORGANISM: Neisseria meningitidis
<220> FEATURE:
<223> OTHER INFORMATION: Strain Z2491

<400> SEQUENCE: 29

```
aattccgttc ttattgggct ttttccatcc atcgggtatg cctgaaggga acgcaaaccc      60
tgccacttgc ccatcgctcc attcccgcat tagcgcgtct gacggcaagt gttctcgcgc     120
ccaatcaagc cacgcctgcc gcattgcggc cttgtcctgc tgaaaacttc gcagtgcttt     180
tgcaaccggc ccatcattaa cttcaatcaa ataaatcatt atatttgcgt tcattttcc      240 tacaccttcg ccacatccaa att                                             263
```

<210> SEQ ID NO 30
<211> LENGTH: 316
<212> TYPE: DNA
<213> ORGANISM: Neisseria meningitidis
<220> FEATURE:
<223> OTHER INFORMATION: Strain Z2491

<400> SEQUENCE: 30

```
aattgttcaa gaaaaagtc ggcacggcgc ggcaacgggg aaaatgcgtt gacgccgtct       60
ttttctaagg tgatgtagta ggggcggaaa tagccttctt caaacgccca gaaactggct     120
tggttttcgt ttgcaatgcg ttttgcaatg acgtgataag ggcgtgtgtc gccaaagcag     180
acaacggcct ggatgtgatg ttgagtgatg tattcttgca aaaactcagg aaaggcgtcg     240
tagttgtcgt taaaaacaac ggtatgcgct tgagtgggcg ataaaaata gtcgtcgcct     300 gcattaaagt tgaatt                                                     316
```

<210> SEQ ID NO 31
<211> LENGTH: 324

```
<212> TYPE: DNA
<213> ORGANISM: Neisseria meningitidis
<220> FEATURE:
<223> OTHER INFORMATION: Strain Z2491

<400> SEQUENCE: 31
aattcaatca acggaaaaca catcagcatc aaaaacaacg gtggtaatgc cgacttaaaa      60
aaccttaacg tccatgccaa aagcggggca ttgaacattc attccgaccg ggcattgagc    120
atagaaaata ccaagctgga gtctacccat aatacgcatc ttaatgcaca acacgagcgg    180
gtaacgctca accaagtaga tgcctacgca caccgtcatc taagcattac cggcagccag    240
atttggcaaa acgacaaact gccttctgcc aacaagctgg tggctaacgg tgtattggca    300
ctcaatgcgc gctattccca aatt                                           324

<210> SEQ ID NO 32
<211> LENGTH: 230
<212> TYPE: DNA
<213> ORGANISM: Neisseria meningitidis
<220> FEATURE:
<223> OTHER INFORMATION: Strain Z2491

<400> SEQUENCE: 32
aattatgcaa aaaacgcaa cgccgaaaaa ctggcaccgc gcggatattg ttgctgcttt       60 gaaaagaaa ggctggtcac ttcgagcact ttcaatagaa gcggggttgt cgccgaatac     120
gcttagaagc gcactggccg cccttatct aagggagaa aggattattg ccgctgcaat     180
cggagtggaa ccggaagaga tttggtccga acggtatgca gatcggaatt                230

<210> SEQ ID NO 33
<211> LENGTH: 249
<212> TYPE: DNA
<213> ORGANISM: Neisseria meningitidis
<220> FEATURE:
<223> OTHER INFORMATION: Strain Z2491

<400> SEQUENCE: 33
aatttaatcg gtggaatgcc tgttcaaccg caccaatccc gctgaatacg gttgctaatc      60
taatatgtga atcaggttta agaaaagttt tagatttcca accttgttga ctgggaaaga    120
gcaaagtttt ttgtaatcga gtatcgtgtg tctgtgccat tgtcgaaata gtcatactta    180
tatcgttctg tttatcttat caatatgaaa actacatcgt tgattgccct gacaatgcct    240
tggtcaatt                                                            249

<210> SEQ ID NO 34
<211> LENGTH: 343
<212> TYPE: DNA
<213> ORGANISM: Neisseria meningitidis
<220> FEATURE:
<223> OTHER INFORMATION: Strain Z2491

<400> SEQUENCE: 34
aattcttgtc ccggagtcca acgtatattt accctcctgc gagctaaaag actattattc      60
tccactgcca cagtagccgc attcaccgcc gtattcacat cccctttaac caatgccact    120
gcgctgcctg cgataatctg cgagtaggct atgactttt ggcgttcttg gggtgacagt     180
ttgcctacat cgcgtccgtc caacagggtt tctcccacca tctcgccgac tgccgcgccg    240
attgcgccgt cccgacattt gccttattt gctaccgccg atgcacagcc tgctacggca    300
tgggctatct tgtgggcaat gtagtcttcg ctgagattaa att                       343
```

```
<210> SEQ ID NO 35
<211> LENGTH: 184
<212> TYPE: DNA
<213> ORGANISM: Neisseria meningitidis
<220> FEATURE:
<223> OTHER INFORMATION: Strain Z2491

<400> SEQUENCE: 35
aattcttcaa acatcgtttc gataatcggg tcggtgtaca cactgatgcg gtcgcccgca      60
cggctttgac cggctcggaa aatataggcg gtggctttgc cgtcggcgat gtcgacgcac     120
caacgccaga tggcgtcttc ggtattcaaa caatcacccg cacagctttc acctgcgcgg     180
aatt                                                                  184

<210> SEQ ID NO 36
<211> LENGTH: 15620
<212> TYPE: DNA
<213> ORGANISM: Neisseria meningitidis
<220> FEATURE:
<223> OTHER INFORMATION: Strain Z2491

<400> SEQUENCE: 36
tatgctcaat ctcattttca aaatgcaaaa cttttctgat ttttcctact ttttgctcaa      60
tattaggaag gttttaggca attgaaaatt ttttggcgca ttttatgcg tcaaatttcg      120 ttaacagact attttttgcaa aggtctccgt ctgtaaaagc aaggataggg catctgccct    180
tttgattgtt tgattaacga tacaaggagt ttcaaaatga gagttttata gtggattaac    240
aaaaaccagt acagcgttgc ctcgccttgc cgtactattt gtactgtctg cggcttcgtc    300
gccttgtcct gatttaaatt taatccacta tatgtgttca tgaaatgact tgggtcggag    360
gctcaggtaa tgcgcaacaa agttcatatt attgcgaaat ttgcgaatct gcagggctta    420
acgatacggg aaatcctgat aaatctttag gattgccaaa caatacgttc agtaatccgc    480
ctggttgggg agctacaatc ggagctttag caggtagccg cataggtatg cctgaatttg    540
gtacgtttgc gagccatgcc attgaaaatt tcgactggtc atggtatcga cgttataggg    600
aaattgccga aacgattgaa cgagaatatt caggcggttt gccttaatag ttgaggaggt    660
catgatgttt gccaaacatt atcaattcat cgcactcggc atcatgctgc ttctttatat    720
gttgattctc tatacgaccg attttttccaa tctgacgtat tggatgctgt ttttttatctg   780 ttttattaca ggaaaaatat tagctcgttt gttagagaaa gctttaaat aaaatagcag     840 ctagtcgcaa aaggtcgtct gaaacctttt caggcggcct ttctaaaata catccaactt    900
cctaatccct atttttcaaa aaggaaatct atgccccatc tgcaaaacct gtctttgggc    960
ttaaagaaaa agctgcctgt tatcctgcaa acagaaatat cagaatgcgg cttggcatgt   1020
ctggcggctg tggcgggatt tcatggtttc catacgaatt tacgcgcact gcgttcaaaa   1080
tactgtccga gacctttgca aaattcccca aaatccccta aatgtcttgg tgggaatttt    1140
ggggaatttt gcaaaggtct cattctataa ctgtaaaatac ttttaaattt atgacaaaat   1200
agtaaatatt gctaaaataa tattgatgtc atgaaatttt ttcctgctcc atgtctgttg   1260
gttatcctgg ctgtcatacc ccttaaaacc ttagctgccg atgaaaacga tgcagaactt   1320
atccgttcca tgcagcgtca gcagcacata gatgctgaat tgttaactga tgcaaatgtc   1380
cgtttcgagc aaccattgga gaagaacaat tatgtcctga gtgaagatga aacaccgtgt   1440
actcgggtaa attacattag tttagatgat aagacggcgc gcaaatttc ttttcttcct    1500 tctgtgctca tgaaagaaac agcttttaaa actgggatgt gtttaggttc caataatttg   1560
agcaggctac aaaaagccgc gcaacagata ctgattgtgc gtggctacct cacttcccaa   1620
```

```
gctattatcc aaccacagaa tatggattcg ggaattctga aattacgggt atcagcaggc    1680 gaaataggg atatccgcta tgaagaaaaa cgggatggga agtctgccga gggcagtatt    1740
agtgcattca ataacaaatt tcccttatat aggaacaaaa ttctcaatct cgcgatgta    1800 gagcagggct tggaaaacct gcgtcgtttg ccgagtgtta aaacagatat tcagattata    1860
ccgtccgaag aagaaggcaa aagcgattta cagatcaaat ggcagcagaa taaacccata    1920
cggttcagta tcggtataga tgatgcgggc ggcaaaacga ccggcaaata tcaaggaaat    1980
gtcgctttat cgttcgataa ccctttgggc ttaagcgatt tgttttatgt ttcatatgga    2040
cgcggtttgg tgcacaaaac ggacttgact gatgccaccg gtacgaaaac tgaaagcgga    2100
tccagaagtt acagcgtgca ttattcggtg cccgtaaaaa aatggctgtt ttcttttaat    2160
cacaatggac atcgttacca cgaagcaacc gaaggctatt ccgtcaatta cgattacaac    2220
ggcaaacaat atcagagcag cctggccgcc gagcgcatgc tttggcgtaa caggtttcat    2280
aaaacttcag tcggaatgaa attatggaca cgccaaacct ataaatacat cgacgatgcc    2340
gaaatcgaag tgcaacgccg ccgctctgca ggctgggaag ccgaattgcg ccaccgtgct    2400
tacctcaacc gttggcagct tgacggcaag ttgtcttaca aacgcgggac cggcatgcgc    2460
caaagtatgc ccgcacctga agaaaacggc ggcggtacta ttccaggcac atcccgtatg    2520
aaaatcataa ccgccggatt ggatgcagcg gccccgttta tgttgggcaa acagcagttt    2580
ttctacgcaa ccgccattca agctcaatgg aacaaaacgc ctttggttgc caagacaag    2640 ttgtctatcg gcagccgcta caccgttcgc ggatttgatg gggagcagag tcttttcgga    2700
gagcgaggtt tctactggca gaatacttta acttggtatt tcatccgaa ccatcagttc    2760 tatctcggtg cggactatgg ccgcgtatct ggcgaaagtg cacaatatgt atcgggcaag    2820
cagctgatgg gtgcagtggt cggcttcaga ggagggcata agtaggcgg tatgtttgct    2880 tatgatctgt ttgccggcaa gccgcttcat aaacccaaag gctttcagac gaccaacacc    2940
gtttacggct tcaacttgaa ttacagtttc taacctctga attttttac tgatattag    3000 acggtcttc cttatcctca gactgtcaaa ctttacctac gtacttggcg cgcagtacgt    3060
tcatcttcaa aatggaatag acatgaataa aggtttacat cgcattatct ttagtaaaaa    3120
gcacagcacc atggttgcag tagccgaaac tgccaacagc cagggcaaag gtaaacaggc    3180
aggcagttcg gtttctgttt cactgaaaac ttcaggcgac ctttgcggca aactcaaaac    3240
cacccttaaa accttggtct gctctttggt ttccctgagt atggtattgc ctgcccatgc    3300
ccaaattacc accgacaaat cagcacctaa aaaccagcag gtcgttatcc ttaaaaccaa    3360
cactggtgcc cccttggtga atatccaaac tccgaatgga cgcggattga gccacaaccg    3420
ctatacgcag tttgatgttg acaacaaagg ggcagtgtta aacaacgacc gtaacaataa    3480 tccgttctg gtcaaaggca gtgcgcaatt gattttgaac gaggtacgcg gtacggctag    3540
caaactcaac ggcatcgtta ccgtaggcgg tcaaaaggcc gacgtgatta ttgccaaccc    3600
caacggcatt accgttaatg gcggcggctt taaaaatgtc ggtcggggca tcttaactat    3660
cggtgcgccc caaatcggca aagacggtgc actgacagga tttgatgtgc gtcaaggcac    3720
attgaccgta ggagcagcag gttggaatga taaggcgga gccgactaca ccggggtact    3780
tgctcgtgca gttgctttgc aggggaaatt acagggtaaa aacctggcgg tttctaccgg    3840
tcctcagaaa gtagattacg ccagcggcga atcagtgca ggtacggcag cgggtacgaa    3900
accgactatt gcccttgata ctgccgcact gggcggtatg tacgccgaca gcatcacact    3960
gattgccaat gaaaaaggcg taggcgtcaa aaatgccggc acactcgaag cggccaagca    4020
```

```
attgattgtg acttcgtcag gccgcattga aaacagcggc cgcatcgcca ccactgccga   4080
cggcaccgaa gcttcaccga cttatctctc catcgaaacc accgaaaaag gagcggcagg   4140
cacatttatc tccaatggtg gtcggatcga gagcaaaggc ttattggtta ttgagacggg   4200
agaagatatc agcttgcgta acggagccgt ggtgcagaat aacggcagtc gcccagctac   4260
cacggtatta aatgctggtc ataatttggt gattgagagt aaaactaatg tgaacaatgc   4320
caaaggctcg gctaatctgt cggccggcgg tcgtactacg atcaatgatg ctactattca   4380
agcgggcagt tccgtgtaca gctccaccaa aggcgatact gaattgggtg aaaatacccg   4440
tattattgct gaaaacgtaa ccgtattatc taacggtagt attggcagtg ctgctgtaat   4500
tgaggctaaa gacactgcac acattgaatc gggcaaaccg ctttctttag aaacctcgac   4560
cgttgcctcc aacatccgtt tgaacaacgg taacattaaa ggcggaaagc agcttgcttt   4620
actggcagac gataacatta ctgccaaaac taccaatctg aatactcccg gcaatctgta   4680
tgttcataca ggtaaagatc tgaatttgaa tgttgataaa gatttgtctg ccgccagcat   4740
ccatttgaaa tcggataacg ctgcccatat taccggcacc agtaaaaccc tcactgcctc   4800
aaaagacatg ggtgtggagg caggcttgct gaatgttacc aataccaatc tgcgtaccaa   4860
ctcgggtaat ctgcacattc aggcagccaa aggcaatatt cagcttcgca ataccaagct   4920
gaacgcagcc aaggctctcg aaaccaccgc attgcagggc aatatcgttt cagacggcct   4980
tcatgctgtt tctgcagacg gtcatgtatc cttattggcc aacggtaatg ccgactttac   5040
cggtcacaat accctgacag ccaaggccga tgtcaatgca ggatcggttg gtaaaggccg   5100
tctgaaagca gacaatacca atatcacttc atcttcagga gatattacgt tggttgccgg   5160
caacggtatt cagcttggtg acggaaaaca acgcaattca atcaacggaa acacacatcag   5220 catcaaaaac aacggtggta atgccgactt aaaaaacctt aacgtccatg ccaaaagcgg   5280
ggcattgaac attcattccg accgggcatt gagcatagaa aataccaagc tggagtctac   5340
ccataatacg catcttaatg cacaacacga gcgggtaacg ctcaaccaag tagatgccta   5400
cgcacaccgt catctaagca ttaccggcag ccagatttgg caaaacgaca aactgccttc   5460
tgccaacaag ctggtggcta acggtgtatt ggcactcaat gcgcgctatt cccaaattgc   5520
cgacaacacc acgctgagag cgggtgcaat caaccttact gccggtaccg ccctagtcaa   5580
gcgcggcaac atcaattgga gtaccgtttc gaccaagact ttggaagata atgccgaatt   5640
aaaaccattg gccggacggc tgaatattga agcaggtagc ggcacattaa ccatcgaacc   5700
tgccaaccgc atcagtgcgc ataccgacct gagcatcaaa acaggcggaa aattgctgtt   5760
gtctgcaaaa ggaggaaatg caggtgcgcc tagtgctcaa gtttcctcat tggaagcaaa   5820
aggcaatatc cgtctggtta caggagaaac agatttaaga ggttctaaaa ttacagccgg   5880
taaaaacttg gttgtcgcca ccaccaaagg caagttgaat atcgaagccg taaacaactc   5940
attcagcaat tattttccta cacaaaaagc ggctgaactc aaccaaaaat ccaaagaatt   6000
ggaacagcag attgcgcagt tgaaaaaaag ctcgcctaaa agcaagctga ttccaaccct   6060
gcaagaagaa cgcgaccgtc tcgctttcta tattcaagcc atcaacaagg aagttaaagg   6120
taaaaacccc aaaggcaaag aatacctgca agccaagctt tctgcacaaa atattgactt   6180
gatttccgca caaggcatcg aaatcagcgg ttccgatatt accgcttcca aaaaactgaa   6240
ccttcacgcc gcaggcgtat tgccaaaggc agcagattca gaggcggctg ctattctgat   6300
tgacggcata accgaccaat atgaaattgg caagcccacc tacaagagtc actacgacaa   6360
agctgctctg aacaagcctt cacgtttgac cggacgtacg ggggtaagta ttcatgcagc   6420
```

```
tgcggcactc gatgatgcac gtattattat cggtgcatcc gaaatcaaag ctccctcagg    6480
cagcatagac atcaaagccc atagtgatat tgtactggag gctggacaaa acgatgccta    6540
taccttctta aaaccaaag gtaaaagcgg caaaatcatc agaaaaacca agtttaccag     6600
cacccgcgac cacctgatta tgccagcccc cgtcgagctg accgccaacg gtatcacgct    6660
tcaggcaggc ggcaacatcg aagctaatac cacccgcttc aatgccctg caggtaaagt     6720 taccctggtt gcgggtgaag agctgcaact gctggcagaa gaaggcatcc acaagcacga    6780
gttggatgtc caaaaagcc gccgctttat cggcatcaag gtaggtaaga gcaattacag     6840
taaaaacgaa ctgaacgaaa ccaaattgcc tgtccgcgtc gtcgcccaaa ctgcagccac    6900
ccgttcaggc tgggataccg tgctcgaagg taccgaattc aaaaccacgc tggccggtgc    6960
cgacattcag gcaggtgtag cgaaaaagc ccgtgtcgat gcgaaaatta tcctcaaagg     7020
cattgtgaac cgtatccagt cggaagaaaa attagaaacc aactcaaccg tatggcagaa    7080
acaggccgga cgcggcagca ctatcgaaac gctaaaactg cccagcttcg aaagccctac    7140
tccgcccaaa ttgtccgcac ccggcggcta tatcgtcgac attccgaaag gcaatctgaa    7200
aaccgaaatc gaaaagctgt ccaaacagcc cgagtatgcc tatctgaaac agctccaagt    7260
agcgaaaaac atcaactgga atcaggtgca gcttgcttac gacagatggg actacaaaca    7320
ggagggctta accgaagcag gtgcggcgat tatcgcactg gccgttaccg tggtcacctc    7380
aggcgcagga accggagccg tattgggatt aaacggtgcg gccgccgccg caaccgatgc    7440
agcattcgcc tctttggcca gccaggcttc cgtatcgttc atcaacaaca aaggcgatgt    7500
cggcaaaacc ctgaaagagc tgggcagaag cagcacggtg aaaaatctgg tggttgccgc    7560
cgctaccgca ggcgtagccg acaaaatcgg cgcttcggca ctgaacaatg tcagcgataa    7620
gcagtggatc aacaacctga ccgtcaacct agccaatgcg ggcagtgccg cactgattaa    7680
taccgctgtc aacggcggca gcctgaaaga caatctggaa gcgaatatcc ttgcggcttt    7740
ggtcaatacc gcgcatggag aagcagccag taaaatcaaa cagttggatc agcactacat    7800
agtccacaag attgcccatg ccatagcggg ctgtgcggca gcggcggcga ataagggcaa    7860
gtgtcaggat ggtgcgatag gtgcggctgt gggcgagata gtcggggagg ctttgacaaa    7920
cggcaaaaat cctgacactt tgacagctaa agaacgcgaa cagattttgg catacagcaa    7980
actggttgcc ggtacggtaa gcggtgtggt cggcggcgat gtaaatgcgg cggcgaatgc    8040
ggctgaggta gcggtgaaaa ataatcagct tagcgacaaa gagggtagag aatttgataa    8100
cgaaatgact gcatgcgcca aacagaataa tcctcaactg tgcagaaaaa atactgtaaa    8160
aaagtatcaa aatgttgctg ataaaagact tgctgcttcg attgcaatat gtacggatat    8220
atcccgtagt actgaatgta aacaatcag aaaacaacat ttgatcgata gtagaagcct     8280
tcattcatct tgggaagcag gtctaattgg taaagatgat gaatggtata aattattcag    8340
caaatcttac acccaagcag atttggcttt acagtcttat catttgaata ctgctgctaa    8400
atcttggctt caatcgggca atacaaagcc tttatccgaa tggatgtccg accaaggtta    8460
tacacttatt tcaggagtta atcctagatt cattccaata ccaagagggt ttgtaaaaca    8520
aaatacacct attactaatg tcaaataccc ggaaggcatc agtttcgata caaacctaaa    8580
aagacatctg gcaaatgctg atggtttag tcaagaacag ggcattaaag gagcccataa     8640
ccgcaccaat tttatggcag aactaaattc acgaggagga cgcgtaaaat ctgaaaccca    8700
aactgatatt gaaggcatta cccgaattaa atatgagatt cctacactag acaggacagg    8760
taaacctgat ggtggattta aggaaatttc aagtatataaa actgtttata tcctaaaaaa    8820
```

```
attttctgat gataaaatac ttcaaatggc tcaaaatgct gcttcacaag gatattcaaa    8880
agcctctaaa attgctcaaa atgaaagaac taaatcaata tcggaaagaa aaaatgtcat    8940
tcaattctca gaaacctttg acggaatcaa atttagatca tattttgatg taaatacagg    9000
aagaattaca aacattcacc cagaataatt taaaggaaaa attatgaaaa ataatatttt    9060
tctaaactta aataaaaaat ctataaataa caaccatttt gttatttcga ttttttttga    9120
aacaatttac caatttgaaa ctaaagatac gcttttagag tgttttaaaa atattacaac    9180
taccggacat tttggagtaa taggtgctca atatgaaaaa atagatgcta ccagatggat    9240
tggagattat gaagaggtaa atggatttga gtatattgat aaagctcctt ctatttattt    9300
ttcagttgga gatgatttca atcctgaaga attaattata cctattaatt tagcatatca    9360
ttactttaat attgcaatat ctgatttctt aatagctcac cctgaatatc aaaaaaagtg    9420
taaagaaata caaaaaacat attctcaaac aaactgtagc ctgcatgaaa cctaaaatcc    9480
atgcgtaagg tgtgtgcttc agcacgcacg cgttccatga tttacggctc aatgccgtct    9540
gaaaagctca aattttttca gacggcattt gttatgcaag taaatattca gattccctat    9600
atactgccca gacgcgtgcg tgctgaagac acccctacg cttgctgcag aactttcggg    9660
taaaaccggt gtgagcatta gcgcaccgta tgccaatgag aacagtcgca tcctgctcag    9720
caccacggat atcagttcgg aaaacggcaa aatcaaaatt caatcttacg gtgaccaata    9780
ttactatgcg agacagagcg aactctatac ctttgaacgc cgcagctaca aaactggcaa    9840
atggtacaac cgcaaacaca ttaccgaagt caaagaacac aaaaacgcca gcccgacgc     9900 agtaaacctc agcgcatccc aaggcatcga catcaaatct ggtggcagca tcgacgccta    9960
cgccaccgca ttcgatgccc ccaaaggcag cattaacatc gaagccgggc ggaaattgac   10020
actctatgcc gtagaagagc tcaactacga caaactagac agccaaaaaa ggcgcagatt   10080
tctcggcatc agctacagca aagcacacga caccaccacc caagtcatga aaaccgcgct   10140
gccctcaagg gtagttgcag aatcagccaa cctccaatcg ggctgggata ccaaactgca   10200
aggcacacag tttgaaacca cactgggtgg cgcaaccata cgcgcaggcg taggtgagca   10260
ggcacgggca gatgccaaga ttatcctcga agggatcaaa agcagcatcc acacagaaac   10320
cgtgagcagc agcaaatcta ctctatggca aaaacaggca ggacggggca gtaacatcga   10380
aaccttgcaa ttgccgagtt tcaccggtcc cgttgcgccc gtactgtccg cacccggcgg   10440
ttacattgtc gacattccga aaggcaatct gaaaacccaa atcgaaaccc tcaccaagca   10500
gcccgagtat gcttatttga aacaacttca agttgcgaaa aacatcaact ggaatcaggt   10560
gcagcttgct tacgataaat gggactacaa acaggagggc atgacacccg cagcagcagc   10620
tgtcgtcgtt atcgtcgtaa ccgtattgac ctacggtgca ctgtccgccc cggcagccgc   10680
cggaacggcg ggcgcggcag gcgcaggagc gggaggagcc gcagcaggaa cggcagccgg   10740
aactggagta gcagcaggaa cggcagccac aaccggagta gcagcaggca catcagctgc   10800
agctatcacc acagccgcag gcaaagccgc actggccagt ctcgccagcc aagccgcagt   10860
ttccctcatc aacaacaaag gagacataaa ccatacccctg aaagaactgg gcaaaagcag   10920
caccgtcaga caggccgcca ccgccgccgt aaccgcaggc gtactgcagg cataagcgg    10980 gctgaacacc caagcagccg aagccgtcag caaacatttt cacagtcccg cagcaggcaa   11040
actgaccgct aacctgatca acagcaccgc tgccgcaagt gtccataccg ccatcaacgg   11100 cggcagcctaa aagacaact tgggcgatgc cgcactgggt gcgatagtca gtaccgtaca   11160
cggagaagta gcgagcaaaa tcaaatttaa tctcagcgaa gactacattg cccacaagat   11220
```

```
agcccatgcc gtagcaggct gtgcatcggc ggtagcaaat aaaggcaaat gtcgggacgg   11280
cgcaatcggc gcggcagtcg gcgagatggt gggagaaacc ctgttggacg gacgcgatgt   11340
aggcaaactg tcacccccaag aacgccaaaa agtcatagcc tactcgcaga ttatcgcagg   11400
cagcgcagtg gcattggtta aggggatgt gaatacggcg gtgaatgcgg ctactgtggc   11460
agtggagaat aatagtcttt tagctcgcag gagggtaaat atacgttgga ctccgcgaca   11520
agaattggaa catgaatatg ccattcttga aatccaggcc attaccaatc aaatccgaag   11580
gctggatccg aaatttaacg ggattgctat tctgaggact cctggagagc cgtggacaag   11640
acatgatgta caaacataca ggcaatatta aatcaatta agggaatcca gaggctttgc   11700
tgttgaacca atttatagaa tcaggataaa caacggcaat gaatttaacc gtatcatgtc   11760
atcaaaatac ccttataatg agctttatgt agccaatcct aaatcggcga cggggtattt   11820
tagggtagat tcgtatgatc ctgcgacaag ggaaattatt tcaagaaaat ttacccaatt   11880
ttctcaaatc caagaaagta cggggattgg ttatatcaag gaggctgtta gaaaatatag   11940
ccctggtact gtcatttcca atgttccaag tacacctact acgataagag gaagaaagct   12000
tgaaggaaaa cttattttag aagttcctgc tcaggtcaat ccaattccac aatctgtatt   12060
aagggcggca caagaagaaa atgttatcat tagagataca acaggaagga tttacaaatg   12120
aagaaagata ttttttattg tgagcagtgg tcttatggtt ataagagact tcataagcct   12180
ttttctgaga acaagctga ggaaaaacat cttaaagggg agttatatac tgccgtaata   12240
ggttcggcga cacaacctga atatgtaatt accttgcgag aggaagtagg tttttttcg    12300 gtaaattttt tcgataaatt tggaagggat tatttaaccc atcaatttca aaaatattcc   12360
aattcgaatt attattttct ttctatggct gtatggagag attatataac tttggaatct   12420
catgacttag cagaaggata tacttatttc ttcaatgaaa atacggatga ttgctatgtt   12480
ttgaaacaag atttttattaa taatgagcga tatgaaaaaa cagaattata ttcccaaaaa   12540
gataaggtaa ttctatttcc aaagtttggt gaatatgatt tggtgttaaa tccggacatt   12600
atttaattaa gttttaaggc cgtctgaaaa aaatttcaaa cggcttttat tattgggttt   12660
ggaatctgag gataaagctg ataaaaacca ggaaattatc agattgctat atacgtattg   12720
ttgtacagac taaaggcagc aatcaaatca ctattgctta cccacaaaaa taaattgatt   12780
atatggaata atcatgaata agagaatgaa aatgtgtcct gcttgtcaac aaggctatct   12840
ctaccattcg aaacctaaat atcttcatga tgaaattatt ctgtgtgatg aatgcgatgc   12900
agtatggctc aaaggtatga atatatttta tggagaatat gaaaaagatt tttattctta   12960
tgttcctttc atggaatccc aaggtataac gagtgaatgt atttgggaag gagatttgtt   13020
tgatcatcca tattatgaag atgaaaactc aaatgatatg gattgatgga aattttaagc   13080
ctgcgtaggt acgattagcc atcaaacggc gtaatcatac gcaagattat caacagagag   13140
ggctggcagc gatataccac ccacaagatt gcccatgcca tagcgggctg tgcggcagcg   13200
gcggcgaata agggcaagtg tcaggatggt gcgataggcg ctgcagtcgg tgagattgtt   13260
ggtgaggctt tggttaagaa tactgatttc agtcgtatga gtgcgaccga aatcgaaaaa   13320
gctaaagcga agattactgc ctattcaaaa ctggttgccg gcactgcgtc tgccgttgta   13380
ggcggggatg tgaatacagc ggcgaatgcg gcacagatag cggtggagaa taatactttg   13440
tatcctagat gcgttggtgc aaagtgtgat gaatttcaaa aggaacaaca aaaatggata   13500
cgtgaaaatc ctgaagaata tcgagaagtt ttgcttttt agacaggatt tattccaatt   13560
atcggtgata tacagagttt tgtacaagca cagaccgctg ccgatcacct gtttgctttg   13620
```

```
ctgggtgtgg ttccgggtat cggtgaatcg atacaggcct ataaagtagc gaaagcggca    13680
aaaaatttac aaggcatgaa aaagccttg  gacaaggcag caaccgttgc cactgcacag    13740
ggctatgtca gcaaaaccaa aatcaaaatc ggtcaaactg aattaagggt tactgcagca    13800
actgacaaac aattgctgaa agctattggc gaaggaaggg acacgacagg taaaatgacc    13860
gagcagttat ttgactcttt agctaaacaa aatggcttca gagtgctttc gggcggcaaa    13920
tacggcggaa ataacggttt tgatcatgta tggcaggctg ccgatggtag tgtcgttttg    13980
attgtagaaa gtaagcagat taggaacggt acggtacagc tgaatccgaa tggtgcgggt    14040
ggatatacgc aaatgagtga ggattggatt agacaagttt tagatcaatt acccgatggt    14100
agtcccgcta agctgctgt  cttcaaagca aataagaacg gcacattaaa acagcaata     14160
gcaggcgttg atcgtcaaac aggtaaggcc gttattcttc ctgtcaaagt tccttctaaa    14220
accaatataa ggagataaca atggggcaca atatgatgac cacccaaaaa tggtatgagc    14280
atattactaa tgtaatcata ggcaatactg ctaatttcaa tagcggttgc cttgactcta    14340
tagattatgt agatgaaaga aaaggcgttc cgcttgcagc tatgcaacat attttcatgg    14400
acgttagagc tgcagcttcc catgcctatc tatttgaaca tgatcttaag aaattcaagc    14460
aatatgctta tgttgcagga aagctggggg ttttgctgag tgtaaattct acagaccctg    14520
aacccttctt ctttccctgt gacatgctca acattcaaaa tccgatgttt ctgatgctga    14580
tgagcgacag cccacagctg cgtgagtttc tggtgcgcaa tatcgacaac atcgccaacg    14640
atacagaagc ctttataaac cgctacgacc tcaaccggca tatgatttac aatactctgc    14700
tgatggtgga gggtaagcag cttgatcggt tgaaacaacg tagcgagaaa gtcttggcgc    14760
atcccacccc tagcaaatgg ctgcaaaagc ggttgtacga ttaccgcttc ttcctcgctt    14820
tcgccgaaca ggatgccgag gcaatgaaag ccgccttaga gccgcttttc gataaaaaaa    14880
ccgcgcgtat ggctgccaaa gaaacattgt cctatttcga tttctacctg cagccgcaaa    14940
tcgttaccta cgccaaaatc gcatccatgc acggtttcga tttgggcata gatcaagaaa    15000
tctcaccgag ggatttgatt gtttacgatc cgctgccggc agacgaatat caagacatct    15060
tcgattttat gaaacagtat gacttgtctt acccgtatga atatctgcag gattggatag    15120
attactatac gttcaaaacc gataagctgg tatttggtaa cgcgaagcga gagtgagccg    15180
taaaactctg agctcctgtt ttatagatta caactttagg ccgtcttaaa gctgaaagat    15240
tttcgaaagc tataaattga agcccttcca cagtacatag atctgtgttg tggcggggct    15300
ttaccacgct gattgccgga gaagaactca acctgctggc aaaacaaggc atgagatctt    15360
tgcaataaca tgagttgaga cctttgcaaa aaagcccttc cccgacatcc gaaacccaaa    15420
cacaggattt cggctgtttt cgtaccaaat acctcctaat tttacccaaa taccccctta    15480
atcctcctcg gacacccgat aatcaggcat ccgggctgcc ttttaggcgg cagcgggcgc    15540
atttagcctg ttggccgctt tcaacaggtt caaacacatc gccttcaggt ggctttgcgc    15600
actcactttg tcatttccaa                                                15620
```

<210> SEQ ID NO 37
<211> LENGTH: 580
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

-continued

```
Met Lys Phe Phe Pro Ala Pro Cys Leu Leu Val Ile Leu Ala Val Ile
1               5                   10                  15

Pro Leu Lys Thr Leu Ala Ala Asp Glu Asn Asp Ala Glu Leu Ile Arg
            20                  25                  30

Ser Met Gln Arg Gln Gln His Ile Asp Ala Glu Leu Leu Thr Asp Ala
        35                  40                  45

Asn Val Arg Phe Glu Gln Pro Leu Glu Lys Asn Asn Tyr Val Leu Ser
    50                  55                  60

Glu Asp Glu Thr Pro Cys Thr Arg Val Asn Tyr Ile Ser Leu Asp Asp
65                  70                  75                  80

Lys Thr Ala Arg Lys Phe Ser Phe Leu Pro Ser Val Leu Met Lys Glu
                85                  90                  95

Thr Ala Phe Lys Thr Gly Met Cys Leu Gly Ser Asn Asn Leu Ser Arg
            100                 105                 110

Leu Gln Lys Ala Ala Gln Gln Ile Leu Ile Val Arg Gly Tyr Leu Thr
        115                 120                 125

Ser Gln Ala Ile Ile Gln Pro Gln Asn Met Asp Ser Gly Ile Leu Lys
    130                 135                 140

Leu Arg Val Ser Ala Gly Glu Ile Gly Asp Ile Arg Tyr Glu Lys
145                 150                 155                 160

Arg Asp Gly Lys Ser Ala Glu Gly Ser Ile Ser Ala Phe Asn Asn Lys
                165                 170                 175

Phe Pro Leu Tyr Arg Asn Lys Ile Leu Asn Leu Arg Asp Val Glu Gln
            180                 185                 190

Gly Leu Glu Asn Leu Arg Arg Leu Pro Ser Val Lys Thr Asp Ile Gln
        195                 200                 205

Ile Ile Pro Ser Glu Glu Gly Lys Ser Asp Leu Gln Ile Lys Trp
    210                 215                 220

Gln Gln Asn Lys Pro Ile Arg Phe Ser Ile Gly Ile Asp Asp Ala Gly
225                 230                 235                 240

Gly Lys Thr Thr Gly Lys Tyr Gln Gly Asn Val Ala Leu Ser Phe Asp
                245                 250                 255

Asn Pro Leu Gly Leu Ser Asp Leu Phe Tyr Val Ser Tyr Gly Arg Gly
            260                 265                 270

Leu Val His Lys Thr Asp Leu Thr Asp Ala Thr Gly Thr Glu Thr Glu
        275                 280                 285

Ser Gly Ser Arg Ser Tyr Ser Val His Tyr Ser Val Pro Val Lys Lys
    290                 295                 300

Trp Leu Phe Ser Phe Asn His Asn Gly His Arg Tyr His Glu Ala Thr
305                 310                 315                 320

Glu Gly Tyr Ser Val Asn Tyr Asp Tyr Asn Gly Lys Gln Tyr Gln Ser
                325                 330                 335

Ser Leu Ala Ala Glu Arg Met Leu Trp Arg Asn Arg Phe His Lys Thr
            340                 345                 350

Ser Val Gly Met Lys Leu Trp Thr Arg Gln Thr Tyr Lys Tyr Ile Asp
        355                 360                 365

Asp Ala Glu Ile Glu Val Gln Arg Arg Ser Ala Gly Trp Glu Ala
    370                 375                 380

Glu Leu Arg His Arg Ala Tyr Leu Asn Arg Trp Gln Leu Asp Gly Lys
385                 390                 395                 400

Leu Ser Tyr Lys Arg Gly Thr Gly Met Arg Gln Ser Met Pro Ala Pro
                405                 410                 415

Glu Glu Asn Gly Gly Gly Thr Ile Pro Gly Thr Ser Arg Met Lys Ile
            420                 425                 430
```

Ile Thr Ala Gly Leu Asp Ala Ala Pro Phe Met Leu Gly Lys Gln
            435                 440                 445

Gln Phe Phe Tyr Ala Thr Ala Ile Gln Ala Gln Trp Asn Lys Thr Pro
    450                 455                 460

Leu Val Ala Gln Asp Lys Leu Ser Ile Gly Ser Arg Tyr Thr Val Arg
465                 470                 475                 480

Gly Phe Asp Gly Glu Gln Ser Leu Phe Gly Glu Arg Gly Phe Tyr Trp
                485                 490                 495

Gln Asn Thr Leu Thr Trp Tyr Phe His Pro Asn His Gln Phe Tyr Leu
            500                 505                 510

Gly Ala Asp Tyr Gly Arg Val Ser Gly Glu Ser Ala Gln Tyr Val Ser
        515                 520                 525

Gly Lys Gln Leu Met Gly Ala Val Val Gly Phe Arg Gly Gly His Lys
    530                 535                 540

Val Gly Gly Met Phe Ala Tyr Asp Leu Phe Ala Gly Lys Pro Leu His
545                 550                 555                 560

Lys Pro Lys Gly Phe Gln Thr Thr Asn Thr Val Tyr Gly Phe Asn Leu
                565                 570                 575

Asn Tyr Ser Phe
            580

<210> SEQ ID NO 38
<211> LENGTH: 1981
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Asn Lys Gly Leu His Arg Ile Ile Phe Ser Lys Lys His Ser Thr
1               5                   10                  15

Met Val Ala Val Ala Glu Thr Ala Asn Ser Gln Gly Lys Gly Lys Gln
            20                  25                  30

Ala Gly Ser Ser Val Ser Val Ser Leu Lys Thr Ser Gly Asp Leu Cys
        35                  40                  45

Gly Lys Leu Lys Thr Thr Leu Lys Thr Leu Val Cys Ser Leu Val Ser
    50                  55                  60

Leu Ser Met Val Leu Pro Ala His Ala Gln Ile Thr Thr Asp Lys Ser
65                  70                  75                  80

Ala Pro Lys Asn Gln Gln Val Val Ile Leu Lys Thr Asn Thr Gly Ala
                85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Leu Val Lys Gly Ser Ala Gln Leu Ile
    130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Gly Phe Lys Asn Val Gly Arg Gly Ile Leu Thr
            180                 185                 190

Ile Gly Ala Pro Gln Ile Gly Lys Asp Gly Ala Leu Thr Gly Phe Asp
        195                 200                 205

```
Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
            260                 265                 270

Lys Pro Thr Ile Ala Leu Asp Thr Ala Ala Leu Gly Gly Met Tyr Ala
        275                 280                 285

Asp Ser Ile Thr Leu Ile Ala Asn Glu Lys Gly Val Gly Val Lys Asn
    290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
                325                 330                 335

Ala Ser Pro Thr Tyr Leu Ser Ile Glu Thr Thr Glu Lys Gly Ala Ala
            340                 345                 350

Gly Thr Phe Ile Ser Asn Gly Gly Arg Ile Glu Ser Lys Gly Leu Leu
        355                 360                 365

Val Ile Glu Thr Gly Glu Asp Ile Ser Leu Arg Asn Gly Ala Val Val
    370                 375                 380

Gln Asn Asn Gly Ser Arg Pro Ala Thr Thr Val Leu Asn Ala Gly His
385                 390                 395                 400

Asn Leu Val Ile Glu Ser Lys Thr Asn Val Asn Asn Ala Lys Gly Ser
                405                 410                 415

Ala Asn Leu Ser Ala Gly Gly Arg Thr Thr Ile Asn Asp Ala Thr Ile
            420                 425                 430

Gln Ala Gly Ser Ser Val Tyr Ser Ser Thr Lys Gly Asp Thr Glu Leu
        435                 440                 445

Gly Glu Asn Thr Arg Ile Ile Ala Glu Asn Val Thr Val Leu Ser Asn
    450                 455                 460

Gly Ser Ile Gly Ser Ala Ala Val Ile Glu Ala Lys Asp Thr Ala His
465                 470                 475                 480

Ile Glu Ser Gly Lys Pro Leu Ser Leu Glu Thr Ser Thr Val Ala Ser
                485                 490                 495

Asn Ile Arg Leu Asn Asn Gly Asn Ile Lys Gly Gly Lys Gln Leu Ala
            500                 505                 510

Leu Leu Ala Asp Asp Asn Ile Thr Ala Lys Thr Thr Asn Leu Asn Thr
        515                 520                 525

Pro Gly Asn Leu Tyr Val His Thr Gly Lys Asp Leu Asn Leu Asn Val
    530                 535                 540

Asp Lys Asp Leu Ser Ala Ala Ser Ile His Leu Lys Ser Asp Asn Ala
545                 550                 555                 560

Ala His Ile Thr Gly Thr Ser Lys Thr Leu Thr Ala Ser Lys Asp Met
                565                 570                 575

Gly Val Glu Ala Gly Leu Leu Asn Val Thr Asn Thr Asn Leu Arg Thr
            580                 585                 590

Asn Ser Gly Asn Leu His Ile Gln Ala Ala Lys Gly Asn Ile Gln Leu
        595                 600                 605

Arg Asn Thr Lys Leu Asn Ala Ala Lys Ala Leu Glu Thr Thr Ala Leu
    610                 615                 620

Gln Gly Asn Ile Val Ser Asp Gly Leu His Ala Val Ser Ala Asp Gly
```

-continued

```
            625                 630                 635                 640
        His Val Ser Leu Leu Ala Asn Gly Asn Ala Asp Phe Thr Gly His Asn
                        645                 650                 655
        Thr Leu Thr Ala Lys Ala Asp Val Asn Ala Gly Ser Val Gly Lys Gly
                        660                 665                 670
        Arg Leu Lys Ala Asp Asn Thr Asn Ile Thr Ser Ser Gly Asp Ile
                        675                 680                 685
        Thr Leu Val Ala Gly Asn Gly Ile Gln Leu Gly Asp Gly Lys Gln Arg
                        690                 695                 700
        Asn Ser Ile Asn Gly Lys His Ile Ser Ile Lys Asn Asn Gly Gly Asn
        705                 710                 715                 720
        Ala Asp Leu Lys Asn Leu Asn Val His Ala Lys Ser Gly Ala Leu Asn
                        725                 730                 735
        Ile His Ser Asp Arg Ala Leu Ser Ile Glu Asn Thr Lys Leu Glu Ser
                        740                 745                 750
        Thr His Asn Thr His Leu Asn Ala Gln His Glu Arg Val Thr Leu Asn
                        755                 760                 765
        Gln Val Asp Ala Tyr Ala His Arg His Leu Ser Ile Thr Gly Ser Gln
                        770                 775                 780
        Ile Trp Gln Asn Asp Lys Leu Pro Ser Ala Asn Lys Leu Val Ala Asn
        785                 790                 795                 800
        Gly Val Leu Ala Leu Asn Ala Arg Tyr Ser Gln Ile Ala Asp Asn Thr
                        805                 810                 815
        Thr Leu Arg Ala Gly Ala Ile Asn Leu Thr Ala Gly Thr Ala Leu Val
                        820                 825                 830
        Lys Arg Gly Asn Ile Asn Trp Ser Thr Val Ser Thr Lys Thr Leu Glu
                        835                 840                 845
        Asp Asn Ala Glu Leu Lys Pro Leu Ala Gly Arg Leu Asn Ile Glu Ala
                        850                 855                 860
        Gly Ser Gly Thr Leu Thr Ile Glu Pro Ala Asn Arg Ile Ser Ala His
        865                 870                 875                 880
        Thr Asp Leu Ser Ile Lys Thr Gly Gly Lys Leu Leu Leu Ser Ala Lys
                        885                 890                 895
        Gly Gly Asn Ala Gly Ala Pro Ser Ala Gln Val Ser Ser Leu Glu Ala
                        900                 905                 910
        Lys Gly Asn Ile Arg Leu Val Thr Gly Glu Thr Asp Leu Arg Gly Ser
                        915                 920                 925
        Lys Ile Thr Ala Gly Lys Asn Leu Val Val Ala Thr Thr Lys Gly Lys
                        930                 935                 940
        Leu Asn Ile Glu Ala Val Asn Asn Ser Phe Ser Asn Tyr Phe Pro Thr
        945                 950                 955                 960
        Gln Lys Ala Ala Glu Leu Asn Gln Lys Ser Lys Glu Leu Glu Gln Gln
                        965                 970                 975
        Ile Ala Gln Leu Lys Lys Ser Ser Pro Lys Ser Lys Leu Ile Pro Thr
                        980                 985                 990
        Leu Gln Glu Glu Arg Asp Arg Leu Ala Phe Tyr Ile Gln Ala Ile Asn
                        995                 1000                1005
        Lys Glu Val Lys Gly Lys Lys Pro Lys Gly Lys Glu Tyr Leu Gln
                        1010                1015                1020
        Ala Lys Leu Ser Ala Gln Asn Ile Asp Leu Ile Ser Ala Gln Gly
                        1025                1030                1035
        Ile Glu Ile Ser Gly Ser Asp Ile Thr Ala Ser Lys Lys Leu Asn
                        1040                1045                1050
```

-continued

```
Leu His Ala Ala Gly Val Leu Pro Lys Ala Ala Asp Ser Glu Ala
    1055                1060                1065
Ala Ala Ile Leu Ile Asp Gly Ile Thr Asp Gln Tyr Glu Ile Gly
    1070                1075                1080
Lys Pro Thr Tyr Lys Ser His Tyr Asp Lys Ala Ala Leu Asn Lys
    1085                1090                1095
Pro Ser Arg Leu Thr Gly Arg Thr Gly Val Ser Ile His Ala Ala
    1100                1105                1110
Ala Ala Leu Asp Asp Ala Arg Ile Ile Ile Gly Ala Ser Glu Ile
    1115                1120                1125
Lys Ala Pro Ser Gly Ser Ile Asp Ile Lys Ala His Ser Asp Ile
    1130                1135                1140
Val Leu Glu Ala Gly Gln Asn Asp Ala Tyr Thr Phe Leu Lys Thr
    1145                1150                1155
Lys Gly Lys Ser Gly Lys Ile Ile Arg Lys Thr Lys Phe Thr Ser
    1160                1165                1170
Thr Arg Asp His Leu Ile Met Pro Ala Pro Val Glu Leu Thr Ala
    1175                1180                1185
Asn Gly Ile Thr Leu Gln Ala Gly Gly Asn Ile Glu Ala Asn Thr
    1190                1195                1200
Thr Arg Phe Asn Ala Pro Ala Gly Lys Val Thr Leu Val Ala Gly
    1205                1210                1215
Glu Glu Leu Gln Leu Leu Ala Glu Glu Gly Ile His Lys His Glu
    1220                1225                1230
Leu Asp Val Gln Lys Ser Arg Arg Phe Ile Gly Ile Lys Val Gly
    1235                1240                1245
Lys Ser Asn Tyr Ser Lys Asn Glu Leu Asn Glu Thr Lys Leu Pro
    1250                1255                1260
Val Arg Val Val Ala Gln Thr Ala Ala Thr Arg Ser Gly Trp Asp
    1265                1270                1275
Thr Val Leu Glu Gly Thr Glu Phe Lys Thr Thr Leu Ala Gly Ala
    1280                1285                1290
Asp Ile Gln Ala Gly Val Gly Glu Lys Ala Arg Val Asp Ala Lys
    1295                1300                1305
Ile Ile Leu Lys Gly Ile Val Asn Arg Ile Gln Ser Glu Glu Lys
    1310                1315                1320
Leu Glu Thr Asn Ser Thr Val Trp Gln Lys Gln Ala Gly Arg Gly
    1325                1330                1335
Ser Thr Ile Glu Thr Leu Lys Leu Pro Ser Phe Glu Ser Pro Thr
    1340                1345                1350
Pro Pro Lys Leu Ser Ala Pro Gly Gly Tyr Ile Val Asp Ile Pro
    1355                1360                1365
Lys Gly Asn Leu Lys Thr Glu Ile Glu Lys Leu Ser Lys Gln Pro
    1370                1375                1380
Glu Tyr Ala Tyr Leu Lys Gln Leu Gln Val Ala Lys Asn Ile Asn
    1385                1390                1395
Trp Asn Gln Val Gln Leu Ala Tyr Asp Arg Trp Asp Tyr Lys Gln
    1400                1405                1410
Glu Gly Leu Thr Glu Ala Gly Ala Ala Ile Ile Ala Leu Ala Val
    1415                1420                1425
Thr Val Val Thr Ser Gly Ala Gly Thr Gly Ala Val Leu Gly Leu
    1430                1435                1440
Asn Gly Ala Ala Ala Ala Ala Thr Asp Ala Ala Phe Ala Ser Leu
    1445                1450                1455
```

```
Ala Ser Gln Ala Ser Val Ser Phe Ile Asn Asn Lys Gly Asp Val
    1460            1465                1470
Gly Lys Thr Leu Lys Glu Leu Gly Arg Ser Ser Thr Val Lys Asn
    1475            1480                1485
Leu Val Val Ala Ala Ala Thr Ala Gly Val Ala Asp Lys Ile Gly
    1490            1495                1500
Ala Ser Ala Leu Asn Asn Val Ser Asp Lys Gln Trp Ile Asn Asn
    1505            1510                1515
Leu Thr Val Asn Leu Ala Asn Ala Gly Ser Ala Ala Leu Ile Asn
    1520            1525                1530
Thr Ala Val Asn Gly Gly Ser Leu Lys Asp Asn Leu Glu Ala Asn
    1535            1540                1545
Ile Leu Ala Ala Leu Val Asn Thr Ala His Gly Glu Ala Ala Ser
    1550            1555                1560
Lys Ile Lys Gln Leu Asp Gln His Tyr Ile Val His Lys Ile Ala
    1565            1570                1575
His Ala Ile Ala Gly Cys Ala Ala Ala Ala Asn Lys Gly Lys
    1580            1585                1590
Cys Gln Asp Gly Ala Ile Gly Ala Ala Val Gly Glu Ile Val Gly
    1595            1600                1605
Glu Ala Leu Thr Asn Gly Lys Asn Pro Asp Thr Leu Thr Ala Lys
    1610            1615                1620
Glu Arg Glu Gln Ile Leu Ala Tyr Ser Lys Leu Val Ala Gly Thr
    1625            1630                1635
Val Ser Gly Val Val Gly Gly Asp Val Asn Ala Ala Ala Asn Ala
    1640            1645                1650
Ala Glu Val Ala Val Lys Asn Asn Gln Leu Ser Asp Lys Glu Gly
    1655            1660                1665
Arg Glu Phe Asp Asn Glu Met Thr Ala Cys Ala Lys Gln Asn Asn
    1670            1675                1680
Pro Gln Leu Cys Arg Lys Asn Thr Val Lys Lys Tyr Gln Asn Val
    1685            1690                1695
Ala Asp Lys Arg Leu Ala Ala Ser Ile Ala Ile Cys Thr Asp Ile
    1700            1705                1710
Ser Arg Ser Thr Glu Cys Arg Thr Ile Arg Lys Gln His Leu Ile
    1715            1720                1725
Asp Ser Arg Ser Leu His Ser Ser Trp Glu Ala Gly Leu Ile Gly
    1730            1735                1740
Lys Asp Asp Glu Trp Tyr Lys Leu Phe Ser Lys Ser Tyr Thr Gln
    1745            1750                1755
Ala Asp Leu Ala Leu Gln Ser Tyr His Leu Asn Thr Ala Ala Lys
    1760            1765                1770
Ser Trp Leu Gln Ser Gly Asn Thr Lys Pro Leu Ser Glu Trp Met
    1775            1780                1785
Ser Asp Gln Gly Tyr Thr Leu Ile Ser Gly Val Asn Pro Arg Phe
    1790            1795                1800
Ile Pro Ile Pro Arg Gly Phe Val Lys Gln Asn Thr Pro Ile Thr
    1805            1810                1815
Asn Val Lys Tyr Pro Glu Gly Ile Ser Phe Asp Thr Asn Leu Lys
    1820            1825                1830
Arg His Leu Ala Asn Ala Asp Gly Phe Ser Gln Glu Gln Gly Ile
    1835            1840                1845
Lys Gly Ala His Asn Arg Thr Asn Phe Met Ala Glu Leu Asn Ser
```

```
                    1850                1855                1860

Arg Gly Gly Arg Val Lys Ser Glu Thr Gln Thr Asp Ile Glu Gly
        1865                1870                1875

Ile Thr Arg Ile Lys Tyr Glu Ile Pro Thr Leu Asp Arg Thr Gly
        1880                1885                1890

Lys Pro Asp Gly Gly Phe Lys Glu Ile Ser Ser Ile Lys Thr Val
        1895                1900                1905

Tyr Asn Pro Lys Lys Phe Ser Asp Asp Lys Ile Leu Gln Met Ala
        1910                1915                1920

Gln Asn Ala Ala Ser Gln Gly Tyr Ser Lys Ala Ser Lys Ile Ala
        1925                1930                1935

Gln Asn Glu Arg Thr Lys Ser Ile Ser Glu Arg Lys Asn Val Ile
        1940                1945                1950

Gln Phe Ser Glu Thr Phe Asp Gly Ile Lys Phe Arg Ser Tyr Phe
        1955                1960                1965

Asp Val Asn Thr Gly Arg Ile Thr Asn Ile His Pro Glu
        1970                1975                1980

<210> SEQ ID NO 39
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Lys Asn Asn Ile Phe Leu Asn Leu Asn Lys Lys Ser Ile Asn Asn
1               5                   10                  15

Asn His Phe Val Ile Ser Ile Phe Phe Glu Thr Ile Tyr Gln Phe Glu
                20                  25                  30

Thr Lys Asp Thr Leu Leu Glu Cys Phe Lys Asn Ile Thr Thr Thr Gly
            35                  40                  45

His Phe Gly Val Ile Gly Ala Gln Tyr Glu Lys Ile Asp Ala Thr Arg
        50                  55                  60

Trp Ile Gly Asp Tyr Glu Val Asn Gly Phe Glu Tyr Ile Asp Lys
65                  70                  75                  80

Ala Pro Ser Ile Tyr Phe Ser Val Gly Asp Asp Phe Asn Pro Glu Glu
                85                  90                  95

Leu Ile Ile Pro Ile Asn Leu Ala Tyr His Tyr Phe Asn Ile Ala Ile
            100                 105                 110

Ser Asp Phe Leu Ile Ala His Pro Glu Tyr Gln Lys Lys Cys Lys Glu
        115                 120                 125

Ile Gln Lys Thr Tyr Ser Gln Thr Asn Cys Ser Leu His Glu Thr
    130                 135                 140

<210> SEQ ID NO 40
<211> LENGTH: 833
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Val Leu Lys Thr Pro Pro Thr Leu Ala Ala Glu Leu Ser Gly Lys Thr
1               5                   10                  15

Gly Val Ser Ile Ser Ala Pro Tyr Ala Asn Glu Asn Ser Arg Ile Leu
                20                  25                  30
```

```
Leu Ser Thr Thr Asp Ile Ser Ser Glu Asn Gly Lys Ile Lys Ile Gln
            35                  40                  45
Ser Tyr Gly Asp Gln Tyr Tyr Tyr Ala Arg Gln Ser Glu Leu Tyr Thr
 50                  55                  60
Phe Glu Arg Arg Ser Tyr Lys Thr Gly Lys Trp Tyr Asn Arg Lys His
 65                  70                  75                  80
Ile Thr Glu Val Lys Glu His Lys Asn Ala Lys Pro Asp Ala Val Asn
                    85                  90                  95
Leu Ser Ala Ser Gln Gly Ile Asp Ile Lys Ser Gly Ser Ile Asp
                100                 105                 110
Ala Tyr Ala Thr Ala Phe Asp Ala Pro Lys Gly Ser Ile Asn Ile Glu
                115                 120                 125
Ala Gly Arg Lys Leu Thr Leu Tyr Ala Val Glu Glu Leu Asn Tyr Asp
                130                 135                 140
Lys Leu Asp Ser Gln Lys Arg Arg Phe Leu Gly Ile Ser Tyr Ser
145                 150                 155                 160
Lys Ala His Asp Thr Thr Thr Gln Val Met Lys Thr Ala Leu Pro Ser
                165                 170                 175
Arg Val Val Ala Glu Ser Ala Asn Leu Gln Ser Gly Trp Asp Thr Lys
                180                 185                 190
Leu Gln Gly Thr Gln Phe Glu Thr Thr Leu Gly Gly Ala Thr Ile Arg
                195                 200                 205
Ala Gly Val Gly Glu Gln Ala Arg Ala Asp Ala Lys Ile Ile Leu Glu
                210                 215                 220
Gly Ile Lys Ser Ser Ile His Thr Glu Thr Val Ser Ser Ser Lys Ser
225                 230                 235                 240
Thr Leu Trp Gln Lys Gln Ala Gly Arg Gly Ser Asn Ile Glu Thr Leu
                245                 250                 255
Gln Leu Pro Ser Phe Thr Gly Pro Val Ala Pro Val Leu Ser Ala Pro
                260                 265                 270
Gly Gly Tyr Ile Val Asp Ile Pro Lys Gly Asn Leu Lys Thr Gln Ile
                275                 280                 285
Glu Thr Leu Thr Lys Gln Pro Glu Tyr Ala Tyr Leu Lys Gln Leu Gln
                290                 295                 300
Val Ala Lys Asn Ile Asn Trp Asn Gln Val Gln Leu Ala Tyr Asp Lys
305                 310                 315                 320
Trp Asp Tyr Lys Gln Glu Gly Met Thr Pro Ala Ala Ala Val Val
                325                 330                 335
Val Ile Val Val Thr Val Leu Thr Tyr Gly Ala Leu Ser Ala Pro Ala
                340                 345                 350
Ala Ala Gly Thr Ala Gly Ala Ala Gly Ala Gly Ala Gly Gly Ala Ala
                355                 360                 365
Ala Gly Thr Ala Ala Gly Thr Gly Val Ala Ala Gly Thr Ala Ala Thr
                370                 375                 380
Thr Gly Val Ala Ala Gly Thr Ser Ala Ala Ile Thr Thr Ala Ala
385                 390                 395                 400
Gly Lys Ala Ala Leu Ala Ser Leu Ala Ser Gln Ala Ala Val Ser Leu
                405                 410                 415
Ile Asn Asn Lys Gly Asp Ile Asn His Thr Leu Lys Glu Leu Gly Lys
                420                 425                 430
Ser Ser Thr Val Arg Gln Ala Ala Thr Ala Ala Val Thr Ala Gly Val
                435                 440                 445
Leu Gln Gly Ile Ser Gly Leu Asn Thr Gln Ala Ala Glu Ala Val Ser
```

|  |  |  |  | 450 |  |  |  | 455 |  |  |  | 460 |  |  |
|---|---|---|---|---|---|---|---|---|---|---|---|---|---|---|
| Lys | His | Phe | His | Ser | Pro | Ala | Ala | Gly | Lys | Leu | Thr | Ala | Asn | Leu | Ile |
| 465 |  |  |  |  | 470 |  |  |  |  | 475 |  |  |  |  | 480 |

Asn Ser Thr Ala Ala Ser Val His Thr Ala Ile Asn Gly Gly Ser
            485                 490                 495

Leu Lys Asp Asn Leu Gly Asp Ala Ala Leu Gly Ala Ile Val Ser Thr
            500                 505                 510

Val His Gly Glu Val Ala Ser Lys Ile Lys Phe Asn Leu Ser Glu Asp
            515                 520                 525

Tyr Ile Ala His Lys Ile Ala His Ala Val Ala Gly Cys Ala Ser Ala
530                 535                 540

Val Ala Asn Lys Gly Lys Cys Arg Asp Gly Ala Ile Gly Ala Ala Val
545                 550                 555                 560

Gly Glu Met Val Gly Glu Thr Leu Leu Asp Gly Arg Asp Val Gly Lys
            565                 570                 575

Leu Ser Pro Gln Glu Arg Gln Lys Val Ile Ala Tyr Ser Gln Ile Ile
            580                 585                 590

Ala Gly Ser Ala Val Ala Leu Val Lys Gly Asp Val Asn Thr Ala Val
            595                 600                 605

Asn Ala Ala Thr Val Ala Val Glu Asn Asn Ser Leu Leu Ala Arg Arg
610                 615                 620

Arg Val Asn Ile Arg Trp Thr Pro Arg Gln Glu Leu Glu His Glu Tyr
625                 630                 635                 640

Ala Ile Leu Glu Ile Gln Ala Ile Thr Asn Gln Ile Arg Arg Leu Asp
            645                 650                 655

Pro Lys Phe Asn Gly Ile Ala Ile Leu Arg Thr Pro Gly Glu Pro Trp
            660                 665                 670

Thr Arg His Asp Val Gln Thr Tyr Arg Gln Tyr Tyr Asn Gln Leu Arg
            675                 680                 685

Glu Ser Arg Gly Phe Ala Val Glu Pro Ile Tyr Arg Ile Arg Ile Asn
            690                 695                 700

Asn Gly Asn Glu Phe Asn Arg Ile Met Ser Ser Lys Tyr Pro Tyr Asn
705                 710                 715                 720

Glu Leu Tyr Val Ala Asn Pro Lys Ser Ala Thr Gly Tyr Phe Arg Val
            725                 730                 735

Asp Ser Tyr Asp Pro Ala Thr Arg Glu Ile Ile Ser Arg Lys Phe Thr
            740                 745                 750

Gln Phe Ser Gln Ile Gln Glu Ser Thr Gly Ile Gly Tyr Ile Lys Glu
            755                 760                 765

Ala Val Arg Lys Tyr Ser Pro Gly Thr Val Ile Ser Asn Val Pro Ser
770                 775                 780

Thr Pro Thr Thr Ile Arg Gly Arg Lys Leu Glu Gly Lys Leu Ile Leu
785                 790                 795                 800

Glu Val Pro Ala Gln Val Asn Pro Ile Pro Gln Ser Val Leu Arg Ala
            805                 810                 815

Ala Gln Glu Glu Asn Val Ile Ile Arg Asp Thr Thr Gly Arg Ile Tyr
            820                 825                 830

Lys

```
<210> SEQ ID NO 41
<211> LENGTH: 664
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 41

Met Lys Thr Ala Leu Pro Ser Arg Val Val Ala Glu Ser Ala Asn Leu
1               5                   10                  15

Gln Ser Gly Trp Asp Thr Lys Leu Gln Gly Thr Gln Phe Glu Thr Thr
            20                  25                  30

Leu Gly Gly Ala Thr Ile Arg Ala Gly Val Gly Glu Gln Ala Arg Ala
        35                  40                  45

Asp Ala Lys Ile Ile Leu Glu Gly Ile Lys Ser Ser Ile His Thr Glu
50                  55                  60

Thr Val Ser Ser Ser Lys Ser Thr Leu Trp Gln Lys Gln Ala Gly Arg
65                  70                  75                  80

Gly Ser Asn Ile Glu Thr Leu Gln Leu Pro Ser Phe Thr Gly Pro Val
                85                  90                  95

Ala Pro Val Leu Ser Ala Pro Gly Gly Tyr Ile Val Asp Ile Pro Lys
            100                 105                 110

Gly Asn Leu Lys Thr Gln Ile Glu Thr Leu Thr Lys Gln Pro Glu Tyr
        115                 120                 125

Ala Tyr Leu Lys Gln Leu Gln Val Ala Lys Asn Ile Asn Trp Asn Gln
130                 135                 140

Val Gln Leu Ala Tyr Asp Lys Trp Asp Tyr Lys Gln Glu Gly Met Thr
145                 150                 155                 160

Pro Ala Ala Ala Val Val Ile Val Thr Val Leu Thr Tyr
                165                 170                 175

Gly Ala Leu Ser Ala Pro Ala Ala Gly Thr Ala Gly Ala Ala Gly
            180                 185                 190

Ala Gly Ala Gly Ala Ala Ala Gly Thr Ala Ala Gly Thr Gly Val
        195                 200                 205

Ala Ala Gly Thr Ala Ala Thr Thr Gly Val Ala Ala Gly Thr Ser Ala
210                 215                 220

Ala Ala Ile Thr Thr Ala Ala Gly Lys Ala Ala Leu Ala Ser Leu Ala
225                 230                 235                 240

Ser Gln Ala Ala Val Ser Leu Ile Asn Asn Lys Gly Asp Ile Asn His
                245                 250                 255

Thr Leu Lys Glu Leu Gly Lys Ser Ser Thr Val Arg Gln Ala Ala Thr
            260                 265                 270

Ala Ala Val Thr Ala Gly Val Leu Gln Gly Ile Ser Gly Leu Asn Thr
        275                 280                 285

Gln Ala Ala Glu Ala Val Ser Lys His Phe His Ser Pro Ala Ala Gly
290                 295                 300

Lys Leu Thr Ala Asn Leu Ile Asn Ser Thr Ala Ala Ser Val His
305                 310                 315                 320

Thr Ala Ile Asn Gly Gly Ser Leu Lys Asp Asn Leu Gly Asp Ala Ala
                325                 330                 335

Leu Gly Ala Ile Val Ser Thr Val His Gly Glu Val Ala Ser Lys Ile
            340                 345                 350

Lys Phe Asn Leu Ser Glu Asp Tyr Ile Ala His Lys Ile Ala His Ala
        355                 360                 365

Val Ala Gly Cys Ala Ser Ala Val Ala Asn Lys Gly Lys Cys Arg Asp
370                 375                 380

Gly Ala Ile Gly Ala Ala Val Gly Glu Met Val Gly Glu Thr Leu Leu
385                 390                 395                 400

Asp Gly Arg Asp Val Gly Lys Leu Ser Pro Gln Glu Arg Gln Lys Val 405                 410                 415
Ile Ala Tyr Ser Gln Ile Ile Ala Gly Ser Ala Val Ala Leu Val Lys
                420                 425                 430

Gly Asp Val Asn Thr Ala Val Asn Ala Ala Thr Val Ala Val Glu Asn
                435                 440                 445

Asn Ser Leu Leu Ala Arg Arg Arg Val Asn Ile Arg Trp Thr Pro Arg
            450                 455                 460

Gln Glu Leu Glu His Glu Tyr Ala Ile Leu Ile Gln Ala Ile Thr
465                 470                 475                 480

Asn Gln Ile Arg Arg Leu Asp Pro Lys Phe Asn Gly Ile Ala Ile Leu
                485                 490                 495

Arg Thr Pro Gly Glu Pro Trp Thr Arg His Asp Val Gln Thr Tyr Arg
                500                 505                 510

Gln Tyr Tyr Asn Gln Leu Arg Glu Ser Arg Gly Phe Ala Val Glu Pro
            515                 520                 525

Ile Tyr Arg Ile Arg Ile Asn Asn Gly Asn Glu Phe Asn Arg Ile Met
        530                 535                 540

Ser Ser Lys Tyr Pro Tyr Asn Glu Leu Tyr Val Ala Asn Pro Lys Ser
545                 550                 555                 560

Ala Thr Gly Tyr Phe Arg Val Asp Ser Tyr Asp Pro Ala Thr Arg Glu
                565                 570                 575

Ile Ile Ser Arg Lys Phe Thr Gln Phe Ser Gln Ile Gln Glu Ser Thr
            580                 585                 590

Gly Ile Gly Tyr Ile Lys Glu Ala Val Arg Lys Tyr Ser Pro Gly Thr
        595                 600                 605

Val Ile Ser Asn Val Pro Ser Thr Pro Thr Thr Ile Arg Gly Arg Lys
    610                 615                 620

Leu Glu Gly Lys Leu Ile Leu Glu Val Pro Ala Gln Val Asn Pro Ile
625                 630                 635                 640

Pro Gln Ser Val Leu Arg Ala Ala Gln Glu Gly Asn Val Ile Ile Arg
                645                 650                 655

Asp Thr Thr Gly Arg Ile Tyr Lys
                660

<210> SEQ ID NO 42
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Lys Lys Asp Ile Phe Tyr Cys Glu Gln Trp Ser Tyr Gly Tyr Lys
1               5                   10                  15

Arg Leu His Lys Pro Phe Ser Glu Lys Gln Ala Glu Glu Lys His Leu
                20                  25                  30

Lys Gly Glu Leu Tyr Thr Ala Val Ile Gly Ser Ala Thr Gln Pro Glu
            35                  40                  45

Tyr Val Ile Thr Leu Arg Glu Glu Val Gly Phe Phe Ser Val Asn Phe
        50                  55                  60

Phe Asp Lys Phe Gly Arg Asp Tyr Leu Thr His Gln Phe Gln Lys Tyr
65                  70                  75                  80

Ser Asn Ser Asn Tyr Tyr Phe Leu Ser Met Ala Val Trp Arg Asp Tyr
                85                  90                  95

Ile Thr Leu Glu Ser His Asp Leu Ala Glu Gly Tyr Thr Tyr Phe Phe

```
                    100                 105                 110
Asn Glu Asn Thr Asp Asp Cys Tyr Val Leu Lys Gln Asp Phe Ile Asn
                115                 120                 125

Asn Glu Arg Tyr Glu Lys Thr Glu Leu Tyr Ser Gln Lys Asp Lys Val
            130                 135                 140

Ile Leu Phe Pro Lys Phe Gly Glu Tyr Asp Leu Val Leu Asn Pro Asp
145                 150                 155                 160

Ile Ile

<210> SEQ ID NO 43
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asn Lys Arg Met Lys Met Cys Pro Ala Cys Gln Gln Gly Tyr Leu
1               5                   10                  15

Tyr His Ser Lys Pro Lys Tyr Leu His Asp Glu Ile Ile Leu Cys Asp
            20                  25                  30

Glu Cys Asp Ala Val Trp Leu Lys Gly Met Asn Ile Phe Tyr Gly Glu
        35                  40                  45

Tyr Glu Lys Asp Phe Tyr Ser Tyr Val Pro Phe Met Glu Ser Gln Gly
    50                  55                  60

Ile Thr Ser Glu Cys Ile Trp Glu Gly Asp Leu Phe Asp His Pro Tyr
65                  70                  75                  80

Tyr Glu Asp Glu Asn Ser Asn Asp Met Asp
                85                  90

<210> SEQ ID NO 44
<211> LENGTH: 313
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Ser Ala Thr Glu Ile Glu Lys Ala Lys Ala Lys Ile Thr Ala Tyr
1               5                   10                  15

Ser Lys Leu Val Ala Gly Thr Ser Ala Val Val Gly Gly Asp Val
            20                  25                  30

Asn Thr Ala Ala Asn Ala Ala Gln Ile Ala Val Glu Asn Asn Thr Leu
        35                  40                  45

Tyr Pro Arg Cys Val Gly Ala Lys Cys Asp Glu Phe Gln Lys Glu Gln
    50                  55                  60

Gln Lys Trp Ile Arg Glu Asn Pro Glu Glu Tyr Arg Glu Val Leu Leu
65                  70                  75                  80

Phe Gln Thr Gly Phe Ile Pro Ile Ile Gly Asp Ile Gln Ser Phe Val
                85                  90                  95

Gln Ala Gln Thr Ala Ala Asp His Leu Phe Ala Leu Leu Gly Val Val
            100                 105                 110

Pro Gly Ile Gly Glu Ser Ile Gln Ala Tyr Lys Val Ala Lys Ala Ala
        115                 120                 125

Lys Asn Leu Gln Gly Met Lys Lys Ala Leu Asp Lys Ala Ala Thr Val
    130                 135                 140
```

```
Ala Thr Ala Gln Gly Tyr Val Ser Lys Thr Lys Ile Lys Ile Gly Gln
145                 150                 155                 160

Thr Glu Leu Arg Val Thr Ala Ala Thr Asp Lys Gln Leu Leu Lys Ala
                165                 170                 175

Ile Gly Glu Gly Arg Asp Thr Thr Gly Lys Met Thr Glu Gln Leu Phe
            180                 185                 190

Asp Ser Leu Ala Lys Gln Asn Gly Phe Arg Val Leu Ser Gly Gly Lys
        195                 200                 205

Tyr Gly Gly Asn Asn Gly Phe Asp His Val Trp Gln Ala Ala Asp Gly
210                 215                 220

Ser Val Val Leu Ile Val Glu Ser Lys Gln Ile Arg Asn Gly Thr Val
225                 230                 235                 240

Gln Leu Asn Pro Asn Gly Ala Gly Gly Tyr Thr Gln Met Ser Glu Asp
                245                 250                 255

Trp Ile Arg Gln Val Leu Asp Gln Leu Pro Asp Gly Ser Pro Ala Lys
            260                 265                 270

Ala Ala Val Phe Lys Ala Asn Lys Asn Gly Thr Leu Lys Thr Ala Ile
        275                 280                 285

Ala Gly Val Asp Arg Gln Thr Gly Lys Ala Val Ile Leu Pro Val Lys
290                 295                 300

Val Pro Ser Lys Thr Asn Ile Arg Arg
305                 310

<210> SEQ ID NO 45
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly His Asn Met Met Thr Thr Gln Lys Trp Tyr Glu His Ile Thr
1               5                   10                  15

Asn Val Ile Ile Gly Asn Thr Ala Asn Phe Asn Ser Gly Cys Leu Asp
                20                  25                  30

Ser Ile Asp Tyr Val Asp Glu Arg Lys Gly Val Pro Leu Ala Ala Met
            35                  40                  45

Gln His Ile Phe Met Asp Val Arg Ala Ala Ser His Ala Tyr Leu
        50                  55                  60

Phe Glu His Asp Leu Lys Lys Phe Lys Gln Tyr Ala Tyr Val Ala Gly
65                  70                  75                  80

Lys Leu Gly Val Leu Leu Ser Val Asn Ser Thr Asp Pro Glu Pro Phe
                85                  90                  95

Phe Phe Pro Cys Asp Met Leu Asn Ile Gln Asn Pro Met Phe Leu Met
            100                 105                 110

Leu Met Ser Asp Ser Pro Gln Leu Arg Glu Phe Leu Val Arg Asn Ile
        115                 120                 125

Asp Asn Ile Ala Asn Asp Thr Glu Ala Phe Ile Asn Arg Tyr Asp Leu
130                 135                 140

Asn Arg His Met Ile Tyr Asn Thr Leu Leu Met Val Glu Gly Lys Gln
145                 150                 155                 160

Leu Asp Arg Leu Lys Gln Arg Ser Glu Lys Val Leu Ala His Pro Thr
                165                 170                 175

Pro Ser Lys Trp Leu Gln Lys Arg Leu Tyr Asp Tyr Arg Phe Phe Leu
            180                 185                 190
```

```
Ala Phe Ala Glu Gln Asp Ala Glu Ala Met Lys Ala Ala Leu Glu Pro
        195                 200                 205
Leu Phe Asp Lys Lys Thr Ala Arg Met Ala Ala Lys Glu Thr Leu Ser
    210                 215                 220
Tyr Phe Asp Phe Tyr Leu Gln Pro Gln Ile Val Thr Tyr Ala Lys Ile
225                 230                 235                 240
Ala Ser Met His Gly Phe Asp Leu Gly Ile Asp Gln Glu Ile Ser Pro
                245                 250                 255
Arg Asp Leu Ile Val Tyr Asp Pro Leu Pro Ala Asp Glu Tyr Gln Asp
                260                 265                 270
Ile Phe Asp Phe Met Lys Gln Tyr Asp Leu Ser Tyr Pro Tyr Glu Tyr
                275                 280                 285
Leu Gln Asp Trp Ile Asp Tyr Tyr Thr Phe Lys Thr Asp Lys Leu Val
    290                 295                 300
Phe Gly Asn Ala Lys Arg Glu
305                 310

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gccaccggta cggaaactga a                                              21

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cctgaattca tgtctattcc attttgaaga                                     30

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccgagatctt taaccctttg ggcttaagcg a                                   31

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gggagatctc ccgctcgtgt tgtgcatta                                      29

<210> SEQ ID NO 50
<211> LENGTH: 28
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 50
aagagatctg cagccaaggc tctcgaaa                                        28

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gggagatctc aggctgccgc cgttga                                          26

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gggagatctc accccaagaa cgccaaaa                                        28

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gggagatctg aacgtatagt aatctatcca a                                    31

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gatcctcggt ga                                                         12

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
agcactctcc agcctctcac cgag                                            24

<210> SEQ ID NO 56
<211> LENGTH: 12
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 56
agtggctctt aa                                                              12

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agtggctggc                                                                 10

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
agcactctcc agcctctcac cgac                                                 24

<210> SEQ ID NO 59
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gatccgttca tg                                                              12

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
accgacgtcg actatccatg aacg                                                 24

<210> SEQ ID NO 61
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gtacttgctt aa                                                              12

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 62
gtacttgggc                                                            10

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
accgacgtcg actatccatg aacc                                            24

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aattctccct cg                                                         12

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
aggcaactgt gctatccgag ggag                                            24

<210> SEQ ID NO 66
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gatcaacttt tccctgtttg tcccattacc ggtttgaatg aaccgattgc gcgccgcgcg     60
tgttgttgga cattacctgc gattcagacg gtacgattga ccactacatc gaggagaacg    120
gcaatcaggg tacaatgcta                                                140

<210> SEQ ID NO 67
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gatccgcgta cttggttttt catattttgc atagtcttgt cggtcgggca tcttccccga     60
catcatctaa atttgtcttt attggttttt acgccactca ttgcggataa acaatattcc    120
gccttgccgt cgcgaatgtt caagctagcc tgcatcaccg taatcaggtt gcccgttacc    180
gagccttcga ga                                                        192
```

<210> SEQ ID NO 68
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gatccggctg cccgacgcgc gcaaaattgc cgccgaggaa agcgcgcaca accacgacgg      60
caaaaccagc gtatggcaat acaaacatct cgtgttcggt acggcaggca ttttctgcta    120
tgtcggcgcg gaggtgtcta tcggttcgtt gatggtcaac gtattgggtt atctgaaagg    180
gctggatc                                                             188

<210> SEQ ID NO 69
<211> LENGTH: 304
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gatcccccac tttacctcgg gcagattttg cgcgttcatt acaatagcgt atttatgcgt      60
ttgcgtttgc gcttgccgct gcccccccc cgccggtatg ggaaaacatc aatatggcgg     120
tataaagcgc ggtatggcgg aaaacctgcc gtttccaagt tttattcatc ttttattcct    180
tgagtttgcc ttcacgggac ggggcggcgc gcggaacgcg gggttcggta aaccgcccga    240
ttccgcgccc gccgaattgc tgattgaaaa gcttacttcc ccattttaac tttgcacact    300
gatc                                                                 304

<210> SEQ ID NO 70
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gatcagaccc attttcagcg caccgtaagc gcggattttc tcgaattttt ccaaagctgc      60
ggcatcgttg ttgatgtcgt cttgcaactc tttgcccgtg tagcccaagt cggcggcatt    120
caggaaaacg gtcggaatgc ccgcgttgat gagcgtggct ttcaaacggc ctatattcgg    180
cacatcaatt tcatcgacca aattgccggt tgggaacata ctgccttcgc cgtcggctgg    240
atc                                                                  243

<210> SEQ ID NO 71
<211> LENGTH: 236
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
cggcggcgta gtccgccgcg acagcgttac cataagcggg acagactaca cccctttatc      60
taacccgcaa agtttggata cggaattaaa atggttgctt caagaagctc ccgaaataga    120
aaatcctttc gaccgcgccg tttatctcca taataatttg gcgtatcttc aatattttaa    180
agattgcaat aaacgtactg ccagaaactg catgaccttg tcgctgatgc gctccg       236

<210> SEQ ID NO 72
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
cggtcaatca caagaaagtc agccgtctga tggcgaagac ggggctgaag gcagtgatat    60
ggcggcgcaa ataccgctcg ttcaaaggag aagtcggcaa aattgcgccg aatatcctgc   120
gacgctgttt ccatgcagaa aagccgaatg agaaatgggt aacggacgtt gccgagttca   180
atgtaggcgg agaaaagata tacctttctc cgattatgga tttgtttaac ggggaaatcg   240
tcagttaccg tattcagacc cgcccgactt tcgatttggc                         280

<210> SEQ ID NO 73
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
cggtcagaaa caggcaaggt aatgaaaatg cctgaggcac ggactgtgct gcgaacgaaa    60
actccttacc gaagtcttct atacccaggc tcaatagccg ctcaaggaga gagctatcat   120

<210> SEQ ID NO 74
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
cggtcagaaa caggcaaggt aatgaaaatg cctgaggcac ggactgtgct gcgaacgaaa    60
actccttacc gaagtcttct atacccaggc tcaatagccg ctcaaggaga gagctatcat   120

<210> SEQ ID NO 75
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
cggtgttttt cttaacaatt cgccgacttc atggcgatat ttaagtgaca gttgctccgc    60
ccacgcagtt gcgccgaact cagcaccacg acattatact gattatgcac atcggcaaga   120
tcaaactgac ctatcgtagt atcgcagact gt                                 152

<210> SEQ ID NO 76
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
cggggaggttt tgtgcatcct gataccgatc ggttgttgtt gctcaaagga cagaaggccg    60
ctgataaacg agattacctg tttgtcgcta ttgacgattt ttatactctg ccattttgcc   120
agacaaaacc gcagacagtg ctgccaagtt tctgaccgaa catctggccg acccctgctt   180
gtacctgatt gagtacgctt actctgacaa tgataggtaa tataaagagc cgtccaacat   240
gctttcggtg cagtttgtta tgataatggg attggttgga ggcttgcccg atttgcttgt   300
ccgcagacca acggtaaggc ggagcgggtt atccgtacct tgatggagat gtggcatgag   360
gaacagtcgt ttgacagacc g                                             381

<210> SEQ ID NO 77
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
cggagcataa aatcgttatt aaagataatg gtataggaac gagcttcgat gaaatcaatg    60 attttattt gagaatcggt cggaacagaa gggaagaaaa acaagcctcc ccgtgcggaa   120
gaattccaac gggtaaaaaa ggccttggta aattggcatt attcgggctt ggcaacaaaa   180
ttgaaatttc tactatccag ggaaacgaaa gggttacttt tactttggat tatgcagaga   240
ttcgaagaag caagggtatt tatcaaccg                                     269

<210> SEQ ID NO 78
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
cggatgaaaa cggcatacgc gccaaagtat ttacgaacat caaaggcttg aagataccgc    60
acacctacat agaaacggac gcgaaaaagc tgccgaaatc gacagatgag cagctttcgg   120
cgcatgatat gtacgaatgg ataaagaagc ccgaaaatat cgggtctatt gtcattgtag   180
atgaagctca agacgtatgg ccg                                           203

<210> SEQ ID NO 79
<211> LENGTH: 229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
cggtttcagg ttgtcgcgaa ggctcggtaa cgggcaacct gattacgggt gatgcaggca    60
gcttgaacat tcgcgacggc aaggcggaat atgtttatcc gcaatgagtg gcgtaaaaac   120
caataaagac aaatttagat gatgtcgggg aagatgcccg accgacaaga ctatgcaaaa   180
tatgaaaaac caagtacgcg gatcaggcat ggatgcacga tccaatccg               229

<210> SEQ ID NO 80
<211> LENGTH: 207
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 80
cgggtcgctt tattttgtgc aggcattatt tttcattttt ggcttgacag tttggaaata    60
ttgtgtatcg ggggggggta tttgctgacg taaaaaacta taaacgccgc gcaaaatatg   120
gctgactata ttattgactt tgattttgtc ctgcgcggtg atggataaaa tcgccagcga   180
taaagaattt gcgagaacct gatgccg                                       207

<210> SEQ ID NO 81
<211> LENGTH: 224
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
cggcaacgat ttgagctatc gcggttacga cattctggat ttggcacaaa aatgcgagtt    60
tgaagaagtc gcccacctgc tgattcacgg ccatctgccc aacaaattcg agctggccgc   120
ttataaaacc aagctcaaat ccatgcgcgg cctgcctatc cgtgtgatta agttttggga   180
aagcctgcct gcacataccc atccgatgga cgtaatgcgt accg                    224

<210> SEQ ID NO 82
<211> LENGTH: 212
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
cgggaacagc cattgcccac gcccacgccc cccaagaaag acggaaacta ctgcctaaat    60
tttcggcaat caagttgacg attaaagggt tgggggcagt tgcagtaata aacatagccg   120
acgaaatggg attggaatga tagttgacca aagccaaata tttacccatc ttgccttctg   180
tgccttttgc gggattggag ccgtaactgc cg                                 212

<210> SEQ ID NO 83
<211> LENGTH: 353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
cgggaattct gagcagaatg aaagaaagca ggcttgataa tttcataaag ttattggaag    60
aaaaaggatt taccgtccat ttcggtattc acaatacggc tgattacgga attccccaaa   120
gccgtaaaag atttacgtta attgcaaaca gaataaccaa agaaaagctg gaaccagtca   180
agtattcggg caaacggctt acggtagccg atgttttggg aatggaaatg gctttcccaa   240
cattattgca ggacaccaag acgaaacgga ttttatgcat agctgtgcgg gaattatctg   300
atatcacttg aacgattggc ttgatacgta aaaacggagg aaccgttggc ttt          353

<210> SEQ ID NO 84
<211> LENGTH: 308
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 84
aattccgtat ccaaactttg cgggttagat aaagggtgt agtctgtccc gcttatggta        60
acgctgtcgc ggcggactac gcccggagcc ttttccagt aagttttcgg aaatcaggct       120
gtgggtggtt tttaagaaat ccaaccagtc aaacggctcg gggctgtcca accggacac      180 aggtgccggt aactttccct caggttgatt aacattacgg catccgaata taacttcccg     240
cctgcggttt gcccgagttt aagcaatgcc tgcgtatcgt attgattata aagtgtttcc    300
ttccaatt                                                              308

<210> SEQ ID NO 85
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
aattcgtgtg ccgcgtcgac aaaccgctga cgtagcggat gtctcatgcc acgtttcaaa      60
gcaggttgat ggcggttagc aaccctctga tttcactggg atat                     104

<210> SEQ ID NO 86
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aattgcgtag agtgggcttc agccacgttt tttcttttc ggtcgttgat tggtgggctg       60
aaccacttgt ttcggaaatc cgtatcatg                                        89

<210> SEQ ID NO 87
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
aatttccacc tatgccctac gcagcgatta tccgtggttt acccaaaggg tgattatggc      60
aaaagcgcgg ggttgagcga ccgccttttg ttgccggcgt tcaaacgggt tttgatagga    120
aatgcaggca cgaagcctcg gctgattgtg atgcacctga tgggttcgca cagtgatttt    180
tgcacacgtt tggataagga tgcgcggcgg tttcagtatc aaactgaaaa aatatcctgc    240
tatgtttcca tcaatcgcgc aaaccgataa att                                 273

<210> SEQ ID NO 88
<211> LENGTH: 270
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
aattcttccg cacggggagg cttgtttttc ttcccttctg ttccgaccga ttctcaaata     60

```
aaaatcattg atttcatcga agttcattcc tataccatta tctttaataa cgattttatg    120
ctccggttta tcgaataacc taacttccac ttccgtagca catgcatcgt aggcattcgc    180
tatcaactcg gcaatcgcag gaacagtgtg cgaatacaat ctttacaccc aaatgttcga    240
ttacggttgg ctcgaaactc aatttcaatt                                    270
```

<210> SEQ ID NO 89
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
aattatgaac acacgcatca tcgtttcggc tgcgttcgtt gcgttggcat tagcaggttg     60
cggctcaatc aataatgtaa ccgtttccga ccagaaactt caggaacgtg ccgcgtttgc    120
cttgggcgtc accaatgccg taaaaatcag caaccgcagc aatgaaggca tacgcatcaa    180
ctttaccgca actgtgggta agcgcgtgac caatgctatg ttaccagtgt aatcagcaca    240
atcggcgtta ccacttccga tgcaatt                                       267
```

<210> SEQ ID NO 90
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
aattttattt tggttcgtag tcattttgtg caactgaacg atattcgttt tcatcattgc     60
taacgtctag tgcccattgt ggcccgtaat aagagatttc gtctcctttt acatgtttga    120
cgctgacggc atactgggga tcgatgacgg ataatgtacg tctgttgaca tctgcaacgc    180
taaatcaatc atcggtattg gataatgcgt tgccgatgtt ttgacttgta tgtt          234
```

<210> SEQ ID NO 91
<211> LENGTH: 295
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
aattcggccg gctgtgtcaa ataatgcgtt actttggccg ggtcttgttc tttgtaagtg     60
gtggtctttt tttgcgcgtt atccccatct gtttgagtgc atagcaaatg gtggctgccg    120
tacaatcaaa tgtttggcgt tcatgcagat aggcatcatg gtgttgccca atatattgag    180 ccggttttg cctatccgat ttgacggcat ttagaccggt aacttgatgt tttaagctgc     240
ctgtttgttt aaaggcgaat ccacaagtaa agcgtgtttc ttgacaggtt aaacg         295
```

<210> SEQ ID NO 92
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

-continued

```
aattgtgtat atcaagtagg atgggcattt atgcctgacc tacaaaacca aaaacaacct    60 accacccctta atcaactcca caaaccctct tcagacaacc tcgttttttg aaaaacaatc  120
tgtaaacaga taactgctga agaataccgt tgccgagccc caaaaccccgt actgcaactt  180 ttattgtgaa cttcccatta tgagaaaatc ccttttcgtc ctctttctgt attcgtccct  240
acttactgcc agcgaaatt                                                259

<210> SEQ ID NO 93
<211> LENGTH: 379
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
aattgcacca cgcgatgatg ggtacgcctc tgttgccatt gcgaccgccg ccgccgtgcc    60
cggtacgctg gtcaaccttg ccgcggcgga acgggtaaag aagtgcgctt cgggcatcct  120
tccggtacat tgcgcgtcgg tgcagcgccg aatgtcagga cggacaatgg acggccacca  180
aagcggttat gagccgcagc gcacgcgtga tgatggaagg ttgggtcagg gtgccggaag  240
attgttttta aattggacgg cgaaccggtc tattcgtatt ggcgttatac cgccgcaaag  300
gcagaccttg aaactggtgc gtgccgtgca gggcatgtac ggctatgtgt gcgtggcggg  360
cggatttgat gtgcggaat                                                379

<210> SEQ ID NO 94
<211> LENGTH: 308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
aatttgttgg gcagatggcc gtgaatcagc aggtgggcga cttcttcaaa ctcgcatttt    60
tgtgccaaat ccagaatgtc gtaaccgcga tacgtcaaat cgttgccggt acgcaacggt  120
acacaaagcg gtattaccgg ccgcaacgcc agaaagcgca acggatttt aggtttgagg  180 gtcggggttt gagtagtttc agtcatggta tttctccttt gtgtttttat gggtttcggg  240
ttttcagacg accgatgcgg atttgttgaa aggcagtctg aaagcggtaa atcattttg   300 aaacaatt                                                            308

<210> SEQ ID NO 95
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
aattcggagg agcagtaccg ccaagcgttg ctcgcctatt ccggcggtga taaaacagac    60
gagggtatcc gcctgatgca acagagcgat tacggcaact tgtcctacca catccgtaat  120
aaaaacatgc ttttcatttt ttcggcaagc aatgacgcac aagctcagcc caacacaact  180 gacccctattg ccatttttatg aaaaagacgc tcaaaaaggc attatcacag ttgcaggcgt  240
agaccgcagt ggagaaaagt tcaatggctc caaccattgc ggaatt                 286
```

```
<210> SEQ ID NO 96
<211> LENGTH: 238
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
aatttggata cgttggaaaa gggatatttg attgggaatg ggatgaagat aagcgtagat    60
gagttgggga aaaagtgtt agaacatatc ggtaagaatg aaccgttatt gttgaaaaat   120
ctactggtta acttcaatca gggaaaacat gaagaagtta ggaagttgat ttatcagttg   180
atagagttag attttctgga acttttgtga gggattctat gaaaaactgg aagcaatt     238

<210> SEQ ID NO 97
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
aattcggcac gcaggttttc taaaaaaagg ccgttgatga ctttgtcgat attggcggct    60
tcggtgtagt gcgcgcccgc ttcggccgct cttgcgcgtc catgacggat tggaagagcg   120
tgccgaagat ttctggactg atgttgcgcc agtcgaaatt gccgacacgg aggaatacc   180 tgccaacaag agtgcaggca gcgtaatcaa accaccccca cccgcaatcg catcgataaa   240
tccggcaatc atcgcaacca aacccaaagc gagtattatg tataaatctt ccatgtttct   300
taatcctgtt aacttgcacc aa                                            322

<210> SEQ ID NO 98
<211> LENGTH: 316
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
aatttgtcgg caatcttccc gggtcgcttt attttgtgca ggcattattt ttcatttttg    60
gcttgacagt ttggagatat tgtgtatcgg gggggggtat ttgctgacgt aaaaaactat   120
aaacgccgca gcaaaatatg gctgactata ttattgactt tgattttgtc ctgcgcggtg   180
atggataaaa tcgccagcga taaagatttg cgagaacctg atgccggcct gttgttgaat   240
attttcgacc tgtaattacg atttggcttc cgcgccggca caatatgccg ccaagcggcg   300
cccacatttt ggaagc                                                   316

<210> SEQ ID NO 99
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 99
aattcggaca gtatgaatac agcggattaa tacaaggtaa gttcattaca acggaaaaac        60
ctttaaagaa taatatgaaa ggtattacct tgtttgccaa cgggaatggt aaatatgccc       120
gagtttttca ctgaatagcg aatccagcca tttctattca tatttgactg gatggctgaa       180
tgtggacttt atagataatg acgatgaaga tttaatt                                217
```

DNA AND PROTEINS OR PEPTIDES SPECIFIC OF BACTERIA OF THE *NEISSERIA MENINGITIDIS* SPECIES, METHODS FOR OBTAINING THEM AND BIOLOGICAL APPLICATIONS THEREOF

This is a continuation of application Ser. No. 12/389,992 now abandoned (U.S. Patent Application Publication No. 2009-0305275 A1), filed Feb. 20, 2009, which is a continuation of application Ser. No. 11/638,579 (U.S. Patent Application Publication No. US 2007-0082361 A1), filed Dec. 14, 2006 (abandoned), which is a divisional of application Ser. No. 11/045,208 (U.S. Patent Application Publication No. US 2006-0063167 A1), filed Jan. 31, 2005, now abandoned which is a divisional of application Ser. No. 09/928,457, filed Aug. 14, 2001 (U.S. Pat. No. 7,029,845), which is a continuation of application Ser. No. 09/214,759, filed Apr. 22, 1999 (abandoned), which is a 371 application of PCT/FR97/01295, filed Jul. 11, 1997, and claims benefit of FR 96 08768, filed Jul. 12, 1996, the entire contents of each of which is hereby incorporated by reference.

The invention relates to DNAs and to proteins and peptides which are specific to bacteria of the species *Neisseria meningitidis* (abbreviated below to Nm), to the process for obtaining them and to their biological uses, in particular for the prevention and detection of meningococcal infections and meningitis.

It is known that Nm is one of the main agents of cerebrospinal meningitis.

Studies conducted in the United States have shown that 5 to 10% of the population are asymptomatic carriers of the Nm strain(s). The transmission factors of Nm are poorly known. For a proportion of persons infected, Nm penetrates the bloodstream, where it can cause meningococcaemia and/or progress to the cerebrospinal stream, to cause meningitis. Without fast antibiotic treatment, the infection can develop like lightning and become fatal.

Compared with other pathogens, Nm has the characteristic of being able to cross the haemato-encephalic barrier to colonize the meninges. The study of the pathogenicity of Nm is therefore important not only in the context of meningitis, but also in the context of any disease which affects the brain.

The benefit of having available tools specific to this species of bacteria for the uses envisaged above is therefore understood.

Genetically, Nm is very close to bacteria of the species *Neisseria gonorrhoeae* (abbreviated to Ng below) and of the species *Neisseria lactamica* (abbreviated to Nl below). However, their pathogenicity is very different.

Nm colonizes the nasopharynx, and then crosses the pharyngeal epithelium to invade the submucous space, thus being responsible for septicaemia and meningitis.

Ng is especially responsible for infections located in the genitourinary tract. It colonizes the genital mucosa, and then crosses the epithelium, subsequently invading the subepithelium, where it multiplies and is responsible for a severe inflammatory reaction. Disseminated gonococcal infections are possible, but remain rare and are the result of only some strains.

As regards Nl, it is considered that this is a non-pathogenic strain, since it is not responsible for a localized or general invasion.

A first consideration thus led to taking into account the fact that Nm and Ng, while being bacteria very close to one another, have different pathogenic potencies.

Since the genome of these bacteria has a high homology, only limited parts of the genome of Nm and Ng must code for specific virulence factors responsible for their pathogenesis.

It is clear that Nm has, compared with Ng, DNA sequences which are specific to it and which must be involved in the expression of its specific pathogenic potency.

The species Nm is subdivided into serogroups based on the nature of the capsular polysaccharides.

At least 13 serogroups have been defined, among which serogroups A, B and C are responsible for about 90% of meningitis cases. Groups A and C are found in epidemic forms of the disease. Group B is the serogroup generally isolated the most in Europe and the United States.

The capsule, which is present in Nm and absent from Ng, has served as the basis for formulating meningococcal antimeningitis vaccines.

The polysaccharides of the Nm capsule have been used to formulate a vaccine which has proved to be effective in preventing in adults the meningitis caused by meningococci of serogroups A, C, W135 and Y.

However, the polysaccharide of Nm group C has proved to be weakly immunogenic in children of less than two years, while the polysaccharide of NM group B is non-immunogenic in man and shares epitopes with adhesion glycoproteins present in human neuronal cells.

There is therefore no universal vaccine capable of preventing infections caused by all the serogroups of the meningococci and capable of responding to the intrinsic antigenic variability of bacterial pathogens in general and Nm in particular.

Because of the cross-reactivity of the Nm group B polysaccharide with human antigens, the multiplicity of the serogroups and the antigenic variability of Nm, the strategies proposed to date cannot lead to a vaccine which is effective in all situations.

Research is therefore concentrated on study of the characteristic elements responsible for the specificity of the meningococcal pathogenesis.

The majority of genes which have been studied in either of the two bacteria Nm or Ng have their homologue in the second bacterium.

In the same way, the majority of virulence factors identified to date in Nm have a counterpart in Ng, that is to say pilin, the PilC proteins, the opacity proteins and the receptors of lactoferrin and transferrin.

The specific attributes of meningococci characterized in the prior art are the capsule, the Frp proteins analogous to RTX toxins, Opc proteins of the external member, glutathione peroxidase, the porin PorA and the rotamase gene.

Among these, only the capsule is invariably present in the virulent strains of Nm. However, several extracellular pathogens have a capsule without nevertheless crossing the haemato-encephalic barrier.

Attributes which have not yet been identified must therefore be responsible for the specificity of the meningococcal pathogenesis. These attributes are probably coded by DNA sequences present among the meningococci but absent from the gonococci.

The inventors have developed a new approach based on subtractive isolation of Nm-specific genes, which genes must be linked to the specific pathogenesis of Nm, and more particularly to crossing of the haemato-encephalic barrier.

The subtractive method developed in the prior art has resulted in the production of epidemiological [sic] markers for some Nm isolates. These markers are of limited use: they do not cover all the serogroups of the Nm species.

In contrast to these studies, the work of the inventors has led, by confronting Nm with the entire Ng chromosome sheared in a random manner, to the development of a means for cloning all the DNAs present in Nm and absent from Ng, thus providing tools of high specificity with respect to Nm, and thus enabling the genetic variability of the species to be responded to for the first time.

The terms "present" and "absent" used in the description and claims in relation to the DNAs of a strain or their expression products are interpreted on the basis of identical hybridization conditions (16 h at 65° C., with NaPO$_4$ 0.5 M, pH 7.2; EDTA-Na 0.001 M, 1%, 1% bovine serum albumin and 7% sodium dodecylsulphate) using the same probe and the same labelling intensity of the probe, the same amount of chromosomal DNA and the same comparison element (chromosomal DNA of the homologous strain).

It is therefore considered that the DNA is present if the signal obtained with the probe is practically the same as that obtained with the reference strain.

Conversely, it is considered that the DNA is absent if this signal appears very weak.

A second consideration of the pathogenicities of Nm and Ng leads to taking into account their common capacity for colonization and penetration of the mucosa, and then invasion of the subepithelial space of the latter. It is highly probable that this process involves virulence factors common to the two pathogens. In this respect, it is known that a certain number of virulence factors have already been identified in Nm and in Ng, such as the pili proteins, PilC, the opacity proteins, the IgA proteases, the proteins for binding to transferrin and to lactoferrin, and the lipooligosaccharides.

The approach of the inventors is thus extended to investigation of the Nm regions which are specific to Nm and Ng but absent from the non-pathogenic species Nl, and in a general manner to investigation of the chromosomal regions of the DNAs and their expression products specific to a given species by the means developed in accordance with the invention.

The object of the invention is thus to provide DNAs of Nm specific to its pathogenic potency and means for obtaining them, in particular by formulating banks formed exclusively from these Nm-specific DNAs.

It also provides the products derived from these DNA sequences.

The invention also relates to the utilization of specific and exhaustive characteristics of these banks to formulate tools which can be used, in particular, in diagnostics, treatment and prevention.

The DNAs of the invention are characterized in that they are in all or part genes, with their reading frame, present in *Neisseria meningitidis*, but absent either from *Neisseria gonorrhoeae* and from *Neisseria lactamica*, with the exception of genes involved in the biosynthesis of the polysaccharide capsule, frpA, frpC, opc, por A, rotamase, the sequence 181106 (Accession No. Z 11857 in the EMBL/GenBank/DDBJ Nucleotide Sequence Data Libraries; see Knight et al., 1992, Molecular Microbiology 6(11): 1565-1573), IgA proteases, pilin, pilC, proteins which bind transferrin and opacity proteins.

As stated above, the terms "present" and "absent" are interpreted on the basis of the hybridization conditions used in the Southern blotting described in the examples and referred to above.

It can be seen that these DNAs include variants where these express a function intrinsic to the Nm species, more particularly a phenotype found solely in Nm or in common exclusively with Ng.

According to a main aspect, these DNAs are specific to the pathogenicity of *Neisseria meningitidis*, in spite of the genetic variability of this species.

According to an embodiment of the invention, the said DNAs are specific to Nm, in contrast to Ng.

More particularly, the Nm-specific DNAs are absent from *Neisseria lactamica* and from *Neisseria cinerea.*

Surprisingly, the majority of genetic differences between the strains of meningococci and those of gonococci appear grouped in distinct regions, which are said to correspond to the pathogenicity islets described previously for *E. coli* and *Y. pestis.*

In a preferred embodiment of the invention, these DNA are thus also characterized in that they comprise one or more sequence(s) present on the chromosome of *Neisseria meningitidis* Z2491 between tufA and pilT, or region 1 of the chromosome, and/or the sequence(s) capable of hybridizing with the above sequence(s), with the proviso of being specific to *Neisseria meningitidis.*

"Specific" in the description and the claims means the nucleotide sequences which hybridize only with those of Nm under the hybridization conditions given in the examples and referred to above.

In this respect, it can be seen that, in a general manner, when "all or part" of a sequence is referred to in the description and claims, this expression must be interpreted with respect to the specificity defined above.

Furthermore, all or part of a peptide or a fragment of a peptide or an antibody means a product having the biological properties respectively of the natural peptide or the antibody formed against the peptide.

Genes of the *Neisseria meningitidis* capsule are grouped in region 1.

DNAs of this type have a sequence corresponding in all or part to SEQ ID No. 9, 13, 22 or 30, and/or to any sequence located at more or less 20 kb from these SEQ ID on the chromosome of an Nm strain, and/or have a sequence which is capable of hybridizing with at least a fragment of any one of these sequences.

In another preferred embodiment of the invention, these DNA are also characterized in that they are made up of one or more sequence(s) present on the chromosome of *Neisseria meningitidis* Z2491 between pilQ and λ740, or region 2 of the chromosome, and/or the sequences(s) capable of hybridizing with the above sequence(s), with the proviso of being specific to *Neisseria meningitidis*

DNAs according to this embodiment have a sequence corresponding in all or part to SEQ ID No. 1, 2, 4, 6, 7, 10, 15, 31 or 34, and/or to any sequence located at more or less 20 kb from these SEQ ID on the chromosome of an Nm strain, and/or have a sequence which is capable of hybridizing with at least a fragment of any one of these sequences.

The invention especially provides all or part of the DNA sequence SEQ ID No. 35 of 15,620 bp, and the sequences corresponding to the open reading frames SEQ ID No. 37, SEQ ID No. 38, SEQ ID No. 39, SEQ ID No. 40, SEQ ID No. 41, SEQ ID No. 42, SEQ ID No. 43, SEQ ID No. 44 and SEQ ID No. 45.

In yet another preferred embodiment of the invention, these DNAs are also characterized in that they are made up of one or more sequence(s) present on the chromosome of *Neisseria meningitidis* Z2491 between argF and opaB, or region 3 of the chromosome, and/or the sequence(s) capable of hybridizing with the above sequence(s), with the proviso of being specific to *Neisseria meningitidis.*

DNAs according to this embodiment are characterized in that they have a sequence corresponding in all or part to SEQ ID No. 8, 21, 23, 25, 26, 28, 29, 32 or 35, and/or to any sequence located at more or less 20 kb from these SEQ ID on the chromosome of an Nm strain, and/or have a sequence which is capable of, hybridizing with at least a fragment of any one of these sequences.

Regions 1, 2 and 3 identified above have a high proportion of sequences specific to *Neisseria meningitidis* and also fall within the context of the invention.

Other DNAs representative of the specificity with respect to *Neisseria meningitidis* have one or more sequences which is/are present on the chromosome of *Neisseria meningitidis* Z2491 but are not part of regions 1, 2 and 3 defined above.

Such DNAs comprise one or more sequence(s) corresponding in all or part to SEQ ID No. 3, 5, 11, 12, 14, 16, 18, 19, 20, 24, 27 or 33, and/or to any sequence located at more or less 20 kb from these SEQ ID on the chromosome of an Nm strain, and/or have a sequence capable of hybridizing with such sequences.

Taking into account the uses envisaged in particular, the invention more specifically relates to the above DNAs involved in the pathogenesis of the bacterial organism.

In particular, it provides the DNAs corresponding to at least one of the characterizations given above and coding for a protein exported beyond the cytoplasmic membrane, and/or of which all or part of their sequence corresponds to the conserved region of the said DNAs.

According to another embodiment of the invention, the DNAs are thus common with those of Ng, but are absent from those of Nl.

These are more specifically the DNAs which are present on region 4 (arg J to reg F) or on region 5 (lambda 375 marker to pen A) on the chromosome of Nm Z2491 and/or are capable of hybridizing with the said DNAs present, with the proviso of being specific to Nm and Ng, in contrast to Nl.

“Specific to Nm and Ng in contrast to Nl” means the DNAs which hybridize with the DNAs of Nm and Ng under the hybridization conditions of the examples (see example 4 in particular).

The DNAs of regions 4 and 5 and those capable of hybridizing with these DNAs, with the proviso of expressing the intrinsic functions of Nm, have the advantage of intervening in a significant manner in the virulence of Nm, being involved in the stage of initial colonization and penetration and in the septicaemic dissemination.

According to other embodiments, the invention provides transfer and expression vectors, such as plasmids, cosmids or bacteriophages, comprising at least one DNA as defined above.

It also provides host cells transformed by at least one DNA as defined above.

Other host cells of the invention comprise genes or gene fragments specific to Nm, and are characterized in that their chromosome is deleted by at least one DNA according to the invention, in particular a DNA responsible for the pathogenicity. They are more specifically bacterial cells, in particular of Nm.

The invention also relates to the RNAs of which the sequence corresponds in all or part to the transcription of at least one DNA sequence or sequence fragment as defined above.

The invention also relates to the antisense nucleic acids of the DNAs as defined above, or of fragments of these DNAs.

These antisense nucleic acids carry, where appropriate, at least one substituent, such as a methyl group and/or a glycosyl group.

Other products which fall within the context of the invention include polypeptides.

These polypeptides are characterized in that they have an amino acid chain corresponding to all or part of a sequence coded by the nucleic acids defined above, or deduced from sequences of these nucleic acids.

They are advantageously polypeptides corresponding to all or part of the polypeptides exported beyond the cytoplasmic membrane, more specifically polypeptides corresponding to all or part of those coded by a conserved region.

As a variant, the polypeptides of the invention can be modified with respect to those corresponding to the nucleic acid sequences such that they are particularly suitable for a given use, in particular use as a vaccine.

Modification is understood as meaning any alteration, deletion or chemical substitution where this does not affect the biochemical properties of the corresponding natural polypeptides, more specifically of functional proteins exported at the periplasm and the external membrane.

Other products according to the invention include antibodies directed against the above polypeptides.

The invention thus provides polyclonal antibodies, and also monoclonal antibodies, characterized in that they recognize at least one epitope of a polypeptide as described above.

It also relates to fragments of these antibodies, more particularly the fragments Fv, Fab and Fab'2.

The invention also relates to the anti-antibodies which are capable of recognizing the antibodies defined above, or their fragments, by a reaction of the antigen-antibody type.

According to the invention, the various products considered above are obtained by a synthesis and/or biological route in accordance with conventional techniques.

The nucleic acids can also be obtained from banks made up of Nm-specific DNAs such as are formulated by a subtractive technique, this technique comprising:

- mixing of two DNA populations,
- realization of at least one subtractive hybridization-amplification iteration, and
- collection of the desired DNA or DNAs, followed, where appropriate, by its/their purification with elimination of redundant sequences.

According to the invention, the two DNA populations originate respectively from a strain of *Neisseria meningitidis*, the so-called reference strain for which the specific bank must be constructed, and a strain of *Neisseria*, the so-called subtraction strain, having a homology in primary DNA sequences of greater than about 70% with the *Neisseria meningitidis* strain, the DNA sequences of the subtraction and reference strains being obtained respectively by random shearing, and by cleavage by a restriction endonuclease capable of producing fragments less than about 1 kb in size.

The invention provides in particular a process for obtaining *Neisseria meningitidis*-specific DNA banks, comprising the stages of

- random shearing of the chromosomal DNA of a strain of *Neisseria gonorrhoeae*, the so-called Subtraction strain, in particular by repeated passage through a syringe,
- cleavage of the chromosomal DNA of a strain of *Neisseria meningitidis*, the so-called reference strain, preferably by a restriction enzyme producing fragments less than about 1 kb in size,
- splicing of the DNA fragments of the reference strain, cleaved by the restriction enzyme, with suitable oligonucleotide primers,
- realization of a subtractive hybridization-amplification iteration, by:
  - mixing of the two DNA populations under suitable conditions for hybridization of homologous sequences, and then amplification of auto-reannealed fragments and collection of these fragments, digestion of these fragments by a restriction enzyme and re-splicing with oligonucleotide primers, followed by a purification of the spliced DNA and, where appropriate, a new iteration of the subtractive hybridization, comprising mixing of DNA fragments of *Neisseria gonorrhoeae* sheared as indicated above with DNA fragments of *Neisseria meningitidis* produced by the preceding iteration, followed, if desired, by cloning of the DNAs of the bank.

The primers used are oligodeoxynuclectide primers which are suitable for the restriction endonuclease used and allow insertion into a cloning site, such as the EcoRI site of the plasmid pBluescript. Such primers will advantageously be chosen among the oligodeoxynucleotides referred to in the sequence listing under SEQ ID no. 36 to 45.

The banks thus obtained are formed from DNAs which are specific to meningococci and absent from gonococci.

The specificity of the DNAs was verified, as described in the examples, at each iteration by Southern blots, with genes common to the subtraction strain and to the reference strain, or with the total DNA of each of the strains digested by a restriction endonuclease, such as ClaI.

At each iteration, the exhaustivity of the DNA bank was also verified by Southern blotting with probes known to be specific to the reference strain, that is to say for *Neisseria meningitidis* the frp, opc and rotamase genes in particular.

The experiments carried out showed that the banks obtained by the process of the invention are deficient in genes having a significant homology with species of *Neisseria* other than *Neisseria meningitidis*, for example the ppk or pilC1 genes, generally in only 2 or 3 iterations.

If necessary, two routes, which are not exclusive of each other, can be taken.

It is possible to proceed with an $(n+1)^{th}$ iteration using the DNA of iteration n as the DNA population of the reference strain.

As a variant, a second bank independent of the first is constructed, with a restriction enzyme of different specificity to that used in the first bank, for example MboI.

In all cases, it is preferable to keep each of the products produced by each of the iterations performed.

The invention also provides the use of the subtractive technique described above to obtain banks of the DNAs common to Nm and Ng, but specific with respect to Nl.

Three different banks are advantageously constructed, two of them by digestion of the chromosomal DNA of Nm by MboI and Tsp5091, and the third by digestion of the chromosomal DNA of Nm with MspI. Two subtraction series allow the DNAs having the required specificity to be collected, as described in the examples.

The invention also relates to the process for obtaining these banks and the banks themselves.

It can be seen that, generally, the process of the invention can be used to obtain banks of DNAs specific to a given cell species, or to a given variant of the same species, where another species or another variant which is close genomically and expresses different pathogenic potencies exists.

Using the process of the invention, DNA banks specific to given species of *cryptococci, Haemophilus, pneumococci* or also *Escherichia coli*, or more generally any bacterial agent belonging to the same species and having different pathovars will advantageously be constructed.

Furthermore, from these banks the invention provides the means to have available virulence factors specific to a species or a given variant.

Such banks are therefore tools which are of great interest for having available attributes which are responsible for the specificity of a pathogen, this use being more specifically illustrated according to the invention by the obtaining of banks comprising the attributes responsible for the specificity of the meningococcal pathogenesis.

Study of the products of the invention, the nucleic acids, polypeptides and antibodies, has enabled an absolute specificity with respect of *Neisseria meningitidis*, regardless of the strain and its variability, to be demonstrated.

These products are therefore particularly suitable for diagnosis or prevention of infections and meningitis caused by *Neisseria meningitidis*, whether in adults or children and regardless of the serogroups of the strain in question.

The method for diagnosis, according to the invention, of a meningococcal infection, and more particularly of meningococcal meningitis, by demonstration of the presence of *Neisseria* meningitis in an analytical sample is characterized by the stages of:

bringing into contact a sample to be analysed, that is to say a biological sample or a cell culture, and a reagent formulated from at least one nucleic acid as defined above, if appropriate in the form of a nucleotide probe or a primer, or, as a variant, from at least one antibody or a fragment of an antibody as defined above, under conditions which allow, respectively, hybridization or a reaction of the antigen-antibody type, and detection of any reaction product formed.

If the reagent is formulated from a nucleic acid, this can be in the form of a nucleotide probe in which the nucleic acid or a fragment of the latter is labelled in order to enable it to be detected. Suitable markers include radioactive, fluorescent, enzymatic or luminescent markers.

As a variant, the nucleic acid is included in a host cell, which is used as the reagent.

In these various forms, the nucleic acid is used as such or in the form of a composition with inert vehicles.

If the reagent is compiled from an antibody, or a fragment of an antibody, this can be labelled for detection purposes. Most generally, a fluorescent, enzymatic, Most radioactive or luminescent marker is used.

The antibody or the antibody fragment used, which is labelled if appropriate, can be used as such or in the form of a composition with inert vehicles.

The sample used in the stage of bringing the components into contact is a biological sample produced by a mammal, such as cephalorachidian fluid, urine, blood or saliva.

The detection stage is carried out under conditions which allow the reaction product to be demonstrated when it is formed. Conventional means use fluorescence, luminescence, colour or radioactive reactions, or also autoriadography [sic] techniques. It is also possible to quantify the product.

The invention also relates to the labelled products, the nucleic acids and antibodies, as new products.

The method defined above can be used for diagnosis of an immune reaction specific to a meningococcal infection.

The reagent used is thus a polypeptide according to the invention, as coded by the said nucleic acid sequences, corresponding to the natural product or a polypeptide which is modified but has the biological and immunological activity of the corresponding natural polypeptide.

It is advantageously a polypeptide exported beyond the cytoplasmic membrane of *Neisseria meningitidis*, more particularly the part of such a polypeptide corresponding to the conserved region of the DNA.

The invention also relates to kits for carrying out the methods defined above. These kits are characterized in that they comprise:
- at least one reagent as defined above, that is to say of the nucleic acid, antibody or polypeptide type,
- products, in particular markers or buffers, which enable the intended nucleotide hybridization reaction or immunological reaction to be carried out, as well as use instructions.

The specificity of the products of the invention and their location on the chromosome of *Neisseria meningitidis* Z2491, either grouped in a region and able to be interpreted as pathogenicity islets, or isolated on the chromosome, impart to them a very particular interest for realization of vaccine compositions with a universal purpose, that is to say whatever the strain and the variability which it expresses. These compositions can include in their spectrum other prophylaxes, and can be, for example, combined with childhood vaccines.

The invention thus provides vaccine compositions which include in their spectrum antimeningococcal prophylaxis, intended for prevention of any infection which may be caused by *Neisseria meningitidis*, these compositions being characterized in that they comprise, in combination with (a) physiologically acceptable vehicle(s), an effective amount of polypeptides or anti-antibodies or their fragments as defined above, these products optionally being conjugated, in order to reinforce their immogenicity [sic].

Immunogenic molecules which can be used comprise the poliovirus protein, the tetanus toxin, or also the protein produced by the hypervariable region of a pilin.

As a variant, the vaccine compositions according to the invention are characterized in that they comprise, in combination with (a) physiologically acceptable vehicle(s), an effective amount:
- of nucleic acids as defined above,
- of transformed host cells as defined above, or
- of Nm cells, the chromosome of which has been deleted by at least one DNA sequence according to the invention involved in the pathogenicity of the bacterium. The nucleotide material used is advantageously placed under the control of a promoter of its expression in vivo and synthesis of the corresponding protein. To reinforce the immunogenicity, it is also possible to combine this nucleic material with a DNA or an RNA which codes for a carrier molecule, such as the poliovirus protein, tetanus toxin or a protein produced by the hypervariable region of a pilin.

The vaccine compositions of the inventions can be administered parenterally, subcutaneously, intramuscularly or also in the form of a spray.

Other characteristics and advantages of the invention are given in the examples which follow for illustration thereof, but without limiting its scope.

BRIEF DESCRIPTION OF THE DRAWINGS

In these examples, reference will be made to FIGS. 1 to 11, which show, respectively, FIGS. 9, 10 and 11: the reactivity of clones of the 3 subtractive banks with respect to Nm, Nl and Ng.

Figure 1:
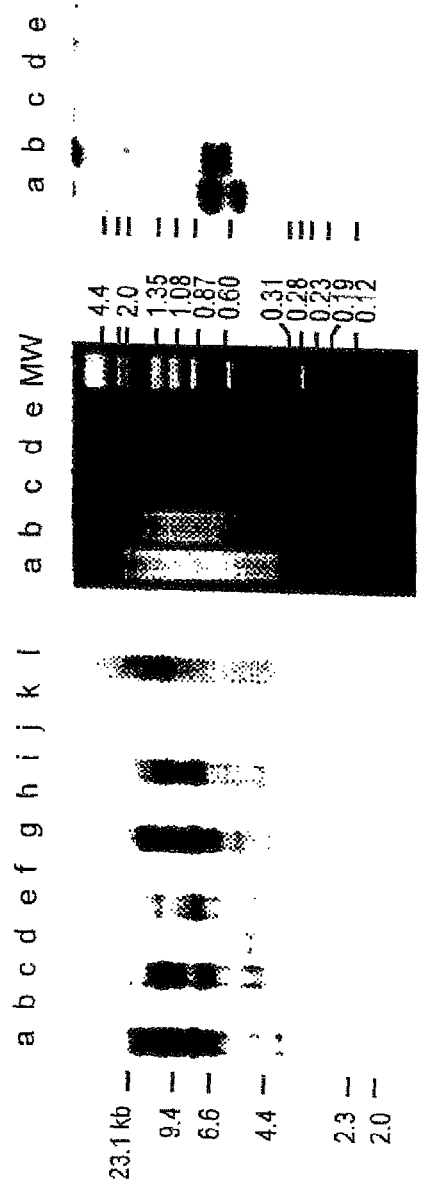
FIGS. 1A, 1B, 1C, 1D, 1E, 1F and 1G: analysis of the subtractive bank Tsp5091.

In the examples which follow, the following materials and methods were used:

Bacterial strains—To obtain the subtractive banks, strain Z2491 of Nm (Achtman et al., 1991, J. Infect. Dis. 164, 375-382), the strains MS11 (Swanson et al., 1974, Infect. Immun. 10, 633-644) and the strains 8064 and 9764 of Nl were used, it being understood that any other strain of the species in question could be used.

In order to verify the specificity of these banks, 6 strains of Nm, 4 strains of Ng, one strain of Nl (*Neisseria lactamica*) and one strain of Nc (*Neisseria cinerea*) were used.

The six strains of Nm are: Nm Z2491 of serogroup A, Nm 8013 of serogroup C (XN collection), Nm 1121, no serogrouping possible (XN collection), Nm 1912 serogroup A (XN collection), Nm 7972 of serogroup A (XN collection) and Nm 8216 of serogroup B (XN collection).

The four strains of Ng are: Ng MS11 (Pasteur Institute, Paris), Ng 403 (Pasteur Institute, Paris), Ng 6934 (Pasteur Institute, Paris), Ng WI (isolated from a disseminated gonococcal infection), Ng 401, Ng 6493 and Ng FA 1090.

The strains of Nl are Nl 8064 and Nl 9764 (XN collection), and that of Nc is Nc 32165 (XN collection).

Molecular Genetics Techniques

Unless indicated otherwise, the techniques and reagents used correspond to those recommended by Sambrook et al (Sambrook et al 1989, Molecular Cloning: A Laboratory Manual. Cold Spring Harbor Laboratory Press). The oligodeoxynucleotides used in this study are:

```
                                        (SEQ ID No. 54)
RBAm12, 3' AGTGGCTCCTAG 54

(SEQ ID No. 55)
RBam24, 5' AGCACTCTCCAGCCTCTACCGAG 3';

(SEQ ID No. 59)
Jbam12, 5' GATCCGTTCATG 3';

(SEQ ID No. 60)
JBAM24, 5' ACCGACGTCGACTATCCATGAACG 3';

(SEQ ID No. 56)
REco12, AGTGGCTCTTAA;

(=RBam 24, SEQ ID NO: 55)
REco24, 5' AGCACTCTCCAGCCTCTCACCGAG 3';

(SEQ ID No. 61)
JEco12, GTACTTGCTTAA;

(=JBam24, SEQ ID NO: 60)
JEco24, 5' ACCGACGTCGACTATCCATGAACG 3';

(SEQ ID No. 64)
NEco12, AATTCTCCCTCG;

(SEQ ID No. 65)
NEco24, AGGCAACTGTGCTATCCGAGGGAG;.
```

Transfer to Membranes (Southern Blots)

The transfers to membranes were effected by capillary transfers to positively charged nylon membranes (Boehringer Mannheim). The hybridizations were carried out at 65° C. in a solution comprising NaPi [sic] 0.5 M pH 7.2/EDTA 1 mM/SDS 7%/BSA 1%. The membranes were washed in a solution comprising NaPi [sic] 40 mM pH 7.2/EDTA 1 mM/SDS 1%. The final washing was carried out at 65° C. for 5 min.

The probe frp obtained with oligonucleotides based on the frpA sequence corresponds to 2.4 kb of the 5' end of the gene of the strain Z2491. The opc and rotamase probes corresponding to whole genes are produced from the strain Z2491 using oligonucleotides constructed on the basis of published sequences. The probes pilC1 and ppk (polyphosphate kinase) correspond to inserts of the plasmids pJL1 and pBluePPK6001 respectively.

EXAMPLE 1

Construction of Banks of DNAS Present in Nm and Absent from Ng a. "MboI" Bank

Construction—The DNA of Nm Z2491 was cleaved by the endonuclease MboI and subjected to two iterations of a method called CDA (comprehensive difference analysis) below. This method comprises subtractive hybridization in the presence of excess sheared DNA of Ng MS11 and amplification by PCR of those meningococcal sequences which, since they are absent from or do not have significant homology with the DNA of Ng MS11, could reanneal The chromosomal DNA of the strain Ng MS11 is sheared randomly by repeated passage through a hypodermic syringe until fragments of a size ranging from 3 to 10 kb are obtained. These DNA fragments are purified by extraction with phenol.

The chromosomal DNA of the strain Nm Z2491 is itself cleaved by the restriction endonuclease MboI. These DNA fragments (20 μg) are spliced with 10 nmol of annealed oligonucleotides RBam12 and RBam24. The excess primers are removed by electrophoresis over 2% agarose gel of low melting point. The part of the gel containing amplified fragments greater than 200 bp in size is excised and digested by β-agarase. These fragments are purified by extraction with phenol.

To carry out a subtractive hybridization (first iteration), 0.2 μg of the Nm DNA spliced with the RBam oligonucleotides is mixed with 40 μg Ng DNA in a total volume of 8 ml of a buffer EE 3× (a buffer EE 1× is composed of N-(2-hydroxyethyl) piperazine-N'-(3-propanesulphonic acid) 10 mM and EDTA 1 mM, and its pH is 8.0). This solution is covered with mineral oil and the DNA is denatured by heating at 100° C. for 2 min. 2 μl NaCl. 5 M are added and the mixture is left to hybridize at 55° C. for 48 h. The reaction mixture is diluted to 1/10 in a preheated solution composed of NaCl and buffer EE, and in then immediately placed on ice.

10 μl of this dilution are added to 400 μl of PCR reaction mixture (Tris.HCl pH 9.0 10 mM; KCl 50 mM; $MgCl_2$ 1.5 mM; Triton X100 0.1%; 0.25 mM of each of the four triphosphate deoxynucleotides; Taq polymerase 50 units per ml). The mixture is incubated for 3 min at 70° C. to complete the ends of the reannealed meningococcal DNA fragments.

After denaturing at 94° C. for 5 min and addition of the oligonucleotide RBam24 in an amount of 0.1 nmol per 100 the hybridizations are amplified by PCR (30 cycles of 1 min at 94° C., 1 min at 70° C. and 3 min at 72° C., followed by 1 min at 94° C. and 10 min at 72° C.; Perkin-Elmer GeneAmp 9600).

The amplified meningococcal fragments are separated from the primers and high molecular weight gonococcal DNAs on gel. They are digested by MboI and the oligonucleotides JLam12 and JBam 24 are spliced to them again. These spliced DNAs are again purified over gel and extracted with phenol.

A second iteration of the subtractive hybridization is carried out on 40 μg of the randomly sheared Ng DNA and 25 ng of the DNA spliced with the JBam oligonucleotides obtained from the first iteration of the subtractive hybridization. During this second iteration, amplification of the auto-annealed Nm DNA is effected with the aid of the oligonucleotide JBam24.

Specificity—In order to confirm their Nm specificity, the amplified sequences after the second iteration of the CDA method are labelled and used as a probe for the DNA digested by ClaI produced from a panel of six strains of *Neisseria meningitidis*, four of *Neisseria gonorrhoeae*, one of *Neisseria lactamica* and one of *Neisseria cinerea*.

The Southern blots obtained show that the amplified sequences resulting from the second iteration of the CDA method have a high reactivity with several bands corresponding to meningococci, and do not have a reactivity with the bands corresponding to the Ng, Nl and Nc strains.

The "MboI" bank thus appears to be Nm-specific.

Exhaustivity—In order to test the exhaustivity of the bank, all the products produced from the first and second iterations of the CDA method and also the initial chromosomal materials of Nm Z2481 [sic] and Ng MS11 are subjected to agarose gel electrophoresis, transferred to a membrane and brought into contact with probes comprising genes known to be meningococcus-specific, that is to say frp, opc and rotamase (Southern blotting).

As a result of these hybridizations, the Nm-specific gene frp is represented in the MboI bank by a fragment of 600 bp, but no activity is observed for the rotamase and opc genes. The MboI bank, although Nm-specific, therefore cannot be considered exhaustive.

Given their high specificity, the fragments produced by the second iteration of the CDA method for the MboI bank can nevertheless be cloned on the BamHI site of the plasmid pBluescript.

A sequence corresponding to any of the Nm-specific genes can be included in the subtractive bank only if it is carried by a restriction fragment of appropriate size. This condition is a function of two factors. Firstly, the probability that the largest fragments are entirely Nm-specific is low. Secondly, even if such fragments existed, they would be under-represented in the bank because of the limitations of the PCR technique, the amplification effectiveness of which decreases with increasing size of the fragments. Fragments greater that about 600 bp in size are not included in the bank. Because of the absence of Mbo fragments of suitable size from the chromosome of Nm Z2491, the rotamase and opc genes cannot be included in the bank. Any enzyme cannot by itself produce a small fragment corresponding to any Nm-specific gene. A second bank was therefore constructed using another restriction enzyme with a different specificity: Tsp509 [sic].

b. "Tsp5091" Bank

Construction—The enzyme Tsp5091 has the advantage of producing fragments of smaller size (less than about 1 kb) than the enzyme MboI.

Tsp5091 recognizes the sequence AATT and leaves, projecting at 5', a sequence of 4 bases compatible with EcoRI. The oligonucleotides used are Reco, Jeco and NEco.

The method followed conforms with that followed for construction of the "MboI" bank described above. However, higher quantities of meningococcal DNA were used for the first iteration of the subtractive hybridization in order to compensate for the higher number of fragments of low molecular weight produced by Tsp509I. For the first iteration, 400 ng Nm DNA fragments and, in the second, 25 ng Nm fragments are subjected to subtractive hybridization with 40 µg randomly sheared Ng DNA.

For the construction of this "Tsp5091I" bank, as a control, a third iteration of the subtractive hybridization is carried out using 40 µg sheared Ng DNA and 0.2 ng Nm fragments resulting from a digestion by Tsp509I and a resplicing, with NEco adaptors, of the fragments obtained as a result of the second iteration.

Specificity—As described for the previous bank, the product resulting from the second iteration of the CDA method is labelled and used as the probe for a panel of strains of Neisseria.

FIG. 1A illustrates the Southern blot hybridization of products of the second iteration of the CDA method' with the DNA digested by ClaI of: Nm in track a, Ng MS11 in track b, Nm 8013 in track c, Ng 403 in track d, Nm 1121 in track e, Ng 6934 in track f, Nm 1912 in track g, Ng WI (strain DGI) in track h, Nm 7972 in track i, N18054 in track j, Nc 32165 in track k, Nm 8216 in track 1.

In contrast to the high reactivity observed with all the Nm strains, a low or no reactivity is observed with the Ng, Nl and Nc strains.

The specificity of the bank was studied earlier by reacting membrane transfers (Southern blots) of the products produced by each of the three iterations of the CDA method with probes corresponding to pilC1 and ppk. These two genes are common to Nm and Ng.

FIG. 1B shows an agarose gel after electrophoresis of the chromosomes of Nm Z2491 and Ng Ms11, digested by Tsp509 [sic], and products resulting from each of the iterations of the CDA method.

In track a 1 µg of the chromosome of Nm was deposited, in track b 1 µg of that of Ng, in track c 0.15 µg of the products resulting from the first CDA iteration, in track d 0.1 µg of those of the second iteration, in track e 0.05 µg of the third iteration, MW representing the molecular size markers.

FIGS. 1C and 1D show gels obtained as described in FIG. 1B after transfer to the membrane (Southern blots) and hybridization with pilC1 (FIG. 1O) and ppk (FIG. 1D).

At the end of the second iteration of the CDA method, the sequences corresponding to the pilC1 and ppk genes are completely excluded from the bank.

Exhaustivity—The exhaustivity of the bank was examined by reacting the products resulting from the subtractive hybridization with the probes corresponding to three Nm-specific genes (frp, rotamase and opc).

These Nm-specific probes react with the amplification products resulting from the first and second iteration of the subtractive hybridization.

FIGS. 1E, 1F and 1G show gels obtained as described in FIG. 1B after transfer to the membrane (Southern blots) and hybridization with frpA (FIG. 1E), rotamase (FIG. 1F) and opc (FIG. 1G).

However, a third iteration of the subtractive hybridization leads to the loss of Nm-specific sequences, since the fragments which react with the rotamase and opc genes are absent from this third iteration.

In consideration of all these data, it emerges that the products resulting from the second iteration of the CDA method are Nm-specific and also constitute an exhaustive bank of Nm-specific sequences.

The products resulting from this second iteration are cloned at the EcoRI site of the plasmid pBluescript.

The bank produced by Tsp509I is more exhautive [sic] than the bank produced by MboI, as the theory considerations based on the enzymatic production of smaller restriction fragments would suggest.

In accordance with this aspect, it should be noted that the Tsp509I bank is less redundant than the MboI bank, that is to say it comprises less duplication of clones. 86% of the clones of the Tsp509I bank correspond to distinct sequences, while only 43% of the clones correspond to distinct sequences in the MboI bank (data not shown).

The bank produced by Tsp509I thus constitutes a source of Nm-specific clones.

EXAMPLE 2

Analysis of the Clones of the Subtractive Bank

Cloning and Sequencing of the Nm-Specific DNAs

The DNAs of the subtractive banks are clones at the BamHI (MboI bank) or EcoRI (Tsp509I bank) site of the plasmid pBluescript, and then transformed in DH5α of E. coli. The inserts are amplified by PCR carried out on the transformed colonies using the primers M13-50 and M13-40, the latter primer being biotinylated on its 5' end.

Sequencing was carried out on each PCR product after separation of the biotinylated and non-biotinylated strands using the system of Dynabeads M-280 with streptavidin (Dynal, Oslo). The sequences are screened according to their homologies with previously published sequences using the computer programs Blastn and Blastx (NCBI, USA and Pasta).

The PCR products resulting from the transformed bacteria colonies after using the primers M13-40 and M13-50 as described above were labelled by incorporation with random priming of $\alpha$-$^{32}$P-dCTP and were used as a probe for the membrane transfers of the chromosomal DNA digested by ClaI of strains Nm Z2491 and Ng MS11, as described above, in order to verify their specificity.

Mapping of Clones on the Chromosome of the Strain Nm Z2491.

The results of studies carried out with 17 clones of the "MboI" bank (designated by the letter B) and 16 clones of the "Tsp5091" bank (designated by the letter E), each of these clones having a unique sequence and being without counterpart in Ng, are reported.

The positions of the DNA sequences corresponding to cloned Nm-specific products were determined with respect to the published map of the chromosome of Nm Z2491 (Dempsey et al. 1995, J. Bacterial. 177, 6390-6400) and with the aid of transfers to membranes (Southern blots) of agarose gel subjected to pulsed field electrophoresis (PFGE).

The Nm-specific clones are used as probes for a hybridization on membranes (Southern blots) of the DNA of Nm Z2491 digested with enzymes of rare cutting sites, that is to say PacI, PmeI, SgfI, BglII, SpeI NheI and SgfI.

The gels (20×20 cm) were gels of 1% agarose in a buffer TBE 0.5× and were subjected to electrophoresis at 6 V/cm for hours according to pulsation periods varying linearly between 5 and 35 seconds.

The hybridizations on the membrane (Southern blots) were carried out as described above.

Figure 2:
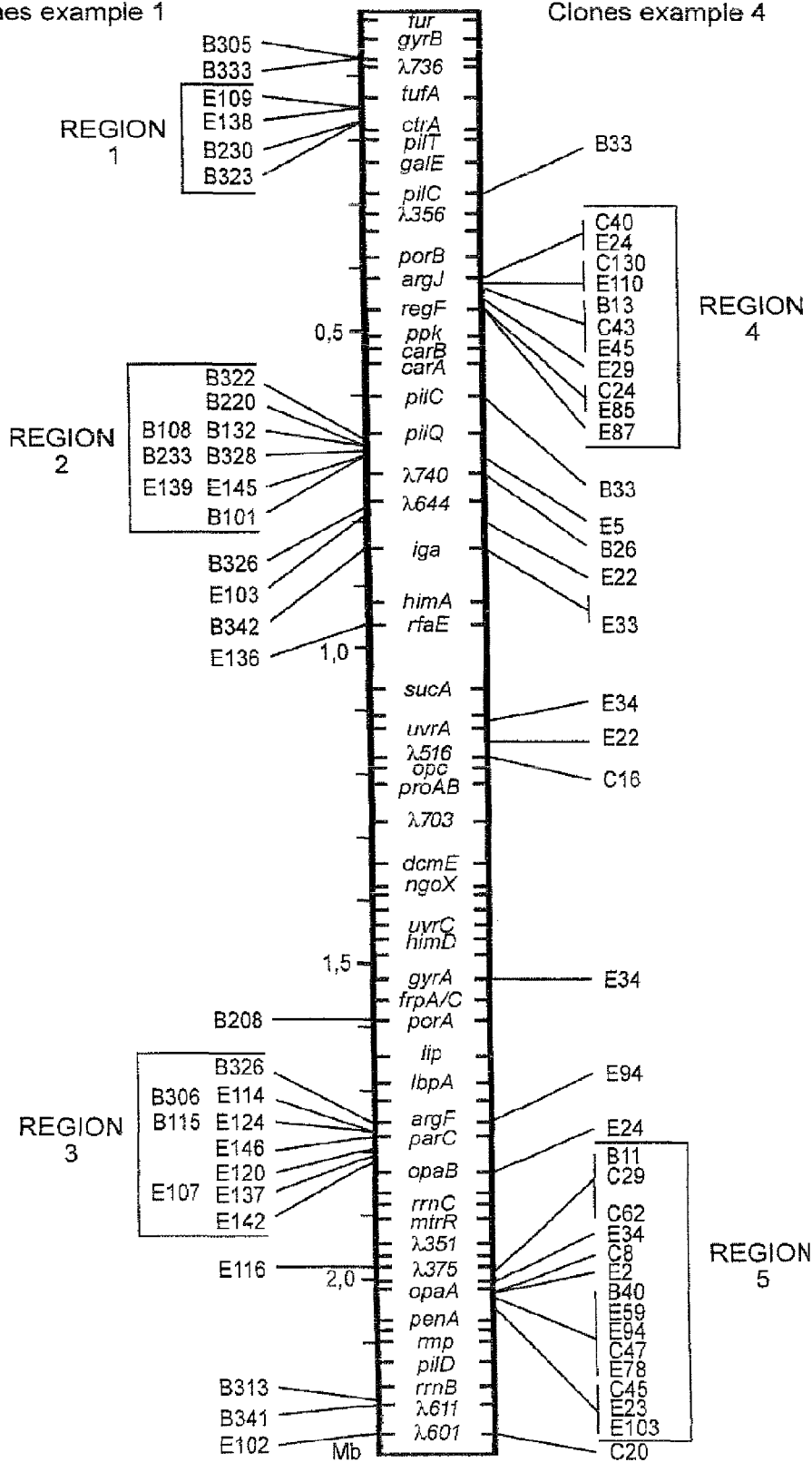
FIG. 2: the distribution of the Nm-specific sequences, in contrast to Ng, on the chromosome of the strain Z2491 (left-hand part) and of Nm-specific sequences, in contrast to Nl (right-hand part)

The results obtained are shown on FIG. 2: the reactivity was located by comparison with the positions of the fragments of corresponding size on the published map. The positions of all the genetic markers mapped by Dempsey et al (mentioned above) are visualized with the aid of points on the linear chromosomal map. The Nm-specific genes disclosed previously are labelled with an asterisk. The two loci called "frp" correspond to the frpA and frpC genes. The "pilC" loci correspond to the pilC1 and pilC2 genes, which are pairs of homologous genes and are not distinguished on the map. The accuracy of the positions of the Nm-specific clones of the invention depends on the overlapping of reactive restriction fragments. On average, the position is +/−20 kb.

This mapping reveals a non-random distribution of the Nm-specific sequences. The majority of the Nm-specific sequences belong to three distinct groups. One of these groups (region 1) corresponds to the position of genes relating to the capsule which have been described previously.

A distinction is made between:
 E109, E138, B230 and B323 as being region 1,
 B322, B22O, B108, B132, B233, B328, E139, E145 as B101 as being region 2, and
 B306, E114, E115, E124, E146, E120, E107, E137 and 142 as being region 3.
63% of the sequences identified as specific to meningococci are located inside these three distinct regions.

This grouping contrasts with the distribution of previously disclosed Nm-specific genes (frpA, frpC, porA, opc and the region relating to the capsule).

This prior art would suggest in fact that the Nm-specific genes, with the exception of functional genes relating to the capsule, were dispersed along the chromosome.

Mapping of Nm-specific sequences on the chromosome leads to an unexpected result with regard to the prior art.

The majority of the genetic differences between the meningococcal and gonococcal strains tested are grouped in three distinct regions.

Meningococcal genes relating to the capsule are grouped in region 1.

The function of genes of the other regions is unknown, but homologies with published sequences (table 1) suggest similarities between certain genes of region 3 and bacteriophage transposase and regulatory proteins. No meningococcal virus has been characterized and it is tempting to think that these sequences are of phagic origin. Interestingly, the genome of *H. influenzae* also contains a sequence homologous to that of the Ner regulatory protein of phage Mu, but it is not known if it is a functional gene.

The clone B208 has a high homology (48% identical, 91% homology for 33 amino acids) with a clone of conserved regions field III) in the class of proteins which bind to TonB-dependent ferric siderophors.

The proximity of this clone with the Nm-specific porA genes and the frp genes regulated by iron, and in particular the possibility that it is an Nm-specific receptor protein exposed on the external membrane in itself is a good candidate for further research.

The clone B339 corresponds to the Nm-specific insertion sequence IS1106.

The low homology between the clone B134 and the *Aeromonas* insertion sequence and also the presence of multiple copies of the clone B134 among the various strains of Nm suggest that it could be a new type of Nm-specific insertion sequence.

The possibility that the regions containing the Nm-specific clones could correspond to pathogenicity islets as described previously for *E. coli* and *Y. pestle* is of particular interest.

The clones isolated in this invention will allow better understanding of the relevance of Nm-specific regions in allowing cloning and sequencing of larger chromosomal fragments, and directly by their use for loci mutations.

Finally, detection of meningococcus-specific genes possibly involved in the pathogenicity of the organism allows targeting of suitable antigens which can be used in an anti-meningococcal vaccine.

The effectiveness and the speed of the method according to the inventions enables it to be used in a large number of situations for which the genetic differences responsible for a phenotype peculiar to one of 2 close pathogens are investigated.

Study of the Reactivity of the Clones of Regions 1, 2 and 3 Towards a Panel of Strains of *Neisseria*.

The PCR products corresponding to inserts of each of the clones were collected and used as probes for hybridization on membranes (Southern blots) for a panel of strains of Nm, Ng, Nl and Nc.

Regions 1 and 2 produce a limited number of bands for each of the meningococci. This suggests that these regions are both Nm-specific and common to all the meningococci.

Figures 3A, 3B, 3C:
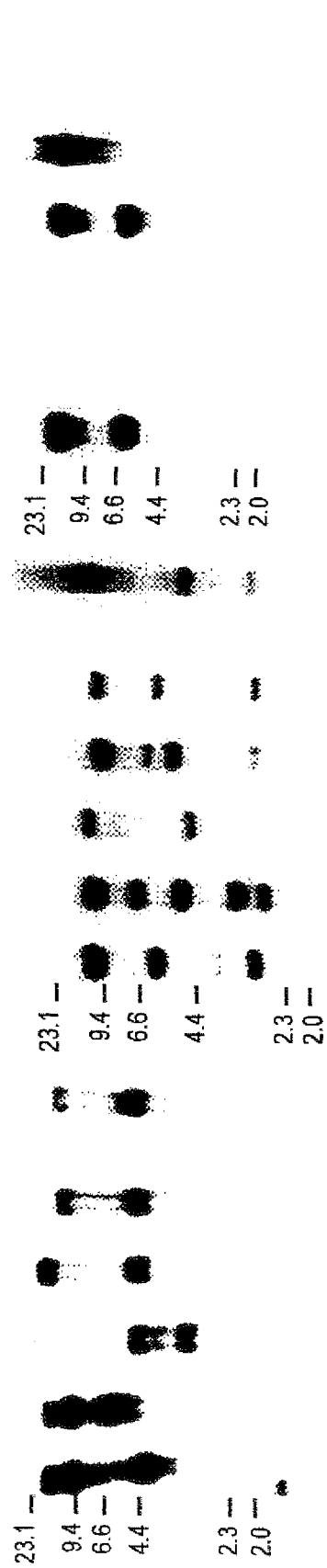
FIG. 3A to 3C: the reactivity of the clones of the 3 regions of the chromosome according to the invention towards a panel of strains of the genus *Neisseria*.

FIG. 3 illustrates the reactivity of the clones of regions 1, 2 and 3 towards a panel of neisserial strains. The clones of regions 1 (FIG. 3A), 2 (FIG. 3B) and 3 (FIG. 3C) taken together were used as probes towards a panel of meningococci, gonococci and towards a strain of Nl and Nc.

The tracks are as follows: DNA of; Nm Z2491 in track a, of Ng MS11 in track b, of Nm 8013 in track c, of Ng 403 in track d, of Nm 1121 in track e, of Ng 6934 in track f, of Nm 1912 in track g, of Ng WI (strain DGI) in track h, of Nm 7972 in track i, of Nl 8064 in track j, of Nc 32165 in track k, and of Nm 8216 in track 1.

Remarkably, region 3 has reactivity only with the meningococci of serogroup A. This region 3 is therefore specific to a sub-group of Nm.

A comparison was made with the known sequences in the databanks in order to evaluate the possible functions of the cloned regions.

Table 1 which follows gives the positions of specific clones on the chromosomal map and the homologies with known sequences.

TABLE 1

Position of specific clones on the chromosomal map and homologies with known sequences

| Name of clone* | Size of insert | Pac | Reactive fragments Pmc | Bgl | Spe | Nhe | Sgf | Position on Z2491 | Homologies of protein sequences |
|---|---|---|---|---|---|---|---|---|---|
| B305 | 259 | 18-20 | 15-17 | 22-23 | 18 | 11-13 | 2 | λ736 | |
| B333 | 235 | | 15-17 | 22-23 | 18 | 11-13 | 2 | λ736 | |
| E109[1+] | 211 | | 6-7 | 11-15 | 10 | 11-13 | 2 | tufA ctrA | protein LipB *N. meningitidis* (3 × 10$^{-26}$) |

TABLE 1-continued

Position of specific clones on the chromosomal map and homologies with known sequences

| Name of clone* | Size of insert | Reactive fragments | | | | | Position on Sgf Z2491 | Homologies of protein sequences |
|---|---|---|---|---|---|---|---|---|
| | | Pac | Pmc | Bgl | Spe | Nhe | | |
| E138[1+] | 315 | 1 | 6-7 | 11-15 | 10 | 11-13 | 2 tufA ctrA | protein LipB *N. meningitidis* ($4 \times 10^{-75}$) |
| B230[1] | 356 | 1-3 | 6-7 | 1 | 10 | 11-13 | 2 ctrA | protein KpsC *E. coli* ($3 \times 10^{-53}$) |
| B323[1] | 363 | 1 | 6-7 | 1 | 10 | 11-13 | 2 ctrA | protein CtrB *N. meningitidis* ($2 \times 10^{64}$) |
| B322[2] | 210 | | 2 | 16-18 | 6 | 1 | 5 pilQ/λ740 | HlyB *S. marcescens* ($4 \times 10^{-15}$) |
| B220[2] | 341 | | 2 | 16-18 | 6 | ≧18 | 5 pilQ/λ740 | |
| B108[2] | 275 | | 2 | 19-21 | 6 | >18 | 5 pilQ/λ740 | |
| B132[2] | 411 | 2 | 2 | 19-21 | 6 | ≧18 | 5 pilQ/λ740 | |
| B233[2] | 164 | 1-3 | 2 | 19-21 | 6 | ≧18 | 5 pilQ/λ740 | |
| B328[2] | 256 | 1-3 | 2 | 22-23 | 6 | ≧18 | 5 pilQ/λ740 | |
| E139[2] | 324 | 2 | 2 | 19-21 | 6 | ≧18 | 5 pilQ/λ740 | |
| E145[2] | 343 | 2 | 2 | 19-21 | 6 | ≧18 | 5 pilQ/λ740 | |
| B101[2] | 254 | ≧20 | 2 | 19-21 | 6 | ≧18 | 5 pilQ/λ740 | |
| E103q | 334 | | 2 | 11-15 | 3-5 | 10 | 3 λ644 | |
| B326[§] | 314 | | 2 | 11-15 | 3-4 | 10 | 3 λ644 | |
| B326 (low reactivity) | | | 5 | 6 | 16 | 2 | 1 argF | |
| B342 | 167 | | 2 | 19 | 3-4 | 6-7 | 3 iga | |
| E136 | 249 | | 2 | 7 | 1 | 3 | 3 lepA | |
| B208 | 177 | | 1 | 2 | 3-4 | 2 | 1 porA | FeIII pyochelin receptor *P. aeruginosa* ($5 \cdot 10^{-4}$) |
| = B306[3#] | 219 | 11 | 5 | 11-12 | 5 | 2 | 4 parC | |
| E114[3] | 227 | 11 | 5 | 11-12 | 5 | 2 | 4 parC | |
| E115[3#] | 251 | | 5 | 11-15 | 5 | 2 | 4 parC | |
| E124[3] | 208 | | 5 | 11-12 | 5 | 2 | 4 parC | |
| E146[3] | 146 | | 5 | 11-15 | 5 | | 4 parC | |
| E120[3] | 263 | | 5 | 3-4 | 5 | 16 | 4 opaB | |
| E107[3] | 248 | 11 | 14-17 | 3-4 | 5 | 16 | 4 opaB | |
| E137[3] | 274 | | 14-17 | 3-4 | 5 | 16 | 4 opaB | Transposase Bacteriophage D3112 ($6 \times 10^{-12}$) |
| E142[3] | 230 | | 14-17 | 3-4 | 5 | 16 | 4 opaB | Protein Ner-Like *H. influenzae* ($6 \times 10^{-23}$) Protein binding to the DNA Ner, phage mu ($3 \times 10^{-18}$) |
| E116 | 379 | 5-7 | 11-13 | 3-4 | 2 | 6-7 | 8 λ375 | |
| B313 | 436 | 9 | 9 | 3-4 | 13-14 | 5 | 2 λ611 | |
| B341 | 201 | 8-10 | 9 | 3-4 | 13-14 | 5 | 2 λ611 | |
| E102 | 238 | | 11-13 | 3-4 | 19 | 5 | 2 λ601 | |
| B134 | 428 | | | multiple | | | | Hypothetical protein H11730 *H. influenzae* ($7 \times 10^{-24}$) |
| B339 | 259 | | | multiple | | | | transposase ISAS2 *Aeromonas salmonicida* ($5 \times 10^{-5}$) transposase IS 1106 *N. meningitidis* ($6 \times 10^{-45}$) |

The level of homologies found, as given by the Blastx program, are indicated in parentheses
*The clones labelled with the index "1", "2" or "3" belong to regions "1", "2" or "3" respectively of the chromosome of *N. meningitidis* Z2491.
[+]E109 and E138 are contiguous clones
[§]B306 and E115 overlap
[#]B236 also has a low reactivity in the region of arg F
q) Clone E103 contains a Tsp509 I site and can therefore contain two inserts; however, since it reacts only with a single fragment ClaI (Oks) of the chromosome of *N. meningitidis* Z2491 and occupies only one position on the map, this clone is included here.

Firstly, it can be seen that the clones of region 1 all correspond to genes involved in biosynthesis of the capsule. These genes have previously been studied among the Nm of serogroup B (Frosch et al., 1989, Proc. Natl. Acad. Sci. USA 86, 1669-1673 and Frosch and Muller 1993, Mol. Microbiol. 8 483-493).

With the exception of a low homology with the haemolysin activator of *Serratia marcescens*, the clones of region 2 have no significant homology with published sequences, either in the DNA or the proteins.

Two of the clones of region 3 have interesting homologies with proteins which bind to the DNA, in particular the bacteriophage regulatory proteins and transposase proteins.

Clone B208 has a high homology with one of the conserved regions in one class of receptors (TonB-dependent ferric siderophor).

Clones B134 and B339 hybridize with several regions of the chromosome (at least 5 and at least 8 respectively).

Data relating to the sequences show that clone B339 corresponds to the Nm-specific insertion sequence S1106.

The translation of the clone B143 has a limited homology with the transposase of an *Aeromonas* insertion sequence (SAS2) (Gustafson et al. 1994, J. Mol. Biol. 237, 452-463). We were able to demonstrate by transfer on a membrane (Southern blots) that this clone is an Nm-specific entity present in multiple copies in the chromosomes of every meningococcus of the panel tested.

The other clones have no significant homology with the published neisserial sequences, and furthermore nor with any published, sequence. These clones therefore constitute, with the majority of the other clones isolated, a bank of totally new Nm-specific loci.

EXAMPLE 3

Study of Region 2 of the Nm Chromosome

Determination and Characterization of the Sequence of Region 2

PCR amplification is carried out with the chromosomal DNA of strain Z2491 of serogroup A, sub-group IV-1 using oligonucleotide primers formulated from each of the sequences of clones of region 2 in several different combinations. The PCR products which overlap are sequenced from the 2 strands using the chain termination technique and automatic sequencing (ABI 373 or 377).

To prolong the sequence beyond the limits of the clones available, partial SauIIIA fragments of 15 kb of the strain Z2491 are cloned Lambda DASH-II (Stratagene).

The phages containing the inserts overlapping region 2 are identified by hybridization with clones of this region as probes. The DNA inserted is sequenced from the ends of the inserts, and these sequences are used to formulate new primers which will serve to amplify the chromosomal DNA directly, and not the phagic DNA.

An amplification of the chromosomal DNA is obtained using these new primers and those of the sequence previously available.

These PCR products are also sequenced from the 2 strands, which leads to a complete sequence of 15,620 bp (SEQ ID No. 36) The reading frames of this sequence which start with ATG or GTG and are characterized by a high codon usage index are analysed.

This analysis reveals 7 ORFs of this type which fill the major part of the sequence of 15,620 bp. The positions of these ORFs are the following:
ORF-1: 1330 to 2970 (SEQ ID No. 37); ORF-2: 3083 to 9025 (SEQ ID No. 38); ORF-3: 9044 to 9472 (SEQ ID No. 39); ORF-4: 9620 to 12118 (SEQ TD No. 40); ORF-5: 12118 to 12603 (SEQ ID No. 42); ORF-6: 12794 to 13063 (SEQ ID No. 43); ORF-7: 13297 to 14235 (SEQ ID No. 44); and ORF-8: 14241 to 15173 (SEQ ID No. 45).

ORF-4 starts with the codon GTG and overlaps a slightly smaller ORF (SEQ ID No. 41) in the same reading frame (10127-12118, frame 2), which starts with the codon ATG.

ORF-4 codes for a protein which has structural homologies with a family of polypeptides comprising pyocins (*Pseudomonas aeruginosa*), colicins and intimins (*Escherichia coli*), which are bactericidal toxins (pyocins, colicins) or surface proteins involved in adhesion of bacteria to eukaryotic proteins. ORF-7 encodes a protein, the sequence of which contains a potentially transmembrane region and which has structural homologies with periplasmic proteins or proteins inserted in the external membrane of bacteria. The structural homologies of ORF-4 and ORF-7 have been identified with the aid of the PropSearch program.

Investigation of sequences homologous to other ORFs in GenBank with the aid of the BLAST program revealed a homology between the N-terminal regions of ORF-2 and filamentous haemagglutinin B of *Bordetella pertussis* (43% similarity, 36% identical over 352 amino acids) and between ORF-1 and the protein fhaC of *Bordetella pertussis* (35% similarity, 27% identical over 401 amino acids). ORF-1 and ORF-2 are neighbouring genes in the strain Z2491 and filamentous haemagglutinin B of *Bordetella pertussis* and fhaC are neighbouring genes in *Bordetella pertussis*, which reinforces the probability that these homologies reflect functional homologies.

Confirmation of the Specificity of Region 2 with Respect to Nm

Southern blots are carried out using the DNA probes obtained by PCR amplification of various parts of region 2 using oligonucleotide primers formulated from sequences of clones of region 2.

Figure 4:
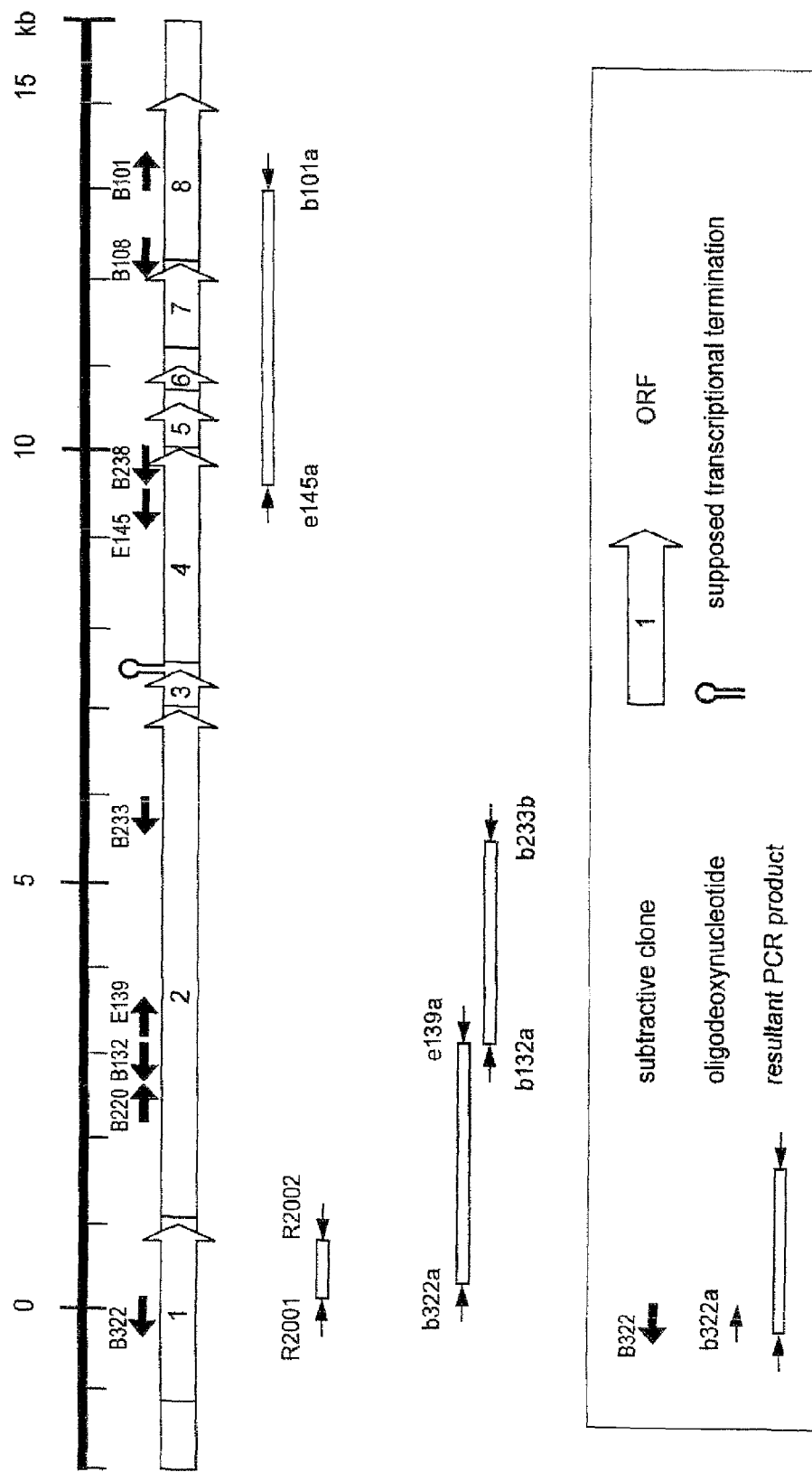
FIG. 4: the position in region 2 of the chromosome of No of oligonucleotides used as probes.

The approximate position of these oligonucleotides is shown on FIG. 4.

These are the oligonucleotides called R2001 (SEQ ID No. 46) and R2002 (SEQ ID No. 47) in one half of ORF-1, the oligonucleotides b332a (SEQ ID No. 48), e139a (SEQ ID No. 49), b132a (SEQ ID No. 50) and b233b (SEQ ID No. 51) in one half of ORF-1+the majority of ORF-2, and the oligonucleotides e145a (SEQ ID No. 52) and b101a (SEQ ID No. 53) in ⅓ of ORF-4+ORF-5 to 7.

The three Southerns are carried out under the following hybridization conditions:
16 h at 65° C.,
$NaPO_4$ 0.5 M, pH 7.2
EDTA-Na 0.001 M
1% sodium dodecylsulphate.

For the washing, heating is carried out for 10 min at 65° C., and $NaPO_4$ 0.5 M, pH 7.2; EDTA-Na 0.001 M, 1% sodium dodecylsulphate are used.

Figure 5:
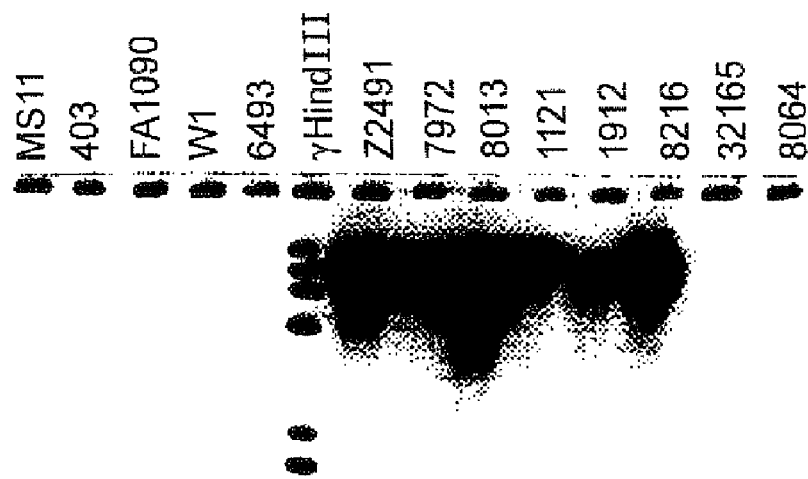
FIGS. 5, 6 and 7: the Southern blots of a panel of strains of the genus *Neisseria*, using parts of region 2 of Nm as probes.
Figure 6:
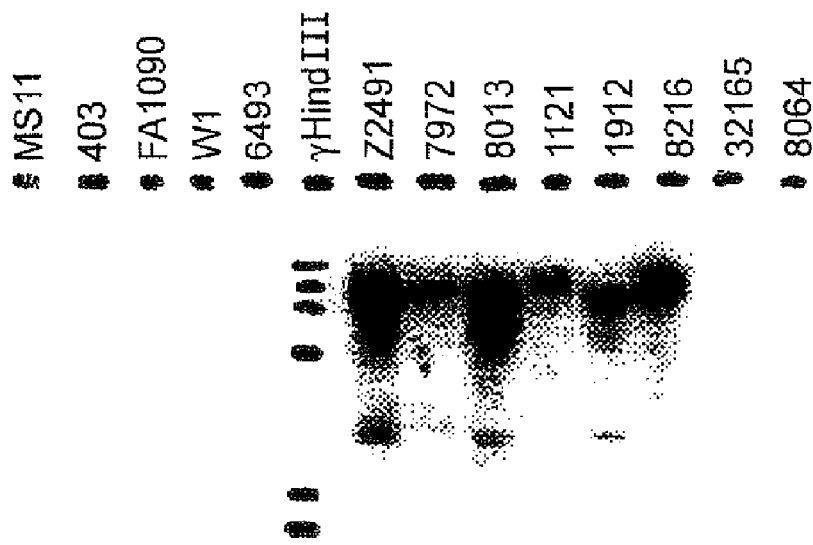
Figure 7:
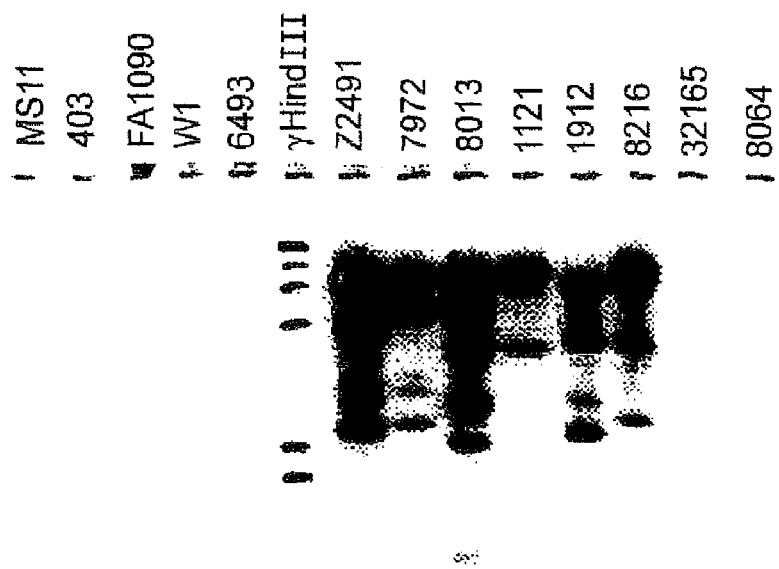

FIGS. 5, 6 and 7 respectively show the Southern blots obtained with each of the abovementioned ORF parts.

The 14 tracks correspond respectively, in each of the Southerns, to
1: MS11 (Ng)
2: 403 (Ng)
3: FA1090 (Ng)
4: W1 (Ng)
5: 6493 (Ng)
6: marker (lambda hindIII)
7: Z2491 (Nm, gpA)
8: 7972 (Nm gpA)
9: 8013 (Nm, gpC)
10: 1121 (Nm, grouping not possible)
11: 1912 (Nm, gpB)
13: 32165 (Nc)
14: 8064 (Nl).

Given that a panel of strains of *Neisseria* is used in these experiments and that each well is charged with a similar amount of digested DNA, these 3 Southern blots clearly show that the sequences corresponding to region 2 are found in all the meningococci tested and that significant homologous sequences do not exist in the genome of the Ng of the strains tested.

EXAMPLE 4

Identification of Regions of the Nm Genome Absent from Nl and Common with Ng

The technique described in example 1 is followed, but the chromosomal DNA of one strain of Nm (Z2491) and 2 strains of Nl (XN collections), equal parts of the DNAs of which are mixed, is used.

2 subtractions are performed using the R and J series of primers. Three different banks are thus obtained.

Two banks, called Bam and Eco, are obtained respectively by digestion of the chromosomal DNA of Nm Z2491 bp MboI and Tsp509I; a third bank, called Cla, which results from digestion of the chromosomal DNA of Nm by is obtained using the primer set RMsp10, RMsp24, JMsp10 and JMsp24. All the primers used are shown in the following table 2.

TABLE 2

Adapters for differential banks

| Chromosomal DNA digested by | | Cloning in pBluescript by |
|---|---|---|
| MboI | → | BamHI |
| Tsp509I | → | EcoRI |
| MspI | → | ClaI |

First subtraction cycle

| RBam12: | 3' AGTGGCTCCTAG 5' | (SEQ ID No. 54) |
| RBam24: | 5' AGCACTCTCCAGCCTCTCACCGAG 3' | (SEQ ID No. 55) |
| REco12: | AGTGGCTCTTAA | (SEQ ID No. 56) |
| RBam24: | 5' AGCACTCTCCAGCCTCTCACCGAG 3' | (SEQ ID No. 55) |

(REco 24 = RBam 24)

| RMsp10: | AGTGGCTGGC | (SEQ ID No. 57) |
| RMsp24: | 5' AGCACTCTCCAGCCTCTCACCGAC 3' | (SEQ ID No. 58) |

Second subtraction cycle

| Jbam12: | 3' GTACTTGCCTAG 5' | (SEQ ID No. 59) |
| JBam24: | 5' ACCGACGTCGACTATCCATGAACG 3' | (SEQ ID No. 60) |
| JEco12: | GTACTTGCTTAA | (SEQ ID No. 61) |
| JBam24: | 5' ACCGACGTCGACTATCCATGAACG 3' | (SEQ ID No. 60) |

(JEco 24 = JBam 24)

| JMsp10: | GTACTTGGOC | (SEQ ID No. 62) |
| JMsp24: | 5' ACCGACGTCGACTATCCATGAACC 3' | (SEQ ID No. 63) |

After 2 subtractions, the entire product of each amplification is labelled and used as a probe.

The subtractive banks are checked by Southern blotting over a panel of 12 strains of *Neisseria* (chromosomal DNA cut by ClaI). The hybridization conditions are identical to those given in example 1.

Figure 8A:
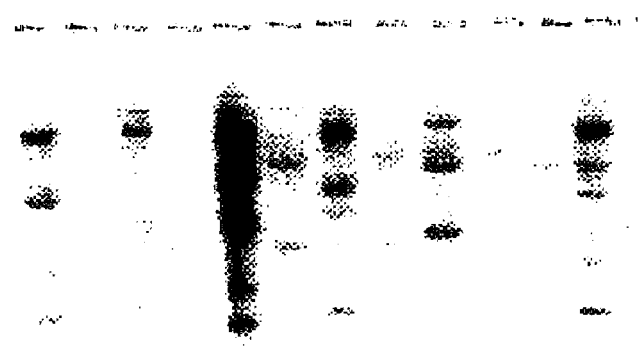
FIGS. 8A to 8C: the Southern blots with 3 subtractive banks over a panel of 12 strains of *Neisseria*.
Figure 8B:
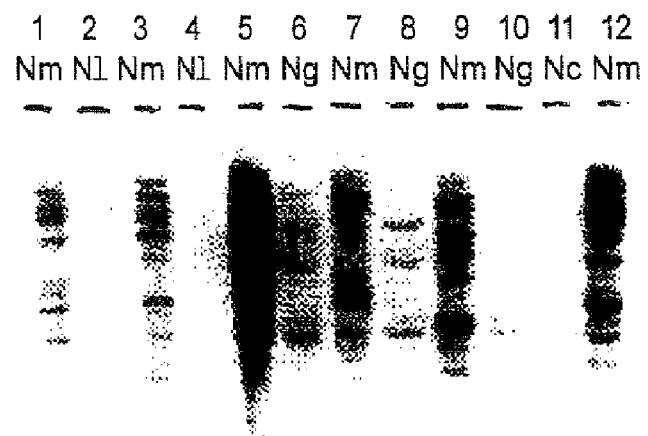
Figure 8C:
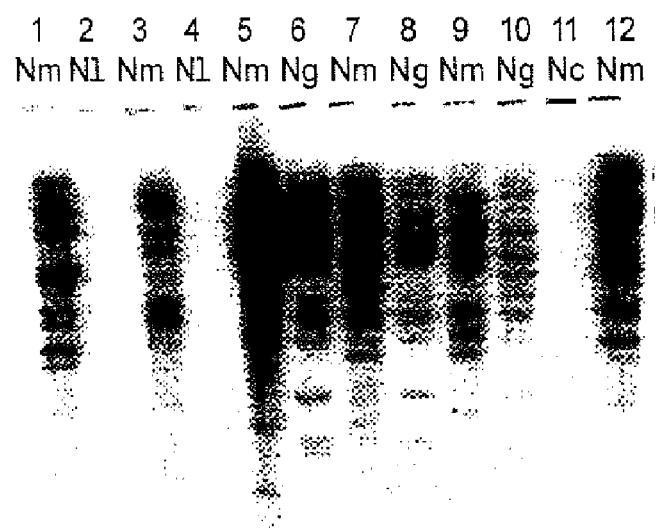

These Southern blots are shown on FIGS. 8A to 8C, which relate respectively to the MboI/BamHI bank, to the MspI/ClaI bank and to the Tsp509I/EcoRI bank.

The 12 tracks correspond respectively, to
1: Nm Z2491 (group A)
2: Nl 8064
3: Nm 8216 (group B)
4: Nl 9764
5: Nm 8013 (group C)
6: Ng MS11
7: Nm 1912 (group A)
8: Ng 4C1
9: Nm 1121 (grouping not possible)
10: Ng FA1O9O
11: Nc 32165
12: Nm 7972 (group A)

Examination of the Southern blots shows that the sequences contained in each bank are specific to Nm and are not found in Nl. Furthermore, the reactivity found with the strains of Ng suggests that some of these sequences are present in Ng.

Figure 11:
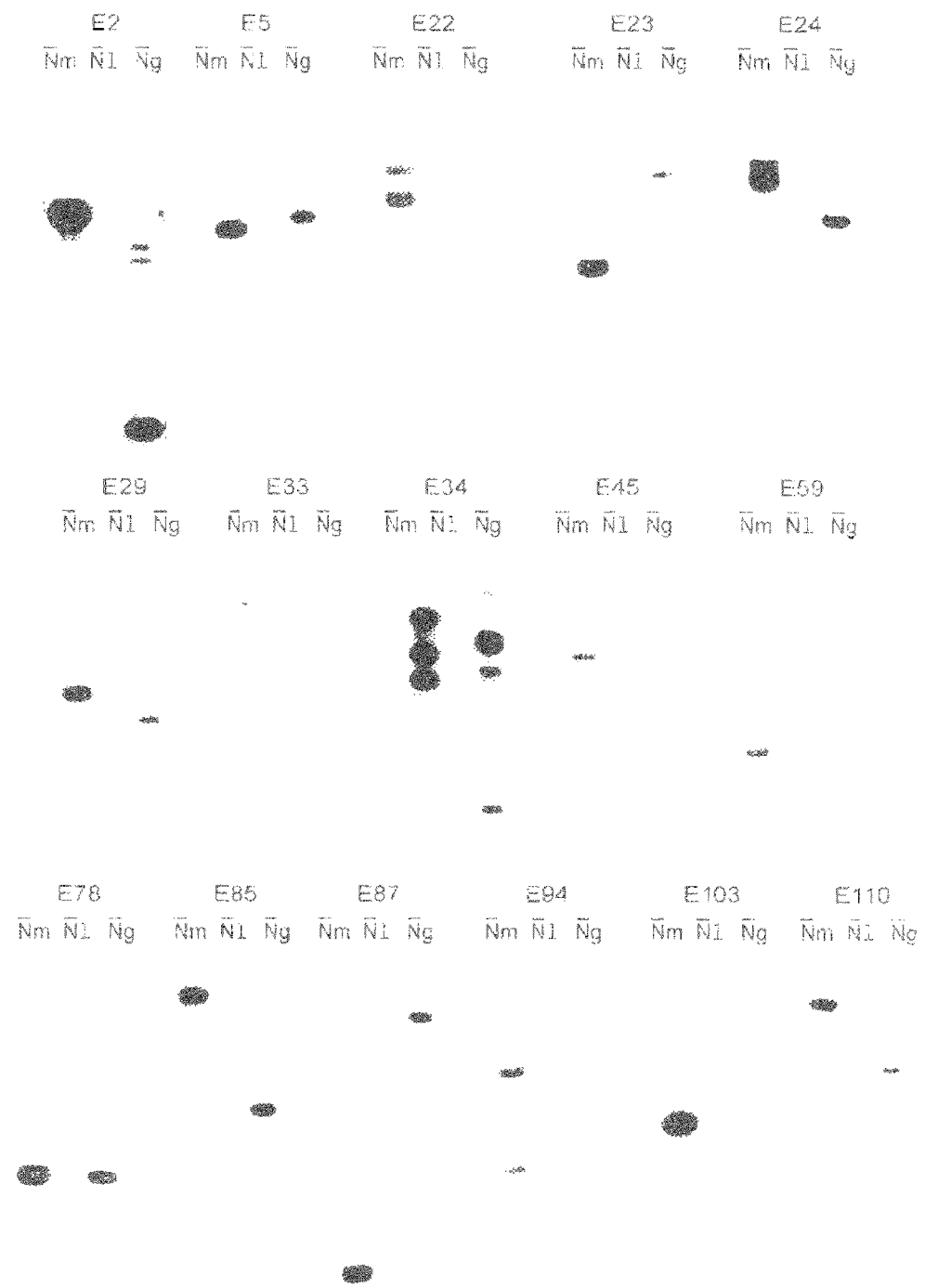

Each of these banks was then cloned in pBluescript at the BamHI site for Bam, or the EcoRI sit for Eco, or the ClaI site for Cla. In order to confirm the specificity of the clones with respect to the Nm genome, restriction of the individual clones and radiolabelling thereof were carried out. The clones showing reactivity for both Nm and Ng were kept for subsequent studies. These clones are shown on FIGS. 9, 10 and 11, which give the profiles with respect of Nm, Nl and Ng of 5 clones of the Bam bank (FIG. 9), 16 clones of the Eco bank (FIGS. 10) and 13 clones of the Cla bank (FIG. 11).

These clones were sequenced using universal and reverse primers. They are

Bam Clones
partial B11 of 140 bp (SEQ ID No. 66), partial B13 estimated at 425 bp (SEQ ID No. 67), B26 of 181 bp (SEQ ID No. 68), B33 of 307 bp (SEQ ID No. 69), B40 of 243 bp (SEQ ID No. 70), Cla Clones
C16 of 280 bp (SEQ ID No. 72), partial C20 estimated at 365 bp (SEQ ID No. 73), partial C24 estimated at 645 bp (SEQ ID No. 74), partial C29 estimated at 245 bp (SEQ ID No. 75), C34 of 381 bp (SEQ ID No. 76), C40 of 269 bp (SEQ ID No. 77), C42 of 203 bp (SEQ ID No. 78), p C43 of 229 bp (SEQ ID No. 79), C45 of 206 bp (SEQ ID No. 80), C47 of 224 bp (SEQ ID No. 81), C62 of 212 bp (SEQ ID No. 82), and C130 (5' . . . ) estimated at 900 bp (SEQ ID No. 83), and Eco Clones
E2 of 308 bp (SEQ ID No. 84), partial E5 estimated at 170 bp (SEQ ID No. 85), partial E22 estimated at 300 bp (SEQ ID No. 86), E23 of 273 bp (SEQ ID No. 87), E24 of 271 bp (SEQ ID No. 88), E29 of 268 bp (SEQ ID No. 89), partial E33 estimated at 275 bp (SEQ ID NO. 90), partial E34 estimated at 365 bp (SEQ ID No. 91), E45 of 260 bp (SEQ ID No. 92), E59 estimated at greater than 380 bp (SEQ ID No. 93), E78 of 308 bp (SEQ ID No. 94), E85 of 286 bp (SEQ ID No. 95), E87 of 238 bp (SEQ ID No. 96), partial E94 greater than 320 bp (SEQ ID No. 97), partial E103 greater than 320 bp (SEQ ID No. 98) and E110 of 217 bp (SEQ ID No. 99).

Mapping of each clone was carried out on the chromosome of Nm Z2491 as described in example 1. The results obtained are given on the right-hand part of FIG. 2. It is found that these clones correspond to regions called 4 and 5. These regions are therefore made up of sequences present both in Nm and in Ng, but not found in Nl. It is therefore regarded that these are sequences which code for virulence factors responsible for the initial colonization and penetration of the mucosa. Region 4 is located between argF and regF on the chromosome of Nm 2491 [sic], and region 5 is located between the lambda 375 marker and penA. This region probably contains sequences which code for an Opa variant and a protein which binds transferrin.

A comparison with the known sequences in the databanks has half [sic] that in region 4 only the clone C130 has a homology, that is to say with MspI methylase. In region 5, no homology with known sequences was found with the clones C8, E2, B40, C45, E23 and E103. For the other clones, the homologies are the following:

B11 arginine decarboxylase SpeA; C29 arginine decarboxylase SpeA; C62 oxoglutarate/malate transporter; repetitive DNA element; E34 repetitive DNA element; E94 murine endopeptidase MepA; C47 citrate synthase PrpC; E78 citrate synthase PrpC

EXAMPLE 5

Demonstration of the Presence of One or More Strains of Neisseria meningitidis in a Biological Sample A biological sample of the cephalorachidian fluid, urine, blood or saliva type is taken.

After filtration and extraction, the DNAs present in this sample are subjected to gel electrophoresis and transferred to a membrane by Southern blotting.

A nucleotide probe constructed by labelling SEQ ID No. 5 with $^{32}$P is incubated with this transfer membrane.

After autoradiography, the presence of reactive band(s) allows diagnosis of the presence of Neisseria meningitidis in the sample.

EXAMPLE 6

Vaccine Composition Including in its Spectrum Antimeningococcal Prophylaxis and Intended for Prevention of any Form of Infection by Neisseria meningitidis The peptide coded by a sequence including SEQ ID No. 10 is conjugated with a toxin.

This conjugated peptide is then added to a composition comprising the anti-Haemophilus and antipneumococcal vaccine, or any other childhood vaccine.

After having been sterilized, the resulting composition can be injected parenterally, subcutaneously or intramuscularly.

This same composition can also be sprayed on to mucosa with the aid of a spray.

The invention claimed is:

1. An isolated DNA which is specific to *Neisseria meningitidis* (Nm) and hybridizes on a Southern blot to SEQ ID NO: 10 and does not hybridize on a Southern blot to a DNA sequence of *Neisseria gonorrhoeae* (Ng) strain MS11, under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA, and 1% SDS, the final wash being conducted at 65° C. for 5 minutes, or the complement of said isolated DNA which is specific to *Neisseria meningitidis* (Nm), provided that said DNA or the complement of said isolated DNA is not pilC, or a gene involved in the biosynthesis of any one of the polysaccharide capsule, IgA proteases, pilin, a protein which binds transferrin, a protein which binds lactoferin, and an opacity protein said DNA being within an islet involved in the colonization of the nasopharynx or invasion of the submucousal space or systemic dissemination of Nm.

2. A composition comprising the DNA or complement of claim 1 and a carrier.

3. An isolated DNA which is specific to *Neisseria meningitidis* (Nm) and hybridizes on a Southern blot to SEQ ID NO:10 and does not hybridize on a Southern blot to a DNA sequence of *Neisseria gonorrhoeae* (Ng) strain MS11, under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA and 1% SDS, the final wash being conducted at 65° C. for 5 minutes, or the complement of said isolated DNA which is specific to *Neisseria meningitidis* (Nm), provided that said DNA or the complement of said isolated DNA is not pilC, or a gene involved in the biosynthesis of any one of the polysaccharide capsule, IgA proteases, pilin, a protein which binds transferrin, a protein which binds lactoferin, and an opacity protein.

4. A composition comprising the DNA or complement of claim 3 and a carrier.

5. A method of detecting *Neisseria meningitidis* (Nm) in a sample from a patient, said method comprising providing isolated sample DNA of said sample from the patient, contacting said sample DNA with the isolated DNA of claim 1, said contacting being performed under conditions which allow hybridization of said sample DNA and said isolated DNA, and detecting any hybridization of said sample DNA and said isolated DNA, such that said hybridization of said sample DNA and said isolated DNA specifically indicates the presence of said Nm in said sample, wherein said isolated DNA is specific to Nm and does not hybridize on a Southern blot to a DNA sequence of *Neisseria gonorrhoeae* (Ng) strain MS11 under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA, and 1% SDS, the final wash being conducted at 65° C. for 5 minutes, and wherein said isolated DNA specifically hybridizes to Nm DNA in the presence of Ng DNA.

6. A method of detecting *Neisseria meningitidis* (Nm) in a sample from a patient, said method comprising providing isolated sample DNA of said sample from the patient, contacting said sample DNA with the composition of claim 2 under conditions which allow hybridization of said sample DNA and DNA in said composition, and detecting any hybridization of said sample DNA and said DNA in said composition, such that said hybridization of said sample DNA and said DNA in said composition specifically indicates the presence of said Nm or Ng in said sample, wherein said DNA in said composition is specific to Nm and does not hybridize on a Southern blot to a DNA sequence of *Neisseria gonorrhoeae* strain MS11 under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA, and 1% SDS, the final wash being conducted at 65° C. for 5 minutes, and wherein said DNA in said composition specifically hybridizes to Nm DNA in the presence of Ng DNA.

7. A method of detecting *Neisseria meningitidis* (Nm) in a sample from a patient, said method comprising providing isolated sample DNA of said sample from the patient, contacting said sample DNA with the isolated DNA of claim 3, said contacting being performed under conditions which allow hybridization of said sample DNA and said isolated DNA, and detecting any hybridization of said sample DNA and said isolated DNA, such that said hybridization of said sample DNA and said isolated DNA specifically indicates the presence of said Nm in said sample, wherein said isolated DNA is specific to Nm and does not hybridize on a Southern blot to a DNA sequence of *Neisseria gonorrhoeae* (Ng) MS11 under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA, and 1% SDS, the final wash being conducted at 65° C. for 5 minutes, and wherein said isolated DNA specifically hybridizes to Nm DNA in the presence of Ng DNA.

8. A method of detecting *Neisseria meningitidis* (Nm) in a sample from a patient, said method comprising providing isolated sample DNA of said sample from the patient, contacting said sample DNA with the composition of claim 4 under conditions which allow hybridization of said sample DNA and DNA in said composition, and detecting any hybridization of said sample DNA and said DNA in said composition, such that said hybridization of said sample DNA and said DNA in said composition specifically indicates the presence of said Nm or Ng in said sample, wherein said DNA in said composition is specific to Nm and does not hybridize on a Southern blot to a DNA sequence of *Neisseria gonorrhoeae* (Ng) strain MS11 under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA, and 1% SDS, the final wash being conducted at 65° C. for 5 minutes, and wherein said DNA in said composition specifically hybridizes to Nm DNA in the presence of Ng DNA.

9. The DNA of claim 1 wherein said *Neisseria meningitidis* (Nm) is *Neisseria meningitidis* (Nm) Z2491.

10. A composition comprising the DNA or complement of claim 9 and a carrier.

11. The DNA of claim 3 wherein said *Neisseria meningitidis* (Nm) is *Neisseria meningitidis* (Nm) Z2491.

12. A composition comprising the DNA or complement of claim 11 and a carrier.

13. A method of detecting *Neisseria meningitidis* (Nm) in a sample from a patient, said method comprising providing isolated sample DNA of said sample from the patient, contacting said sample DNA with the isolated DNA of claim 9, said contacting being performed under conditions which allow hybridization of said sample DNA and said isolated DNA, and detecting any hybridization of said sample DNA and said isolated DNA, such that said hybridization of said sample DNA and said isolated DNA specifically indicates the presence of said Nm in said sample, wherein said isolated DNA is specific to Nm Z2491 and does not hybridize on a Southern blot to a DNA sequence of *Neisseria gonorrhoeae* (Ng) strain MS11 under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA, and 1% SDS, the final wash being conducted at 65° C. for 5 minutes, and wherein said isolated DNA specifically hybridizes to Nm DNA in the presence of Ng DNA.

14. A method of detecting *Neisseria meningitidis* (Nm) in a sample from a patient, said method comprising providing isolated sample DNA of said sample from the patient, contacting said sample DNA with the composition of claim 10 under conditions which allow hybridization of said sample DNA and DNA in said composition, and detecting any hybridization of said sample DNA and said DNA in said composition, such that said hybridization of said sample DNA and said DNA in said composition specifically indicates the presence of said Nm or Ng in said sample, wherein said DNA in said composition is specific to Nm Z2491 and does not hybridize on a Southern blot to a DNA sequence of *Neisseria gonorrhoeae* strain MS11 under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA, and 1% SDS, the final wash being conducted at 65° C. for 5 minutes, and wherein said DNA in said composition specifically hybridizes to Nm DNA in the presence of Ng DNA.

15. A method of detecting *Neisseria meningitidis* (Nm) in a sample from a patient, said method comprising providing isolated sample DNA of said sample from the patient, contacting said sample DNA with the isolated DNA of claim 11, said contacting being performed under conditions which allow hybridization of said sample DNA and said isolated DNA, and detecting any hybridization of said sample DNA and said isolated DNA, such that said hybridization of said sample DNA and said isolated DNA specifically indicates the presence of said Nm in said sample, wherein said isolated DNA is specific to Nm Z2491 and does not hybridize on a Southern blot to a DNA sequence of *Neisseria gonorrhoeae* (Ng) MS11 under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA, and 1% SDS, the final wash being conducted at 65° C. for 5 minutes, and wherein said isolated DNA specifically hybridizes to Nm DNA in the presence of Ng DNA.

16. A method of detecting *Neisseria meningitidis* (Nm) in a sample from a patient, said method comprising providing isolated sample DNA of said sample from the patient, contacting said sample DNA with the composition of claim 12 under conditions which allow hybridization of said sample DNA and DNA in said composition, and detecting any hybridization of said sample DNA and said DNA in said composition, such that said hybridization of said sample DNA and said DNA in said composition specifically indicates the presence of said Nm or Ng in said sample, wherein said DNA in said composition is specific to Nm Z2491 and does not hybridize on a Southern blot to a DNA sequence of *Neisseria gonorrhoeae* (Ng) strain MS11 under the following hybridization conditions: 16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM Na PO$_4$ pH 7.2, 1 mM EDTA, and 1% SDS, the final wash being conducted at 65° C. for 5 minutes, and wherein said DNA in said composition specifically hybridizes to Nm DNA in the presence of Ng DNA.

\* \* \* \* \*